US006852844B1

(12) United States Patent
Yu et al.

(10) Patent No.: US 6,852,844 B1
(45) Date of Patent: Feb. 8, 2005

(54) HUMAN PROTOCADHERIN PROTEINS AND POLYNUCLEOTIDES ENCODING THE SAME

(75) Inventors: Xuanchuan (Sean) Yu, Houston, TX (US); Maricar Miranda, Houston, TX (US); C. Alexander Turner, Jr., The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 275 days.

(21) Appl. No.: 10/025,225

(22) Filed: Dec. 19, 2001

Related U.S. Application Data

(60) Provisional application No. 60/257,257, filed on Dec. 20, 2000.

(51) Int. Cl.[7] ................................................ C12N 1/20

(52) U.S. Cl. ........................ 536/23; 536/23.2; 435/91.1

(58) Field of Search ........................ 536/23.2; 435/91.1

(56) References Cited

U.S. PATENT DOCUMENTS

| | | | |
|---|---|---|---|
| 4,215,051 A | 7/1980 | Schroeder et al. | |
| 4,376,110 A | 3/1983 | David et al. | |
| 4,594,595 A | 6/1986 | Struckman | |
| 4,631,211 A | 12/1986 | Houghten | |
| 4,689,405 A | 8/1987 | Frank et al. | |
| 4,713,326 A | 12/1987 | Dattagupta et al. | |
| 4,873,191 A | 10/1989 | Wagner et al. | |
| 4,946,778 A | 8/1990 | Ladner et al. | |
| 5,252,743 A | 10/1993 | Barrett et al. | |
| 5,272,057 A | 12/1993 | Smulson et al. | |
| 5,424,186 A | 6/1995 | Fodor et al. | |
| 5,445,934 A | 8/1995 | Fodor et al. | |
| 5,459,127 A | 10/1995 | Felgner et al. | |
| 5,556,752 A | 9/1996 | Lockhart et al. | |
| 5,700,637 A | 12/1997 | Southern | |
| 5,723,323 A | 3/1998 | Kauffman et al. | |
| 5,744,305 A | 4/1998 | Fodor et al. | |
| 5,830,721 A | 11/1998 | Stemmer et al. | |
| 5,837,458 A | 11/1998 | Minshull et al. | |
| 5,869,336 A | 2/1999 | Meyer et al. | |
| 5,877,397 A | 3/1999 | Lonberg et al. | |
| 5,948,767 A | 9/1999 | Scheule et al. | |
| 6,075,181 A | 6/2000 | Kucherlapati et al. | |
| 6,110,490 A | 8/2000 | Thierry | |
| 6,150,584 A | 11/2000 | Kucherlapati et al. | |

OTHER PUBLICATIONS

Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Cote et al., 1983, "Generation of human monoclonal antibodies reactive with cellular antigens," Proc. Natl. Acad. Sci. USA 80:2026–2030.
Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.
Gordon, 1989, "Transgenic Animals", International Review of Cytology, 115:171–229.
Greenspan et al, 1993, "Idiotypes: structure and immunogenicity", FASEB Journal 7:437–444.
Gu et al, 1994, "Deletion of a DNA Polymerase β Gene Segment in T Cells Using Cell Type–Specific Gene Targeting", Science 265:103–106.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the Ipp gene of *Escherichia coli*", Nucleic Acids Research 13(9):3101–3110.
Janknecht et al, 1991, "Rapid and efficient purification of native histidine–tagged protein expressed by recombinant vaccinia virus", PNAS 88:8972–8976.
Kohler & Milstein, 1975, "Continuous cultures of fused cells secreting antibody of predefined specificity", Nature 256:495–497.
Lakso et al, 1992, "Targeted oncogene activation by site–specific recombination in transgenic mice", Proc. Natl. Acad. Sci. USA 89:6232–6236.
Lavitrano et al, 1989, "Sperm Cells as Vectors for Introducing Foreign DNA into Eggs: Genetic Transformation of Mice", Cell 57:717–723.
Lo, 1983, "Transformation by Iontophoretic Microinjection of DNA: Multiple Integrations without Tandem Insertions", Mol. & Cell. Biology 3(10):1803–1814.
Logan et al, 1984, "Adenovirus tripartite leader sequence enhances translation of mRNAs late after infection", Proc. Natl. Acad. Sci. USA 81:3655–3659.
Lowy et al, 1980, "Isolation of Transforming DNA: Cloning the Hamster aprt Gene", Cell 22:817–823.

(List continued on next page.)

Primary Examiner—Christopher Tate
Assistant Examiner—Roy Teller

(57) ABSTRACT

Novel human polynucleotide and polypeptide sequences are disclosed that can be used in therapeutic, diagnostic, and pharmacogenomic applications.

8 Claims, No Drawings

OTHER PUBLICATIONS

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient Insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264:(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

SEQUENCE LISTING

<160> NUMBER OF SEQ ID NOS: 8
<210> SEQ ID NO 1
<211> LENGTH: 13770
<212> TYPE: DNA
<213> ORGANISM: homo sapiens

<400> SEQUENCE: 1

| | | | | | |
|---|---|---|---|---|---|
| atggatataa | ttatgggaca | ctgtgtgggc | acacggcctc | ctgcttgttg | cctcatcctc | 60 |
| ctgcttttca | agcttttggc | cactgtctcc | caggggctgc | cagggactgg | acccctgggc | 120 |
| ttccacttca | cacattccat | ttataatgct | accgtgtatg | agaactcagc | agcaaggacc | 180 |
| tacgtcaaca | gccagagtag | aatgggcatc | accttaatag | atctatcctg | ggatatcaaa | 240 |
| tacagaatag | tgtccggaga | cgaggaaggc | ttttcaaag | cagaggaagt | catcattgca | 300 |
| gatttctgtt | ttctcagaat | aagaactaaa | ggtggcaatt | ctgccatatt | aaatagggaa | 360 |
| atccaggata | attatttatt | gatagtaaaa | ggttctgtca | gaggagagga | tttggaagca | 420 |
| tggaccaaag | tgaatataca | ggttttagat | atgaatgatc | tgagaccttt | gttttcaccc | 480 |
| acaacatact | ctgttaccat | agcagaaagc | acacctctaa | ggactagtgt | tgcccaggtg | 540 |
| actgcaacag | acgcagatat | tggttccaat | ggagaattct | actactactt | taaaaataaa | 600 |
| gttgatctct | tttcagttca | ccccacgagt | ggtgtcatct | ccttaagtgg | tcgattaaat | 660 |
| tatgatgaaa | agaataggta | tgatctggaa | attttggctg | tggaccgggg | aatgaaactg | 720 |
| tatgggaaca | atggagtgag | cagtactgca | aagctttatg | ttcacattga | gcgcataaat | 780 |
| gaacatgccc | caacaatcca | tgtagtcact | catgttcctt | tctcgttgga | aaaagagcca | 840 |
| acatatgcag | tggtgacagt | tgatgactta | atgatggag | cgaatggaga | gatcgaatct | 900 |
| gtttccattg | tggctgggga | tccttttagat | cagttcttcc | tggctaagga | aggaaagtgg | 960 |
| ttgaatgagt | acaagattaa | ggagaggaag | cagattgact | gggagagctt | tccctatggc | 1020 |
| tacaatctca | ctcttcaagc | aaaagacaag | ggatctcctc | aaaaatgttc | agcattaaag | 1080 |
| gcagtctaca | ttggcaaccc | cacaagagac | actgtcccca | ttagatttga | aaagaagtg | 1140 |
| tacgatgtga | gcataagtga | atttttcccct | cctggtgtcg | tggttgctat | agtaaaatta | 1200 |
| agtcctgaac | cgatagatgt | ggaatacaaa | ttatctcctg | gtgaggatgc | agtgtacttt | 1260 |
| aaaattaatc | ctcggtcggg | tctgattgtt | acagcacggc | cactgaatac | tgttaagaag | 1320 |
| gaggtttata | aactggaggt | gacaaacaag | gaaggagatt | taaaagcaca | ggtcaccatc | 1380 |
| agcatagaag | atgcaaatga | ccacaccccca | gaatttcagc | aaccactgta | tgatgcttat | 1440 |
| gtgaatgaaa | gtgtcccagt | gggaaccagc | gttctaacag | tttcagcttc | tgataaggat | 1500 |
| aaaggagaaa | atgggtacat | cacctatagt | atcgctagcc | tgaatttgtt | accatttgtc | 1560 |
| attaatcagt | ttacaggtgt | tattagcaca | actgaagaac | tggatttga | atcctcccca | 1620 |
| gaaatttaca | gattcattgt | tagagcctct | gactggggtt | caccataccg | ccatgaaagt | 1680 |
| gaggtcaatg | tgactattcg | aataggaaat | gtcaacgaca | acagccctct | ctttgaaaaa | 1740 |
| gtggcttgcc | agggagttat | ttcatatgac | tttccagttg | gtggtcacat | cacagcagtc | 1800 |
| tcagcgatcg | atatcgatga | acttgaactt | gtaaagtaca | aaatcatttc | tggaaatgaa | 1860 |
| cttggcttct | tttatttaaa | cccagattct | ggtgtttac | agcttaaaaa | atcactgaca | 1920 |
| aattctggca | ttaaaaatgg | caatttttgcc | ctcagaatta | cagcaactga | tggagagaat | 1980 |
| cttgcagacc | ccatgtctat | taacatttca | gtcctacatg | ggaaagtgtc | ttcaaagagc | 2040 |

-continued

```
ttcagttgca gagaaactcg tgtggctcaa aagctggcag agaaactact cattaaggca    2100
aaagcaaatg ggaaactgaa tctggaagat ggatttcttg acttttattc aattaataga    2160
cagggaccat attttgacaa gtcttttcct tctgatgtgg ctgtaaagga ggatctgcca    2220
gttggtgcta acattctgaa gattaaagcc tatgatgccg actctggctt caatggaaaa    2280
gtgctattta caatatcaga tggaaatacg gatagttgct ttaatattga tatggagact    2340
gggcagctta aagtccttat gcccatggat cgagaacaca cagacctcta tctccttaat    2400
atcaccatct atgacttagg taatccacag aaatcgtcat ggagactgct gaccatcaat    2460
gtggaggatg ctaatgacaa tagcccagtt tttattcaag acagttactc agttaacatt    2520
cttgaaagtt caggcattgg tactgaaatc attcaagtgg aagccagaga caaagactta    2580
ggttctaatg tgaagtgac ttactcagtc ttgacagata cacagcagtt tgccatcaat    2640
agctcaactg gaatcgttta tgtagccgac cagttggacc gggaatccaa agccaattat    2700
tctttgaaaa tagaagccag ggacaaggca gagagtggtc agcagctgtt ttcagttgtc    2760
actcttaaag tttttttaga tgatgtcaat gactgctccc cagctttcat tcccagtagc    2820
tatagtgtga aggttcttga agatctccct gttggcactg tcattgcttg gcttgagacc    2880
catgatccag atcttggact gggggtcaa gtgcgctatt cttggtcaa tgactataat    2940 gggagatttg aaatagataa agcaagtggt gccatccgct tgagcaaaga gcttgattat    3000
gagaaacagc agttctataa ccttactgtg cgggccaaag acaaagggcg gcctgtctct    3060
ctgtcatctg tttcctttgt tgaggtgaaa gtggtggatg tcaatgaaaa cctccacact    3120
ccctatttcc cagactttgc tgttgttgga tctgtaaagg aaaactcacg cattggaaca    3180
agcgtgctgc aggtgactgc tcgagatgaa gactccggaa gggatggaga gatccagtac    3240
tccatcaggg atggcagtgg tcttggaagg ttcagtatag acgacgagag tggggtcatc    3300
actgccgcag acattcttga tcgggagaca atggggtcat actggctaac agtgtatgcc    3360
acagacaggg gcgttgttcc actctactcc accattgagg tctacattga agttgaagat    3420
gtgaatgaca atgccccgct gacctcagaa cctatatatt atcctgttgt catggaaaac    3480
tctccaaagg acgtatctgt cattcagatc caggctgaag atcctgactc cagttccaat    3540
gaaaaactga catacaggat tacaagtgga aatcctcaga atttttttgc catcaatatc    3600
aaaacaggtc tgattacaac aacttcaagg aaattggatc gagaacagca ggcagaacat    3660
tttctggagg tgactgtgac agatggtggt ccctctccaa aacagtcaac catttgggtg    3720
gtggttcagg ttctagatga aaatgacaac aagcccagt tcccagagaa ggtctaccag    3780
atcaagctgc cagaacgtga ccgaaagaag agaggagaac cgatttacag ggcttttgca    3840
tttgatagag atgagggccc caacgcagaa atctcctaca gtattgtgga tgggaatgat    3900
gacggaaagt tctttattga ccctaaaact gggatggttt cttctagaaa gcagtttaca    3960
gcaggcagtt atgacatcct aacgataaag gcagtgdaca atgggcgccc acagaaatcc    4020
tccacggccc gcctccacat tgaatggatt aagaaaccac ccccttcacc tataccattg    4080
accttcgatg agccgtttta taacttcaca gtcatggaaa gtgatagagt gactgaaatt    4140 gtagggtgg tgtctgtgca gccagctaac acccctctgt ggtttgacat agttgggggg    4200
aattttgaca gcgcttttga tgcagagaag ggtgttggga caattgtcat cgcaaaacct    4260
ttggatgcag agcagaggtc catctataat atgagtgtgg aagtcaccga tggacaaat    4320 gttgctgtta ctcaggtatt tatcaaagtg ctggataata atgataatgg cccagaattc    4380
tctcagccga attacgatgt gacaatttcc gaggatgtgc ttccagacac ggagatcctg    4440
```

```
cagattgaag ccacagatag agatgagaag cacaagctga gctacactgt tcatagcagc    4500
atcgactcca tcagcatgag aaaattccgg attgaccctg cactggcgt gctctatact    4560 gccgagaggc tggaccatga ggcccaggac aagcacattc tcaacataat ggtcagagat    4620
caggagtttc cttatcgaag aaacttggcc cgagtcattg tgaatgtgga ggatgctaat    4680
gatcacagtc cttattttac caacccactg tatgaagcgt ctgtgtttga atctgctgct    4740
ctgggatcag ctgttctgca agtgacggct ctggacaaag acaaggaga aaatgcagaa    4800 ctcatatata ccatagaagc agggaacact gggaacatgt ttaagatcga accggtccta    4860
ggcatcatca ccatttgcaa agaaccagac atgacgacga tgggtcagtt tgtcctatcc    4920
atcaaagtca cagatcaggg atccccgcca atgtctgcta ctgcaattgt gcgcatttcc    4980
gtcaccatgt ctgacaattc tcaccccaag ttcattcaca aagactacca agcagaagta    5040
aatgaaaatg ttgacattgg aacatcagtc attctaatct ctgccatcag tcaatctacc    5100
ctcatttatg aagtcaaaga tggagacatt aatgggatct taccataaa tccatattct    5160 ggagtcatca ccactcagaa ggccctggat tatgagcgca catcctctta tcaactcatc    5220
attcaggcca ccaatatggc aggaatggct tccaatgcta cagtcaatat tcagattgtt    5280
gatgaaaatg ataatgcccc agttttctc ttttctcaat actcaggcag cctaagtgag    5340
gctgccccaa ttaatagcat tgtcaggagc ttggataaca gcccactggt gattcgagcc    5400
acagatgctg acagcaaccg gaatgctctg cttgtgtatc agattgtgga gtcaacagca    5460
aaaaagtttt tcacggtgga ctccagtaca ggtgcaatca gaacaattgc caacctggac    5520
catgaaacca ttgcccattt ccattttcat gtgcatgtga gagacagtgg tagcccccaa    5580
ctgactgcag agagtcccgt tgaagtcaac attgaggtga cagatgtgaa tgataaccca    5640
cctgttttta ctcaggctgt gtttgagact atcttacttc tacctaccta tgttggagtg    5700
gaggttctga agttagtgc cacagatcct gactctgagg taccccctga actgacatac    5760
agcctaatgg aaggcagttt ggatcatttt ttaattgact caaacagtgg agtacttacc    5820
ataaaaaaca caacctctc caaggatcac tacatgctga tagttaaggt gtctgatgga    5880
aagttctaca gtacctccat ggtcaccatc atggttaaag aagccatgga cagcggcctc    5940
cactttacac aaagcttcta ttccacctca atctcagaga caacactaa cataaccaaa    6000 gttgctattg tcaatgcagt tggaaatcgc cttaatgagc ccttaaaata cagcatctta    6060
aacccaggaa ataagttcaa gataaaatct acctcagggg tcattcagac gactggagtc    6120 cccttttgacc gtgaagaaca agagttatat gagctggtgg tagaagccag ccgtgagctg    6180
gaccatctgc gtgtggccag agtggtggtc agggttaaca ttgaagacat aaatgacaat    6240
tctccagtct tgtgggcct cccatactat gctgctgttc aagtggatgc ggaacccggg    6300
actctgattt atcaggtgac agccattgac aaagataaag gtccaaatgg agaagtgacc    6360
tatgtcctgc aggatgacta tggccacttt gaaattaacc ctaattcagg gaatgttatt    6420
ttaaaggaag cattcaactc tgacttgtcc aacattgagt atggagtcac catcctagcc    6480
aaggatggcg gaaaaccttc tttgtctaca tctgtggagc ttcccatcac tattgtcaac    6540
aaagcaatgc ctgtgtttga taagcccttt tatacagcat ctgtcaatga agacatcaga    6600
atgaacacac ccatcctaag catcaatgcc accagtccag aaggccaagg catcatatat    6660
atcattatcg atgggaccc ttttaaacag tttaacattg actttgacac tggggtcctg    6720
aaagttgtta gcccttggga ttatgaagtt acatctgctt acaagctgac aataagagcc    6780
```

```
agcgacgccc ttactggtgc tagggctgaa gtcactgttg acttgctagt taatgatgta      6840
aatgacaacc cccctatttt cgatcagcct acatacaata caacactatc agaagcatct      6900
cttattggga cacctgtttt acaagttgtc tctattgatg cagactcaga aaacaataaa      6960
atggtacatt atcagattgt ccaggatacc tacaatagca cagattattt tcacatagat      7020
agctcaagtg gcttaatcct gacagcacga atgctggacc atgagttagt acaacactgc      7080
actttgaaag tcagatcaat agatagtggc ttcccatcac tgagcagtga ggttctcgtt      7140
catatctaca tctctgatgt aaatgacaac cctccagttt ttaatcagct catttatgag      7200
tcatatgtga gtgaattagc ccccgggc cattttgtaa cctgtgtaca agcctctgat      7260
gcagacagct ctgattttga ccggttggaa tatagcattt tatctgggaa tgaccggacg      7320
agctttctga tggacagcaa gagtggagtt atcacattgt ccaaccatcg gaagcagcgg      7380
atggagcctc tgtacagtct caatgtgtct gtctctgatg ggttgttcac cagcactgca      7440
caggtgcata ttagggtact tggggctaac ttgtacagcc ctgccttttc acaaagcaca      7500
tacgtagctg aggtgagaga gaacgtggct gcaggaacaa aggtaattca tgttcgagcc      7560
acagatggtg atccagggac ttatgggcag atcagctatg ccatcatcaa tgactttgcc      7620
aaggatcgat tcctcataga cagcaatggg caggtcatca ccacagaaag gctagaccgg      7680
gaaaaccctc tagaaggga tgttagtatt tttgtgaggg ccttgatgg tggagggaga      7740 acaactttct gcactgtgag agtgattgtt gtggatgaaa atgacaatgc tccccagttc      7800
atgacagtgg aatatagagc cagtgtcagg gcagatgttg gaaggggcca cttggtcact      7860
caagttcaag ccatagatcc cgatgatgga gcaaattcaa ggattactta ttccctctat      7920
agcgaggcct ctgtttcagt ggccgacctc ctggaaatcg atcctgacaa tggctggatg      7980
gtcacaaagg gtaattttaa ccagctgaaa aatacagtgc tttcgttctt tgtcaaagca      8040
gtagatgggg gcatcccagt aaagcactcc ctcattcctg tctatatcca cgtcttgccc      8100
cctgaaacgt tcttgccatc attcacccag tctcagtatt cctttaccat tgcagaagat      8160
acagccattg ggagtacagt ggacaccctg aggattttgc ccagtcagaa tgtctggttc      8220
agcacagtta atggggaacg gccagaaaat aacaaagggg gcgtattcgt catagaacag      8280
gaaacaggca ctattaagct tgacaaacgc cttgaccgtg aaaccagccc agctttccac      8340
tttaaagtag cagccactat acccctggac aaagtagaca ttgtgtttac tgtggatgta      8400
gatatcaagg tattggattt gaatgacaac aagccagtct ttgaaacttc aagctatgac      8460
accattataa tggaagggat gcctgttggc accaaactca cacaagtgag agctattgat      8520
atggactggg gagccaatgg acaagtcact tactccctcc actcggattc ccagcccgaa      8580
aaggtaatgg aagcattcaa tattgacagc aacacgggct ggatcagtac cttgaaggac      8640
ctagatcacg agacagaccc cacattcacc ttctctgtgg tggcctctga ccttggagag      8700
gcattctctc tttcctccac ggccttggtc tctgtcagag tgacagatat aaatgacaat      8760
gcaccagtct tcgcgcagga agtgtaccga gggaatgtga aggagagcga cccaccgggc      8820
gaggtggtag ccgtcctcag cacctgggac agagacacat ccgacgttaa tcgccaagtg      8880
agctaccata ttacaggagg aaaccctcga ggaaggtttg ctctgggcct ggtgcaaagt      8940
gagtggaagg tctatgtgaa gaggcctcta gacagagaag aacaggacat ttactttctc      9000
aatatcactg ccactgatgg gcttttttgtc acacaggcca tggtggaagt gagcgtcagt      9060
gatgtgaatg acaatagccc agtgtgtgat caggttgcat atacagcatt acttcctgaa      9120
gacattccat caaataaaat catcctgaaa gtcagtgcaa aggatgctga tattggatcc      9180
```

```
aatggatata tacgatactc actctatgga tctggaaaca gtgaatttt tctagatcca    9240
gaaagtggcg agttaaaaac cttggctctg ttggaccggg agaggatccc cgtgtacagc    9300
ctgatggcca aggccactga cggggtggc aggttctgcc agtccaacat ccacctaatc    9360
ctggaggatg tgaatgataa ccccctgtg ttttcttctg accactacaa cacctgtgtc    9420
tatgagaaca cagccaccaa ggctctgttg accagagttc aagccgtgga ccccgacatt    9480
ggcatcaata ggaaggtcgt gtactccctg gcagactcag ctggtggggt cttctccatt    9540
gacagctcat ctggcatcat catcctggag cagccactgg accgtgagca gcagtcttcg    9600
tacaacatca gcgtgcgggc cactgaccag agtcctggac agtccctgtc ctctctcact    9660
actgtcacca tcaccgttct ggacattaat gacaaccccc ctgtgtttga gaggagggac    9720
tacctggtga cggtgcctga ggacacctcc cctggcaccc aagtccttgc tgttttgcc    9780
accagcaaag atattggcac aaatgctgag atcacttatc tcatccggtc tgggaacgaa    9840
caagggaaat ttaagatcaa ccccaagaca gggggtattt ctgtctctga agtcctggac    9900
tatgaattat gcaaaaggtt ttacctggta gtggaagcca agatgggggg cacccccagct   9960
ctcagcgctg tggccactgt caacatcaac ctcacagatg ttaatgacaa ccctcccaag   10020
ttcagccaag acgtctacag tgcggttatc agtgaagacg ccttggtggg agactctgtc   10080
attttgctaa tagcagaaga tgtagacagc cagcccaacg gacagattca tttttccatt   10140
gtgaatggag atcgggacaa tgaattact gtagatcctg tcttgggact tgtgaaagtt   10200
aagaagaaat tggaccggga acgggtgtct ggatactctc tgcttgtcca ggccgtagac   10260
agtggcattc ctgcaatgtc atcaactgca actgtcaaca ttgatatttc tgatgtgaat   10320
gacaacagcc cggtgtttac acctgccaac tatactgctg tgattcagga aaataagcca   10380
gtgggcacca gcatcttgca gctggtggtg acagacagag actcctttca caatgggcct   10440
ccctttcat tctctatttt gtcgggaaat gaagaggagg agtttgtgtt ggaccctcat   10500
gggatcttgc ggtcggctgt ggtcttccag cacacagagt ctctggaata cgtgttgtgt   10560
gtccaggcaa aggattcagg caaaccccag caagtttctc acacttacat ccgcgtgcga   10620
gtcattgagg aaagcaccca aagcccaca gccattcccc tggaaattt cattgtcacc   10680
atggaggatg actttcctgg tggggtcatt gggaagattc atgccacaga tcaagacatg   10740
tatgatgtgc tcacatttgc cctgaaatcg gagcagaaaa gcttatttaa agtgaacagt   10800
cacgatggga aaatcatcgc cctggggaggc ctggacagcg gcaagtatgt cctgaatgtg   10860
tctgtgagtg atggtcgctt ccaggtaccc attgatgtgg tcgtgcatgt ggagcagttg   10920
gtgcatgaga tgctgcagaa cactgtcacc atccgctttg aaaatgtgtc ccctgaggac   10980
ttcgtggggc tgcacatgca tgggttccgg cgcaccctgc ggaatgcagt cctcacccag   11040
aagcaggaca gcctgcgcat catcagcatc cagcccgtgg caggcaccaa ccaactggac   11100
atgctgtttg cggtggagat gcacagcagc gagttctaca gccagcctta cctgatccag   11160
aagctgtcca atgctagaag acacctggag aatatcatgc gcatctcagc catcttggag   11220
aagaactgct cagggctgga ctgtcaggaa cagcattgtg agcaaggctt gtcactcgat   11280
tcccacgcgc tcatgaccta cagcacggct cgcatcagct ttgtgtgtcc gcgtttctac   11340
aggaacgtgc gttgcacctg caatggagga ctgtgtccgg ggtccaacga tccttgtgtg   11400
gagaagccgt gtccagggga catgcagtgt gtcggttatg aagccagcag agaccgttc   11460
ctctgccagt gtccaccagg gaagctcgga gagtgctcag ggcacacttc tctcagcttt   11520
```

```
gctggaaaca gttacatcaa atatcggctt tctgaaaata gcaaagaaga ggatttcaaa    11580
ctagctctgc gtcttcgaac actgcaaagc aatgggatta taatgtacac cagagcaaat    11640
ccctgcataa ttctgaagat tgtggatggc aagctgtggt tccagctgga ctgcggcagc    11700
ggccctggaa tcttgggcat ctcgggccgt gctgtcaacg acgggagctg gcactcggtc    11760
ttcctggagc tcaaccgcaa tttcacgagc ctgtccctgg atgacagcta cgtggagcgg    11820
cgccgggcgc ccctctactt ccagacgctg agcactgaga gtagcatcta cttcggcgcc    11880
ctggtgcaag cggataacat ccgcagcctg actgacacgc gggtcacgca ggtgctcagc    11940
ggcttccagg gctgcctgga ctcggtgata ctgaataaca atgagctgcc gctgcagaac    12000
aagcgcagca gcttcgcgga ggtggtgggc ctgacggagc tgaagctggg ctgcgtgctc    12060
tatcccgacg cctgcaagcg cagcccgtgc cagcacgggg gcagctgcac tggcctgcca    12120
tcggggggct atcagtgtac ctgtctctca cagtttacgg ggagaaactg tgaatctgag    12180
attacagcct gcttcccaaa cccctgccgg aatggaggat cctgcgatcc aataggaaac    12240
actttcatct gcaattgtaa agctgggctc actggagtca cgtgtgagga ggacatcaat    12300
gagtgcgaac gagaggagtg tgagaacgga ggctcctgcg tgaacgtgtt cggctccttc    12360
ctctgcaact gcacgccggg ctacgtgggc cagtactgcg ggctgcgccc cgtggtggta    12420
cccaatatcc aggctggcca ctcctacgtg gggaaggagg agctcatcgg catcgccgtg    12480
gtcctcttcg tcatcttcat cctggtggtt ctcttcatag tcttccgcaa gaaggtcttc    12540
cgcaagaact actcccgcaa caacatcacg ctagtgcagg acccggccac cgccgccctg    12600
cttaacaaga gcaatggcat cccgttccgg aacctgcgcg gcagtgggga cggccgcaac    12660
gtctaccagg aggtggggcc cccgcaggtc ccgtgcgcc ccatggccta cacaccctgc    12720
ttccagagtg actccaggag caacctggat aagatcgtgg acgggctggg aggcgagcac    12780
caggaaatga ccacgtttca ccctgagtcg ccccgcatcc tgacagcccg gcggggcgtg    12840
gtcgtgtgca gtgtggcccc caacctcccc gccgtgtcac cctgccgctc cgactgcgac    12900
tccatccgga gaatggctg ggacgcggga actgagaaca aggggttga tgacccggga    12960 gaagtgacct gctttgcagg tagtaataaa ggcagcaact ctgaagttca gtccctcagc    13020
tccttccagt cagattctgg tgacgacaat gcctccatag tgactgtcat tcagcttgtc    13080
aacaatgtag ttgacactat agagaatgaa gtgtctgtca tggaccaagg acagaactac    13140
aaccgagcct atcactggga cacctctgat tggatgccag gggccgcct gtcggacata    13200 gaggaagtgc ccaactatga gaaccaggat ggagggtctg cacaccaggg gagcacacgg    13260
gagctggaga gcgattacta cctgggtggt tatgacattg acagtgaata cccaccccct    13320
catgaagagg agttcttgag tcaggaccag ctgcctcctc ctctcccgga ggacttccca    13380
gaccaatatg aggccctgcc accctcccag cctgtctccc tggccagcac actgagccca    13440
gactgcagga gaaggcccca gtttcatcct agccagtatc tccctcctca cccattcccc    13500
aacgaaacgg atttggtggg cccgcctgcc agctgtgaat ttagtacttt tgctgtgagc    13560
atgaaccagg gcacagagcc cacaggccca gcagacagcc tgtctctgtc cttgcacaat    13620
tccagaggca cctcatcctc ggatgtgtct gccaactgcg gctttgacga ttccgaagta    13680
gccatgagtg actacgagag cgtggagag ctcagcctcg ccagccttca cattcccttt    13740
gtggagactc agcatcagac tcaagtgtag                                    13770
```

<210> SEQ ID NO 2
<211> LENGTH: 4589

```
<212> TYPE: PRT
<213> ORGANISM: homo sapiens

<400> SEQUENCE: 2

Met Asp Ile Ile Met Gly His Cys Val Gly Thr Arg Pro Pro Ala Cys
 1               5                  10                  15

Cys Leu Ile Leu Leu Leu Phe Lys Leu Leu Ala Thr Val Ser Gln Gly
                20                  25                  30

Leu Pro Gly Thr Gly Pro Leu Gly Phe His Phe Thr His Ser Ile Tyr
            35                  40                  45

Asn Ala Thr Val Tyr Glu Asn Ser Ala Ala Arg Thr Tyr Val Asn Ser
        50                  55                  60

Gln Ser Arg Met Gly Ile Thr Leu Ile Asp Leu Ser Trp Asp Ile Lys
65                  70                  75                  80

Tyr Arg Ile Val Ser Gly Asp Glu Glu Gly Phe Phe Lys Ala Glu Glu
                85                  90                  95

Val Ile Ile Ala Asp Phe Cys Phe Leu Arg Ile Arg Thr Lys Gly Gly
               100                 105                 110

Asn Ser Ala Ile Leu Asn Arg Glu Ile Gln Asp Asn Tyr Leu Leu Ile
               115                 120                 125

Val Lys Gly Ser Val Arg Gly Glu Asp Leu Glu Ala Trp Thr Lys Val
130                 135                 140

Asn Ile Gln Val Leu Asp Met Asn Asp Leu Arg Pro Leu Phe Ser Pro
145                 150                 155                 160

Thr Thr Tyr Ser Val Thr Ile Ala Glu Ser Thr Pro Leu Arg Thr Ser
                165                 170                 175

Val Ala Gln Val Thr Ala Thr Asp Ala Asp Ile Gly Ser Asn Gly Glu
            180                 185                 190

Phe Tyr Tyr Tyr Phe Lys Asn Lys Val Asp Leu Phe Ser Val His Pro
        195                 200                 205

Thr Ser Gly Val Ile Ser Leu Ser Gly Arg Leu Asn Tyr Asp Glu Lys
    210                 215                 220

Asn Arg Tyr Asp Leu Glu Ile Leu Ala Val Asp Arg Gly Met Lys Leu
225                 230                 235                 240

Tyr Gly Asn Asn Gly Val Ser Ser Thr Ala Lys Leu Tyr Val His Ile
                245                 250                 255

Glu Arg Ile Asn Glu His Ala Pro Thr Ile His Val Thr His Val
            260                 265                 270

Pro Phe Ser Leu Glu Lys Glu Pro Thr Tyr Ala Val Val Thr Val Asp
        275                 280                 285

Asp Leu Asp Asp Gly Ala Asn Gly Glu Ile Glu Ser Val Ser Ile Val
    290                 295                 300

Ala Gly Asp Pro Leu Asp Gln Phe Phe Leu Ala Lys Glu Gly Lys Trp
305                 310                 315                 320

Leu Asn Glu Tyr Lys Ile Lys Glu Arg Lys Gln Ile Asp Trp Glu Ser
                325                 330                 335

Phe Pro Tyr Gly Tyr Asn Leu Thr Leu Gln Ala Lys Asp Lys Gly Ser
            340                 345                 350

Pro Gln Lys Cys Ser Ala Leu Lys Ala Val Tyr Ile Gly Asn Pro Thr
        355                 360                 365

Arg Asp Thr Val Pro Ile Arg Phe Glu Lys Glu Val Tyr Asp Val Ser
    370                 375                 380

Ile Ser Glu Phe Ser Pro Pro Gly Val Val Val Ala Ile Val Lys Leu
385                 390                 395                 400
```

```
Ser Pro Glu Pro Ile Asp Val Glu Tyr Lys Leu Ser Pro Gly Glu Asp
            405                 410                 415

Ala Val Tyr Phe Lys Ile Asn Pro Arg Ser Gly Leu Ile Val Thr Ala
        420                 425                 430

Arg Pro Leu Asn Thr Val Lys Lys Glu Val Tyr Lys Leu Glu Val Thr
            435                 440                 445

Asn Lys Glu Gly Asp Leu Lys Ala Gln Val Thr Ile Ser Ile Glu Asp
450                 455                 460

Ala Asn Asp His Thr Pro Glu Phe Gln Gln Pro Leu Tyr Asp Ala Tyr
465                 470                 475                 480

Val Asn Glu Ser Val Pro Val Gly Thr Ser Val Leu Thr Val Ser Ala
            485                 490                 495

Ser Asp Lys Asp Lys Gly Glu Asn Gly Tyr Ile Thr Tyr Ser Ile Ala
            500                 505                 510

Ser Leu Asn Leu Leu Pro Phe Val Ile Asn Gln Phe Thr Gly Val Ile
        515                 520                 525

Ser Thr Thr Glu Glu Leu Asp Phe Glu Ser Ser Pro Glu Ile Tyr Arg
    530                 535                 540

Phe Ile Val Arg Ala Ser Asp Trp Gly Ser Pro Tyr Arg His Glu Ser
545                 550                 555                 560

Glu Val Asn Val Thr Ile Arg Ile Gly Asn Val Asn Asp Asn Ser Pro
            565                 570                 575

Leu Phe Glu Lys Val Ala Cys Gln Gly Val Ile Ser Tyr Asp Phe Pro
        580                 585                 590

Val Gly Gly His Ile Thr Ala Val Ser Ala Ile Asp Ile Asp Glu Leu
    595                 600                 605

Glu Leu Val Lys Tyr Lys Ile Ile Ser Gly Asn Glu Leu Gly Phe Phe
        610                 615                 620

Tyr Leu Asn Pro Asp Ser Gly Val Leu Gln Leu Lys Lys Ser Leu Thr
625                 630                 635                 640

Asn Ser Gly Ile Lys Asn Gly Asn Phe Ala Leu Arg Ile Thr Ala Thr
            645                 650                 655

Asp Gly Glu Asn Leu Ala Asp Pro Met Ser Ile Asn Ile Ser Val Leu
            660                 665                 670

His Gly Lys Val Ser Ser Lys Ser Phe Ser Cys Arg Glu Thr Arg Val
        675                 680                 685

Ala Gln Lys Leu Ala Glu Lys Leu Leu Ile Lys Ala Lys Ala Asn Gly
        690                 695                 700

Lys Leu Asn Leu Glu Asp Gly Phe Leu Asp Phe Tyr Ser Ile Asn Arg
705                 710                 715                 720

Gln Gly Pro Tyr Phe Asp Lys Ser Phe Pro Ser Asp Val Ala Val Lys
            725                 730                 735

Glu Asp Leu Pro Val Gly Ala Asn Ile Leu Lys Ile Lys Ala Tyr Asp
            740                 745                 750

Ala Asp Ser Gly Phe Asn Gly Lys Val Leu Phe Thr Ile Ser Asp Gly
            755                 760                 765

Asn Thr Asp Ser Cys Phe Asn Ile Asp Met Glu Thr Gly Gln Leu Lys
    770                 775                 780

Val Leu Met Pro Met Asp Arg Glu His Thr Asp Leu Tyr Leu Leu Asn
785                 790                 795                 800

Ile Thr Ile Tyr Asp Leu Gly Asn Pro Gln Lys Ser Ser Trp Arg Leu
            805                 810                 815
```

-continued

```
Leu Thr Ile Asn Val Glu Asp Ala Asn Asp Asn Ser Pro Val Phe Ile
            820                 825                 830

Gln Asp Ser Tyr Ser Val Asn Ile Leu Glu Ser Ser Gly Ile Gly Thr
        835                 840                 845

Glu Ile Ile Gln Val Glu Ala Arg Asp Lys Asp Leu Gly Ser Asn Gly
    850                 855                 860

Glu Val Thr Tyr Ser Val Leu Thr Asp Thr Gln Gln Phe Ala Ile Asn
865                 870                 875                 880

Ser Ser Thr Gly Ile Val Tyr Val Ala Asp Gln Leu Asp Arg Glu Ser
                885                 890                 895

Lys Ala Asn Tyr Ser Leu Lys Ile Glu Ala Arg Asp Lys Ala Glu Ser
            900                 905                 910

Gly Gln Gln Leu Phe Ser Val Val Thr Leu Lys Val Phe Leu Asp Asp
        915                 920                 925

Val Asn Asp Cys Ser Pro Ala Phe Ile Pro Ser Ser Tyr Ser Val Lys
    930                 935                 940

Val Leu Glu Asp Leu Pro Val Gly Thr Val Ile Ala Trp Leu Glu Thr
945                 950                 955                 960

His Asp Pro Asp Leu Gly Leu Gly Gly Gln Val Arg Tyr Ser Leu Val
                965                 970                 975

Asn Asp Tyr Asn Gly Arg Phe Glu Ile Asp Lys Ala Ser Gly Ala Ile
            980                 985                 990

Arg Leu Ser Lys Glu Leu Asp Tyr Glu Lys Gln Gln Phe Tyr Asn Leu
        995                 1000                1005

Thr Val Arg Ala Lys Asp Lys Gly Arg Pro Val Ser Leu Ser Ser Val
    1010                1015                1020

Ser Phe Val Glu Val Glu Val Val Asp Val Asn Glu Asn Leu His Thr
1025                1030                1035                1040

Pro Tyr Phe Pro Asp Phe Ala Val Val Gly Ser Val Lys Glu Asn Ser
                1045                1050                1055

Arg Ile Gly Thr Ser Val Leu Gln Val Thr Ala Arg Asp Glu Asp Ser
            1060                1065                1070

Gly Arg Asp Gly Glu Ile Gln Tyr Ser Ile Arg Asp Gly Ser Gly Leu
        1075                1080                1085

Gly Arg Phe Ser Ile Asp Asp Glu Ser Gly Val Ile Thr Ala Ala Asp
    1090                1095                1100

Ile Leu Asp Arg Glu Thr Met Gly Ser Tyr Trp Leu Thr Val Tyr Ala
1105                1110                1115                1120

Thr Asp Arg Gly Val Val Pro Leu Tyr Ser Thr Ile Glu Val Tyr Ile
                1125                1130                1135

Glu Val Glu Asp Val Asn Asp Asn Ala Pro Leu Thr Ser Glu Pro Ile
            1140                1145                1150

Tyr Tyr Pro Val Val Met Glu Asn Ser Pro Lys Asp Val Ser Val Ile
        1155                1160                1165

Gln Ile Gln Ala Glu Asp Pro Asp Ser Ser Asn Glu Lys Leu Thr
    1170                1175                1180

Tyr Arg Ile Thr Ser Gly Asn Pro Gln Asn Phe Phe Ala Ile Asn Ile
1185                1190                1195                1200

Lys Thr Gly Leu Ile Thr Thr Thr Ser Arg Lys Leu Asp Arg Glu Gln
                1205                1210                1215

Gln Ala Glu His Phe Leu Glu Val Thr Val Thr Asp Gly Gly Pro Ser
            1220                1225                1230

Pro Lys Gln Ser Thr Ile Trp Val Val Gln Val Leu Asp Glu Asn
```

```
                    1235                1240                1245
Asp Asn Lys Pro Gln Phe Pro Glu Lys Val Tyr Gln Ile Lys Leu Pro
    1250                1255                1260
Glu Arg Asp Arg Lys Lys Arg Gly Glu Pro Ile Tyr Arg Ala Phe Ala
1265                1270                1275                1280
Phe Asp Arg Asp Glu Gly Pro Asn Ala Glu Ile Ser Tyr Ser Ile Val
                1285                1290                1295
Asp Gly Asn Asp Asp Gly Lys Phe Phe Ile Asp Pro Lys Thr Gly Met
            1300                1305                1310
Val Ser Ser Arg Lys Gln Phe Thr Ala Gly Ser Tyr Asp Ile Leu Thr
        1315                1320                1325
Ile Lys Ala Val Asp Asn Gly Arg Pro Gln Lys Ser Ser Thr Ala Arg
    1330                1335                1340
Leu His Ile Glu Trp Ile Lys Lys Pro Pro Ser Pro Ile Pro Leu
1345                1350                1355                1360
Thr Phe Asp Glu Pro Phe Tyr Asn Phe Thr Val Met Glu Ser Asp Arg
                1365                1370                1375
Val Thr Glu Ile Val Gly Val Val Ser Val Gln Pro Ala Asn Thr Pro
            1380                1385                1390
Leu Trp Phe Asp Ile Val Gly Gly Asn Phe Asp Ser Ala Phe Asp Ala
        1395                1400                1405
Glu Lys Gly Val Gly Thr Ile Val Ile Ala Lys Pro Leu Asp Ala Glu
    1410                1415                1420
Gln Arg Ser Ile Tyr Asn Met Ser Val Glu Val Thr Asp Gly Thr Asn
1425                1430                1435                1440
Val Ala Val Thr Gln Val Phe Ile Lys Val Leu Asp Asn Asn Asp Asn
                1445                1450                1455
Gly Pro Glu Phe Ser Gln Pro Asn Tyr Asp Val Thr Ile Ser Glu Asp
            1460                1465                1470
Val Leu Pro Asp Thr Glu Ile Leu Gln Ile Glu Ala Thr Asp Arg Asp
        1475                1480                1485
Glu Lys His Lys Leu Ser Tyr Thr Val His Ser Ser Ile Asp Ser Ile
    1490                1495                1500
Ser Met Arg Lys Phe Arg Ile Asp Pro Ser Thr Gly Val Leu Tyr Thr
1505                1510                1515                1520
Ala Glu Arg Leu Asp His Glu Ala Gln Asp Lys His Ile Leu Asn Ile
                1525                1530                1535
Met Val Arg Asp Gln Gly Phe Pro Tyr Arg Arg Asn Leu Ala Arg Val
            1540                1545                1550
Ile Val Asn Val Glu Asp Ala Asn Asp His Ser Pro Tyr Phe Thr Asn
        1555                1560                1565
Pro Leu Tyr Glu Ala Ser Val Phe Glu Ser Ala Ala Leu Gly Ser Ala
    1570                1575                1580
Val Leu Gln Val Thr Ala Leu Asp Lys Asp Lys Gly Glu Asn Ala Glu
1585                1590                1595                1600
Leu Ile Tyr Thr Ile Glu Ala Gly Asn Thr Gly Asn Met Phe Lys Ile
                1605                1610                1615
Glu Pro Val Leu Gly Ile Ile Thr Ile Cys Lys Glu Pro Asp Met Thr
            1620                1625                1630
Thr Met Gly Gln Phe Val Leu Ser Ile Lys Val Thr Asp Gln Gly Ser
        1635                1640                1645
Pro Pro Met Ser Ala Thr Ala Ile Val Arg Ile Ser Val Thr Met Ser
    1650                1655                1660
```

-continued

```
Asp Asn Ser His Pro Lys Phe Ile His Lys Asp Tyr Gln Ala Glu Val
1665                1670                1675                1680

Asn Glu Asn Val Asp Ile Gly Thr Ser Val Ile Leu Ile Ser Ala Ile
            1685                1690                1695

Ser Gln Ser Thr Leu Ile Tyr Glu Val Lys Asp Gly Asp Ile Asn Gly
            1700                1705                1710

Ile Phe Thr Ile Asn Pro Tyr Ser Gly Val Ile Thr Thr Gln Lys Ala
            1715                1720                1725

Leu Asp Tyr Glu Arg Thr Ser Ser Tyr Gln Leu Ile Ile Gln Ala Thr
            1730                1735                1740

Asn Met Ala Gly Met Ala Ser Asn Ala Thr Val Asn Ile Gln Ile Val
1745                1750                1755                1760

Asp Glu Asn Asp Asn Ala Pro Val Phe Leu Phe Ser Gln Tyr Ser Gly
            1765                1770                1775

Ser Leu Ser Glu Ala Ala Pro Ile Asn Ser Ile Val Arg Ser Leu Asp
            1780                1785                1790

Asn Ser Pro Leu Val Ile Arg Ala Thr Asp Ala Asp Ser Asn Arg Asn
            1795                1800                1805

Ala Leu Leu Val Tyr Gln Ile Val Glu Ser Thr Ala Lys Lys Phe Phe
            1810                1815                1820

Thr Val Asp Ser Ser Thr Gly Ala Ile Arg Thr Ile Ala Asn Leu Asp
1825                1830                1835                1840

His Glu Thr Ile Ala His Phe His Phe His Val His Val Arg Asp Ser
            1845                1850                1855

Gly Ser Pro Gln Leu Thr Ala Glu Ser Pro Val Glu Val Asn Ile Glu
            1860                1865                1870

Val Thr Asp Val Asn Asp Asn Pro Pro Val Phe Thr Gln Ala Val Phe
            1875                1880                1885

Glu Thr Ile Leu Leu Leu Pro Thr Tyr Val Gly Val Glu Val Leu Lys
            1890                1895                1900

Val Ser Ala Thr Asp Pro Asp Ser Glu Val Pro Pro Glu Leu Thr Tyr
1905                1910                1915                1920

Ser Leu Met Glu Gly Ser Leu Asp His Phe Leu Ile Asp Ser Asn Ser
            1925                1930                1935

Gly Val Leu Thr Ile Lys Asn Asn Asn Leu Ser Lys Asp His Tyr Met
            1940                1945                1950

Leu Ile Val Lys Val Ser Asp Gly Lys Phe Tyr Ser Thr Ser Met Val
            1955                1960                1965

Thr Ile Met Val Lys Glu Ala Met Asp Ser Gly Leu His Phe Thr Gln
1970                1975                1980

Ser Phe Tyr Ser Thr Ser Ile Ser Glu Asn Asn Thr Asn Ile Thr Lys
1985                1990                1995                2000

Val Ala Ile Val Asn Ala Val Gly Asn Arg Leu Asn Glu Pro Leu Lys
            2005                2010                2015

Tyr Ser Ile Leu Asn Pro Gly Asn Lys Phe Lys Ile Lys Ser Thr Ser
            2020                2025                2030

Gly Val Ile Gln Thr Thr Gly Val Pro Phe Asp Arg Glu Glu Gln Glu
            2035                2040                2045

Leu Tyr Glu Leu Val Val Glu Ala Ser Arg Glu Leu Asp His Leu Arg
            2050                2055                2060

Val Ala Arg Val Val Arg Val Asn Ile Glu Asp Ile Asn Asp Asn
2065                2070                2075                2080
```

-continued

```
Ser Pro Val Phe Val Gly Leu Pro Tyr Tyr Ala Ala Val Gln Val Asp
            2085                2090                2095

Ala Glu Pro Gly Thr Leu Ile Tyr Gln Val Thr Ala Ile Asp Lys Asp
            2100                2105                2110

Lys Gly Pro Asn Gly Glu Val Thr Tyr Val Leu Gln Asp Asp Tyr Gly
            2115                2120                2125

His Phe Glu Ile Asn Pro Asn Ser Gly Asn Val Ile Leu Lys Glu Ala
            2130                2135                2140

Phe Asn Ser Asp Leu Ser Asn Ile Glu Tyr Gly Val Thr Ile Leu Ala
2145                2150                2155                2160

Lys Asp Gly Gly Lys Pro Ser Leu Ser Thr Ser Val Glu Leu Pro Ile
            2165                2170                2175

Thr Ile Val Asn Lys Ala Met Pro Val Phe Asp Lys Pro Phe Tyr Thr
            2180                2185                2190

Ala Ser Val Asn Glu Asp Ile Arg Met Asn Thr Pro Ile Leu Ser Ile
            2195                2200                2205

Asn Ala Thr Ser Pro Glu Gly Gln Gly Ile Ile Tyr Ile Ile Ile Asp
            2210                2215                2220

Gly Asp Pro Phe Lys Gln Phe Asn Ile Asp Phe Asp Thr Gly Val Leu
2225                2230                2235                2240

Lys Val Val Ser Pro Leu Asp Tyr Glu Val Thr Ser Ala Tyr Lys Leu
            2245                2250                2255

Thr Ile Arg Ala Ser Asp Ala Leu Thr Gly Ala Arg Ala Glu Val Thr
            2260                2265                2270

Val Asp Leu Leu Val Asn Asp Val Asn Asp Asn Pro Pro Ile Phe Asp
            2275                2280                2285

Gln Pro Thr Tyr Asn Thr Thr Leu Ser Glu Ala Ser Leu Ile Gly Thr
            2290                2295                2300

Pro Val Leu Gln Val Val Ser Ile Asp Ala Asp Ser Glu Asn Asn Lys
2305                2310                2315                2320

Met Val His Tyr Gln Ile Val Gln Asp Thr Tyr Asn Ser Thr Asp Tyr
            2325                2330                2335

Phe His Ile Asp Ser Ser Ser Gly Leu Ile Leu Thr Ala Arg Met Leu
            2340                2345                2350

Asp His Glu Leu Val Gln His Cys Thr Leu Lys Val Arg Ser Ile Asp
            2355                2360                2365

Ser Gly Phe Pro Ser Leu Ser Ser Glu Val Leu Val His Ile Tyr Ile
            2370                2375                2380

Ser Asp Val Asn Asp Asn Pro Pro Val Phe Asn Gln Leu Ile Tyr Glu
2385                2390                2395                2400

Ser Tyr Val Ser Glu Leu Ala Pro Arg Gly His Phe Val Thr Cys Val
            2405                2410                2415

Gln Ala Ser Asp Ala Asp Ser Ser Asp Phe Asp Arg Leu Glu Tyr Ser
            2420                2425                2430

Ile Leu Ser Gly Asn Asp Arg Thr Ser Phe Leu Met Asp Ser Lys Ser
            2435                2440                2445

Gly Val Ile Thr Leu Ser Asn His Arg Lys Gln Arg Met Glu Pro Leu
            2450                2455                2460

Tyr Ser Leu Asn Val Ser Val Ser Asp Gly Leu Phe Thr Ser Thr Ala
2465                2470                2475                2480

Gln Val His Ile Arg Val Leu Gly Ala Asn Leu Tyr Ser Pro Ala Phe
            2485                2490                2495

Ser Gln Ser Thr Tyr Val Ala Glu Val Arg Glu Asn Val Ala Ala Gly
```

-continued

```
                2500            2505            2510
Thr Lys Val Ile His Val Arg Ala Thr Asp Gly Asp Pro Gly Thr Tyr
        2515            2520            2525
Gly Gln Ile Ser Tyr Ala Ile Ile Asn Asp Phe Ala Lys Asp Arg Phe
        2530            2535            2540
Leu Ile Asp Ser Asn Gly Gln Val Ile Thr Thr Glu Arg Leu Asp Arg
2545            2550            2555            2560
Glu Asn Pro Leu Glu Gly Asp Val Ser Ile Phe Val Arg Ala Leu Asp
                2565            2570            2575
Gly Gly Gly Arg Thr Thr Phe Cys Thr Val Arg Val Ile Val Val Asp
        2580            2585            2590
Glu Asn Asp Asn Ala Pro Gln Phe Met Thr Val Glu Tyr Arg Ala Ser
        2595            2600            2605
Val Arg Ala Asp Val Gly Arg Gly His Leu Val Thr Gln Val Gln Ala
        2610            2615            2620
Ile Asp Pro Asp Asp Gly Ala Asn Ser Arg Ile Thr Tyr Ser Leu Tyr
2625            2630            2635            2640
Ser Glu Ala Ser Val Ser Val Ala Asp Leu Leu Glu Ile Asp Pro Asp
                2645            2650            2655
Asn Gly Trp Met Val Thr Lys Gly Asn Phe Asn Gln Leu Lys Asn Thr
        2660            2665            2670
Val Leu Ser Phe Phe Val Lys Ala Val Asp Gly Gly Ile Pro Val Lys
        2675            2680            2685
His Ser Leu Ile Pro Val Tyr Ile His Val Leu Pro Pro Glu Thr Phe
        2690            2695            2700
Leu Pro Ser Phe Thr Gln Ser Gln Tyr Ser Phe Thr Ile Ala Glu Asp
2705            2710            2715            2720
Thr Ala Ile Gly Ser Thr Val Asp Thr Leu Arg Ile Leu Pro Ser Gln
                2725            2730            2735
Asn Val Trp Phe Ser Thr Val Asn Gly Glu Arg Pro Glu Asn Asn Lys
        2740            2745            2750
Gly Gly Val Phe Val Ile Glu Gln Glu Thr Gly Thr Ile Lys Leu Asp
        2755            2760            2765
Lys Arg Leu Asp Arg Glu Thr Ser Pro Ala Phe His Phe Lys Val Ala
        2770            2775            2780
Ala Thr Ile Pro Leu Asp Lys Val Asp Ile Val Phe Thr Val Asp Val
2785            2790            2795            2800
Asp Ile Lys Val Leu Asp Leu Asn Asp Asn Lys Pro Val Phe Glu Thr
                2805            2810            2815
Ser Ser Tyr Asp Thr Ile Ile Met Glu Gly Met Pro Gly Thr Lys
        2820            2825            2830
Leu Thr Gln Val Arg Ala Ile Asp Met Asp Trp Gly Ala Asn Gly Gln
        2835            2840            2845
Val Thr Tyr Ser Leu His Ser Asp Ser Gln Pro Glu Lys Val Met Glu
        2850            2855            2860
Ala Phe Asn Ile Asp Ser Asn Thr Gly Trp Ile Ser Thr Leu Lys Asp
2865            2870            2875            2880
Leu Asp His Glu Thr Asp Pro Thr Phe Thr Phe Ser Val Val Ala Ser
                2885            2890            2895
Asp Leu Gly Glu Ala Phe Ser Leu Ser Ser Thr Ala Leu Val Ser Val
        2900            2905            2910
Arg Val Thr Asp Ile Asn Asp Asn Ala Pro Val Phe Ala Gln Glu Val
        2915            2920            2925
```

-continued

Tyr Arg Gly Asn Val Lys Glu Ser Asp Pro Gly Glu Val Val Ala
    2930                2935                2940

Val Leu Ser Thr Trp Asp Arg Asp Thr Ser Asp Val Asn Arg Gln Val
2945                2950                2955                2960

Ser Tyr His Ile Thr Gly Gly Asn Pro Arg Gly Arg Phe Ala Leu Gly
            2965                2970                2975

Leu Val Gln Ser Glu Trp Lys Val Tyr Val Lys Arg Pro Leu Asp Arg
        2980                2985                2990

Glu Glu Gln Asp Ile Tyr Phe Leu Asn Ile Thr Ala Thr Asp Gly Leu
    2995                3000                3005

Phe Val Thr Gln Ala Met Val Glu Val Ser Val Ser Asp Val Asn Asp
    3010                3015                3020

Asn Ser Pro Val Cys Asp Gln Val Ala Tyr Thr Ala Leu Leu Pro Glu
3025                3030                3035                3040

Asp Ile Pro Ser Asn Lys Ile Ile Leu Lys Val Ser Ala Lys Asp Ala
            3045                3050                3055

Asp Ile Gly Ser Asn Gly Tyr Ile Arg Tyr Ser Leu Tyr Gly Ser Gly
        3060                3065                3070

Asn Ser Glu Phe Phe Leu Asp Pro Glu Ser Gly Glu Leu Lys Thr Leu
        3075                3080                3085

Ala Leu Leu Asp Arg Glu Arg Ile Pro Val Tyr Ser Leu Met Ala Lys
    3090                3095                3100

Ala Thr Asp Gly Gly Gly Arg Phe Cys Gln Ser Asn Ile His Leu Ile
3105                3110                3115                3120

Leu Glu Asp Val Asn Asp Asn Pro Pro Val Phe Ser Ser Asp His Tyr
            3125                3130                3135

Asn Thr Cys Val Tyr Glu Asn Thr Ala Thr Lys Ala Leu Leu Thr Arg
        3140                3145                3150

Val Gln Ala Val Asp Pro Asp Ile Gly Ile Asn Arg Lys Val Val Tyr
        3155                3160                3165

Ser Leu Ala Asp Ser Ala Gly Gly Val Phe Ser Ile Asp Ser Ser Ser
    3170                3175                3180

Gly Ile Ile Ile Leu Glu Gln Pro Leu Asp Arg Glu Gln Gln Ser Ser
3185                3190                3195                3200

Tyr Asn Ile Ser Val Arg Ala Thr Asp Gln Ser Pro Gly Gln Ser Leu
            3205                3210                3215

Ser Ser Leu Thr Thr Val Thr Ile Thr Val Leu Asp Ile Asn Asp Asn
        3220                3225                3230

Pro Pro Val Phe Glu Arg Arg Asp Tyr Leu Val Thr Val Pro Glu Asp
        3235                3240                3245

Thr Ser Pro Gly Thr Gln Val Leu Ala Val Phe Ala Thr Ser Lys Asp
    3250                3255                3260

Ile Gly Thr Asn Ala Glu Ile Thr Tyr Leu Ile Arg Ser Gly Asn Glu
3265                3270                3275                3280

Gln Gly Lys Phe Lys Ile Asn Pro Lys Thr Gly Gly Ile Ser Val Ser
            3285                3290                3295

Glu Val Leu Asp Tyr Glu Leu Cys Lys Arg Phe Tyr Leu Val Val Glu
        3300                3305                3310

Ala Lys Asp Gly Gly Thr Pro Ala Leu Ser Ala Val Ala Thr Val Asn
    3315                3320                3325

Ile Asn Leu Thr Asp Val Asn Asp Asn Pro Pro Lys Phe Ser Gln Asp
    3330                3335                3340

-continued

```
Val Tyr Ser Ala Val Ile Ser Glu Asp Ala Leu Val Gly Asp Ser Val
3345                3350                3355                3360

Ile Leu Leu Ile Ala Glu Asp Val Asp Ser Gln Pro Asn Gly Gln Ile
            3365                3370                3375

His Phe Ser Ile Val Asn Gly Asp Arg Asp Asn Glu Phe Thr Val Asp
        3380                3385                3390

Pro Val Leu Gly Leu Val Lys Val Lys Lys Leu Asp Arg Glu Arg
    3395                3400                3405

Val Ser Gly Tyr Ser Leu Leu Val Gln Ala Val Asp Ser Gly Ile Pro
    3410                3415                3420

Ala Met Ser Ser Thr Ala Thr Val Asn Ile Asp Ile Ser Asp Val Asn
3425                3430                3435                3440

Asp Asn Ser Pro Val Phe Thr Pro Ala Asn Tyr Thr Ala Val Ile Gln
            3445                3450                3455

Glu Asn Lys Pro Val Gly Thr Ser Ile Leu Gln Leu Val Val Thr Asp
            3460                3465                3470

Arg Asp Ser Phe His Asn Gly Pro Pro Phe Ser Phe Ser Ile Leu Ser
    3475                3480                3485

Gly Asn Glu Glu Glu Phe Val Leu Asp Pro His Gly Ile Leu Arg
    3490                3495                3500

Ser Ala Val Val Phe Gln His Thr Glu Ser Leu Glu Tyr Val Leu Cys
3505                3510                3515                3520

Val Gln Ala Lys Asp Ser Gly Lys Pro Gln Gln Val Ser His Thr Tyr
            3525                3530                3535

Ile Arg Val Arg Val Ile Glu Glu Ser Thr His Lys Pro Thr Ala Ile
            3540                3545                3550

Pro Leu Glu Ile Phe Ile Val Thr Met Glu Asp Asp Phe Pro Gly Gly
    3555                3560                3565

Val Ile Gly Lys Ile His Ala Thr Asp Gln Asp Met Tyr Asp Val Leu
    3570                3575                3580

Thr Phe Ala Leu Lys Ser Glu Gln Lys Ser Leu Phe Lys Val Asn Ser
3585                3590                3595                3600

His Asp Gly Lys Ile Ile Ala Leu Gly Gly Leu Asp Ser Gly Lys Tyr
            3605                3610                3615

Val Leu Asn Val Ser Val Ser Asp Gly Arg Phe Gln Val Pro Ile Asp
            3620                3625                3630

Val Val His Val Glu Gln Leu Val His Glu Met Leu Gln Asn Thr
    3635                3640                3645

Val Thr Ile Arg Phe Glu Asn Val Ser Pro Glu Asp Phe Val Gly Leu
    3650                3655                3660

His Met His Gly Phe Arg Arg Thr Leu Arg Asn Ala Val Leu Thr Gln
3665                3670                3675                3680

Lys Gln Asp Ser Leu Arg Ile Ile Ser Ile Gln Pro Val Ala Gly Thr
            3685                3690                3695

Asn Gln Leu Asp Met Leu Phe Ala Val Glu Met His Ser Ser Glu Phe
            3700                3705                3710

Tyr Lys Pro Ala Tyr Leu Ile Gln Lys Leu Ser Asn Ala Arg Arg His
            3715                3720                3725

Leu Glu Asn Ile Met Arg Ile Ser Ala Ile Leu Glu Lys Asn Cys Ser
    3730                3735                3740

Gly Leu Asp Cys Gln Glu Gln His Cys Glu Gln Gly Leu Ser Leu Asp
3745                3750                3755                3760

Ser His Ala Leu Met Thr Tyr Ser Thr Ala Arg Ile Ser Phe Val Cys
```

-continued

```
                   3765                3770                3775
Pro Arg Phe Tyr Arg Asn Val Arg Cys Thr Cys Asn Gly Gly Leu Cys
            3780                3785                3790
Pro Gly Ser Asn Asp Pro Cys Val Glu Lys Pro Cys Pro Gly Asp Met
            3795                3800                3805
Gln Cys Val Gly Tyr Glu Ala Ser Arg Arg Pro Phe Leu Cys Gln Cys
            3810                3815                3820
Pro Pro Gly Lys Leu Gly Glu Cys Ser Gly His Thr Ser Leu Ser Phe
3825                3830                3835                3840
Ala Gly Asn Ser Tyr Ile Lys Tyr Arg Leu Ser Glu Asn Ser Lys Glu
            3845                3850                3855
Glu Asp Phe Lys Leu Ala Leu Arg Leu Arg Thr Leu Gln Ser Asn Gly
            3860                3865                3870
Ile Ile Met Tyr Thr Arg Ala Asn Pro Cys Ile Ile Leu Lys Ile Val
            3875                3880                3885
Asp Gly Lys Leu Trp Phe Gln Leu Asp Cys Gly Ser Gly Pro Gly Ile
            3890                3895                3900
Leu Gly Ile Ser Gly Arg Ala Val Asn Asp Gly Ser Trp His Ser Val
3905                3910                3915                3920
Phe Leu Glu Leu Asn Arg Asn Phe Thr Ser Leu Ser Leu Asp Asp Ser
            3925                3930                3935
Tyr Val Glu Arg Arg Arg Ala Pro Leu Tyr Phe Gln Thr Leu Ser Thr
            3940                3945                3950
Glu Ser Ser Ile Tyr Phe Gly Ala Leu Val Gln Ala Asp Asn Ile Arg
            3955                3960                3965
Ser Leu Thr Asp Thr Arg Val Thr Gln Val Leu Ser Gly Phe Gln Gly
            3970                3975                3980
Cys Leu Asp Ser Val Ile Leu Asn Asn Asn Glu Leu Pro Leu Gln Asn
3985                3990                3995                4000
Lys Arg Ser Ser Phe Ala Glu Val Val Gly Leu Thr Glu Leu Lys Leu
            4005                4010                4015
Gly Cys Val Leu Tyr Pro Asp Ala Cys Lys Arg Ser Pro Cys Gln His
            4020                4025                4030
Gly Gly Ser Cys Thr Gly Leu Pro Ser Gly Gly Tyr Gln Cys Thr Cys
            4035                4040                4045
Leu Ser Gln Phe Thr Gly Arg Asn Cys Glu Ser Glu Ile Thr Ala Cys
            4050                4055                4060
Phe Pro Asn Pro Cys Arg Asn Gly Gly Ser Cys Asp Pro Ile Gly Asn
4065                4070                4075                4080
Thr Phe Ile Cys Asn Cys Lys Ala Gly Leu Thr Gly Val Thr Cys Glu
            4085                4090                4095
Glu Asp Ile Asn Glu Cys Glu Arg Glu Cys Glu Asn Gly Gly Ser
            4100                4105                4110
Cys Val Asn Val Phe Gly Ser Phe Leu Cys Asn Cys Thr Pro Gly Tyr
            4115                4120                4125
Val Gly Gln Tyr Cys Gly Leu Arg Pro Val Val Pro Asn Ile Gln
            4130                4135                4140
Ala Gly His Ser Tyr Val Gly Lys Glu Glu Leu Ile Gly Ile Ala Val
4145                4150                4155                4160
Val Leu Phe Val Ile Phe Ile Leu Val Val Leu Phe Ile Val Phe Arg
            4165                4170                4175
Lys Lys Val Phe Arg Lys Asn Tyr Ser Arg Asn Asn Ile Thr Leu Val
            4180                4185                4190
```

```
Gln Asp Pro Ala Thr Ala Ala Leu Leu Asn Lys Ser Asn Gly Ile Pro
        4195                4200                4205

Phe Arg Asn Leu Arg Gly Ser Gly Asp Gly Arg Asn Val Tyr Gln Glu
    4210                4215                4220

Val Gly Pro Pro Gln Val Pro Val Arg Pro Met Ala Tyr Thr Pro Cys
4225                4230                4235                4240

Phe Gln Ser Asp Ser Arg Ser Asn Leu Asp Lys Ile Val Asp Gly Leu
            4245                4250                4255

Gly Gly Glu His Gln Glu Met Thr Thr Phe His Pro Glu Ser Pro Arg
            4260                4265                4270

Ile Leu Thr Ala Arg Arg Gly Val Val Val Cys Ser Val Ala Pro Asn
        4275                4280                4285

Leu Pro Ala Val Ser Pro Cys Arg Ser Asp Cys Asp Ser Ile Arg Lys
    4290                4295                4300

Asn Gly Trp Asp Ala Gly Thr Glu Asn Lys Gly Val Asp Asp Pro Gly
4305                4310                4315                4320

Glu Val Thr Cys Phe Ala Gly Ser Asn Lys Gly Ser Asn Ser Glu Val
            4325                4330                4335

Gln Ser Leu Ser Ser Phe Gln Ser Asp Ser Gly Asp Asp Asn Ala Ser
            4340                4345                4350

Ile Val Thr Val Ile Gln Leu Val Asn Asn Val Val Asp Thr Ile Glu
        4355                4360                4365

Asn Glu Val Ser Val Met Asp Gln Gly Gln Asn Tyr Asn Arg Ala Tyr
    4370                4375                4380

His Trp Asp Thr Ser Asp Trp Met Pro Gly Ala Arg Leu Ser Asp Ile
4385                4390                4395                4400

Glu Glu Val Pro Asn Tyr Glu Asn Gln Asp Gly Gly Ser Ala His Gln
            4405                4410                4415

Gly Ser Thr Arg Glu Leu Glu Ser Asp Tyr Tyr Leu Gly Gly Tyr Asp
            4420                4425                4430

Ile Asp Ser Glu Tyr Pro Pro His Glu Glu Glu Phe Leu Ser Gln
        4435                4440                4445

Asp Gln Leu Pro Pro Leu Pro Glu Asp Phe Pro Asp Gln Tyr Glu
    4450                4455                4460

Ala Leu Pro Pro Ser Gln Pro Val Ser Leu Ala Ser Thr Leu Ser Pro
4465                4470                4475                4480

Asp Cys Arg Arg Arg Pro Gln Phe His Pro Ser Gln Tyr Leu Pro Pro
            4485                4490                4495

His Pro Phe Pro Asn Glu Thr Asp Leu Val Gly Pro Pro Ala Ser Cys
            4500                4505                4510

Glu Phe Ser Thr Phe Ala Val Ser Met Asn Gln Gly Thr Glu Pro Thr
            4515                4520                4525

Gly Pro Ala Asp Ser Val Ser Leu Ser Leu His Asn Ser Arg Gly Thr
            4530                4535                4540

Ser Ser Ser Asp Val Ser Ala Asn Cys Gly Phe Asp Asp Ser Glu Val
4545                4550                4555                4560

Ala Met Ser Asp Tyr Glu Ser Val Gly Glu Leu Ser Leu Ala Ser Leu
            4565                4570                4575

His Ile Pro Phe Val Glu Thr Gln His Gln Thr Gln Val
            4580                4585

<210> SEQ ID NO 3
<211> LENGTH: 11559
```

<212> TYPE: DNA
<213> ORGANISM: homo sapiens

<400> SEQUENCE: 3

| | | | | | |
|---|---|---|---|---|---|
| atggatataa | ttatgggaca | ctgtgtgggc | acacggcctc | ctgcttgttg | cctcatcctc | 60 |
| ctgcttttca | agcttttggc | cactgtctcc | caggggctgc | cagggactgg | acccctgggc | 120 |
| ttccacttca | cacattccat | ttataatgct | accgtgtatg | agaactcagc | agcaaggacc | 180 |
| tacgtcaaca | gccagagtag | aatgggcatc | accttaatag | atctatcctg | ggatatcaaa | 240 |
| tacagaatag | tgtccggaga | cgaggaaggc | tttttcaaag | cagaggaagt | catcattgca | 300 |
| gatttctgtt | ttctcagaat | aagaactaaa | ggtggcaatt | ctgccatatt | aaatagggaa | 360 |
| atccaggata | attatttatt | gatagtaaaa | ggttctgtca | gaggagagga | tttggaagca | 420 |
| tggaccaaag | tgaatataca | ggttttagat | atgaatgatc | tgagaccttt | gttttcaccc | 480 |
| acaacatact | ctgttaccat | agcagaaagc | acacctctaa | ggactagtgt | tgcccaggtg | 540 |
| actgcaacag | acgcagatat | tggttccaat | ggagaattct | actactactt | taaaaataaa | 600 |
| gttgatctct | tttcagttca | ccccacgagt | ggtgtcatct | ccttaagtgg | tcgattaaat | 660 |
| tatgatgaaa | agaataggta | tgatctggaa | attttggctg | tggaccgggg | aatgaaactg | 720 |
| tatgggaaca | atggagtgag | cagtactgca | aagctttatg | ttcacattga | gcgcataaat | 780 |
| gaacatgccc | caacaatcca | tgtagtcact | catgttcctt | tctcgttgga | aaaagagcca | 840 |
| acatatgcag | tggtgacagt | tgatgactta | gatgatggag | cgaatggaga | gatcgaatct | 900 |
| gtttccattg | tggctgggga | tcctttagat | cagttcttcc | tggctaagga | aggaaagtgg | 960 |
| ttgaatgagt | acaagattaa | ggagaggaag | cagattgact | gggagagctt | tccctatggc | 1020 |
| tacaatctca | ctcttcaagc | aaaagacaag | ggatctcctc | aaaaatgttc | agcattaaag | 1080 |
| gcagtctaca | ttggcaaccc | cacaagagac | actgtcccca | ttagatttga | aaaagaagtg | 1140 |
| tacgatgtga | gcataagtga | attttcccct | cctggtgtcg | tggttgctat | agtaaaatta | 1200 |
| agtcctgaac | cgatagatgt | ggaatacaaa | ttatctcctg | gtgaggatgc | agtgtacttt | 1260 |
| aaaattaatc | ctcggtcggg | tctgattgtt | acagcacggc | cactgaatac | tgttaagaag | 1320 |
| gaggtttata | aactggaggt | gacaaacaag | gaaggagatt | taaaagcaca | ggtcaccatc | 1380 |
| agcatagaag | atgcaaatga | ccacacccca | gaatttcagc | aaccactgta | tgatgcttat | 1440 |
| gtgaatgaaa | gtgtcccagt | gggaaccagc | gttctaacag | tttcagcttc | tgataaggat | 1500 |
| aaaggagaaa | atgggtacat | cacctatagt | atcgctagcc | tgaatttgtt | accatttgtc | 1560 |
| attaatcagt | ttacaggtgt | tattagcaca | actgaagaac | tggattttga | atcctcccca | 1620 |
| gaaatttaca | gattcattgt | tagagcctct | gactggggtt | caccataccg | ccatgaaagt | 1680 |
| gaggtcaatg | tgactattcg | aataggaaat | gtcaacgaca | acagccctct | ctttgaaaaa | 1740 |
| gtggcttgcc | agggagttat | ttcatatgac | tttccagttg | gtgtcacat | cacagcagtc | 1800 |
| tcagcgatcg | atatcgatga | acttgaactt | gtaaagtaca | aaatcatttc | tggaaatgaa | 1860 |
| cttggcttct | tttatttaaa | cccagattct | ggtgttttac | agcttaaaaa | atcactgaca | 1920 |
| aattctggca | ttaaaaatgg | caattttgcc | ctcagaatta | cagcaactga | tggagagaat | 1980 |
| cttgcagacc | ccatgtctat | taacatttca | gtcctacatg | gaaagtgtc | ttcaaagagc | 2040 |
| ttcagttgca | gagaaactcg | tgtggctcaa | aagctggcag | agaaactact | cattaaggca | 2100 |
| aaagcaaatg | ggaaactgaa | tctggaagat | ggatttcttg | acttttattc | aattaataga | 2160 |
| cagggaccat | attttgacaa | gtcttttcct | tctgatgtgg | ctgtaaagga | ggatctgcca | 2220 |

-continued

```
gttggtgcta acattctgaa gattaaagcc tatgatgccg actctggctt caatggaaaa       2280
gtgctatttta caatatcaga tggaaatacg gatagttgct ttaatattga tatggagact     2340
gggcagctta aagtccttat gcccatggat cgagaacaca cagacctcta tctccttaat     2400
atcaccatct atgacttagg taatccacag aaatcgtcat ggagactgct gaccatcaat      2460
gtggaggatg ctaatgacaa tagcccagtt tttattcaag acagttactc agttaacatt     2520
cttgaaagtt caggcattgg tactgaaatc attcaagtgg aagccagaga caaagactta     2580
ggttctaatg gtgaagtgac ttactcagtc ttgacagata cacagcagtt tgccatcaat     2640
agctcaactg gaatcgttta tgtagccgac cagttggacc gggaatccaa agccaattat     2700
tctttgaaaa tagaagccag ggacaaggca gagagtggtc agcagctgtt ttcagttgtc      2760
actcttaaag tttttttaga tgatgtcaat gactgctccc cagctttcat tcccagtagc    2820
tatagtgtga aggttcttga agatctccct gttggcactg tcattgcttg gcttgagacc   2880
catgatccag atcttggact gggggtcaa gtgcgctatt ctttggtcaa tgactataat     2940
gggagatttg aaatagataa agcaagtggt gccatccgct tgagcaaaga gcttgattat    3000
gagaaacagc agttctataa ccttactgtg cgggccaaag acaaagggcg gcctgtctct    3060
ctgtcatctg tttcctttgt tgaggtggaa gtggtggatg tcaatgaaaa cctccacact    3120
ccctatttcc cagactttgc tgttgttgga tctgtaaagg aaaactcacg cattggaaca    3180
agcgtgctgc aggtgactgc tcgagatgaa gactccggaa gggatggaga gatccagtac    3240
tccatcaggg atggcagtgg tcttggaagg ttcagtatag cgacgagag tggggtcatc     3300
actgccgcag acattcttga tcgggagaca atggggtcat actggctaac agtgtatgcc    3360
acagacaggg gcgttgttcc actctactcc accattgagg tctacattga agttgaagat    3420
gtgaatgaca atgccccgct gacctcagaa cctatatatt atcctgttgt catggaaaac    3480
tctccaaagg acgtatctgt cattcagatc caggctgaag atcctgactc cagttccaat    3540
gaaaaactga catacaggat tacaagtgga atcctcaga atttttttgc catcaatatc     3600
aaaacaggtc tgattacaac aacttcaagg aaattggatc gagaacagca ggcagaacat    3660
tttctggagg tgactgtgac agatggtggt ccctctccaa aacagtcaac catttgggtg    3720
gtggttcagg ttctagatga aaatgacaac aagcccagt tcccagagaa ggtctaccag     3780
atcaagctgc cagaacgtga ccgaaagaag agaggagaac cgatttacag ggcttttgca    3840
tttgatagag atgagggccc caacgcagaa atctcctaca gtattgtgga tgggaatgat    3900
gacggaaagt tctttattga ccctaaaact gggatggttt cttctagaaa gcagtttaca    3960
gcaggcagtt atgacatcct aacgataaag gcagtggaca atgggcgccc acagaaatcc    4020
tccacggccc gcctccacat tgaatggatt aagaaaccac cccttcacc tataccattg    4080
accttcgatg agccgtttta taacttcaca gtcatggaaa gtgatagagt gactgaaatt    4140
gtaggggtgg tgtctgtgca gccagctaac acccctctgt ggtttgacat agttggggggg   4200
aattttgaca gcgcttttga tgcagagaag ggtgttggga caattgtcat cgcaaaacct    4260
ttggatgcag agcagaggtc catctataat atgagtgtgg aagtcaccga tgggacaaat    4320
gttgctgtta ctcaggtatt tatcaaagtg ctggataata atgataatgg cccagaattc    4380
tctcagccga attacgatgt gacaatttcc gaggatgtgc ttccgacac ggagatcctg     4440
cagattgaag ccacagatag agatgagaag cacaagctga gctacactgt tcatagcagc   4500
atcgactcca tcagcatgag aaaattccgg attgaccccta gcactggcgt gctctatact    4560
gccgagaggc tggaccatga ggcccaggac aagcacattc tcaacataat ggtcagagat    4620
```

-continued

```
caggagtttc cttatcgaag aaacttggcc cgagtcattg tgaatgtgga ggatgctaat    4680
gatcacagtc cttattttac caacccactg tatgaagcgt ctgtgtttga atctgctgct    4740
ctgggatcag ctgttctgca agtgacggct ctggacaaag acaaggaga aaatgcagaa    4800 ctcatatata ccatagaagc agggaacact gggaacatgt ttaagatcga accggtccta    4860
ggcatcatca ccatttgcaa agaaccagac atgacgacga tgggtcagtt tgtcctatcc    4920
atcaaagtca cagatcaggg atccccgcca atgtctgcta ctgcaattgt gcgcatttcc    4980
gtcaccatgt ctgacaattc tcaccccaag ttcattcaca aagactacca agcagaagta    5040
aatgaaaatg ttgacattgg aacatcagtc attctaatct ctgccatcag tcaatctacc    5100
ctcatttatg aagtcaaaga tggagacatt aatgggatct ttaccataaa tccatattct    5160
ggagtcatca ccactcagaa ggccctggat tatgagcgca catcctctta tcaactcatc    5220
attcaggcca ccaatatggc aggaatggct tccaatgcta cagtcaatat tcagattgtt    5280
gatgaaaatg ataatgcccc agttttttctc tttttctcaat actcaggcag cctaagtgag    5340
gctgccccaa ttaatagcat tgtcaggagc ttggataaca gcccactggt gattcgagcc    5400
acagatgctg acagcaaccg gaatgctctg cttgtgtatc agattgtgga gtcaacagca    5460
aaaaagtttt tcacggtgga ctccagtaca ggtgcaatca gaacaattgc caacctggac    5520
catgaaacca ttgcccattt ccattttcat gtgcatgtga gagacagtgg tagcccccaa    5580
ctgactgcag agagtcccgt tgaagtcaac attgaggtga cagatgtgaa tgataaccca    5640
cctgttttta ctcaggctgt gtttgagact atcttacttc tacctaccta tgttggagtg    5700
gaggttctga agttagtgc cacagatcct gactctgagg tacccccctga actgacatac    5760 agcctaatgg aaggcagttt ggatcatttt ttaattgact caaacagtgg agtacttacc    5820
ataaaaaaca acaacctctc caaggatcac tacatgctga tagttaaggt gtctgatgga    5880
aagttctaca gtacctccat ggtcaccatc atggttaaag aagccatgga cagcggcctc    5940
cactttacac aaagcttcta ttccacctca atctcagaga acaacactaa cataaccaaa    6000
gttgctattg tcaatgcagt tggaaatcgc cttaatgagc ccttaaaata cagcatctta    6060
aacccaggaa ataagttcaa gataaaatct acctcagggg tcattcagac gactggagtc    6120
ccctttgacc gtgaagaaca agagttatat gagctggtgg tagaagccag ccgtgagctg    6180
gaccatctgc gtgtggccag agtggtggtc agggttaaca ttgaagacat aaatgacaat    6240
tctccagtct ttgtgggcct cccatactat gctgctgttc aagtggatgc ggaacccggg    6300
actctgattt atcaggtgac agccattgac aaagataaag gtccaaatgg agaagtgacc    6360
tatgtcctgc aggatgacta tggccacttt gaaattaacc ctaattcagg gaatgttatt    6420
ttaaaggaag cattcaactc tgacttgtcc aacattgagt atggagtcac catcctagcc    6480
aaggatggcg gaaaaccttc tttgtctaca tctgtggagc ttcccatcac tattgtcaac    6540
aaagcaatgc ctgtgtttga taagcccttt tatacagcat ctgtcaatga agacatcaga    6600
atgaacacac ccatcctaag catcaatgcc accagtccag aaggccaagg catcatatat    6660
atcattatcg atgggaccc ttttaaacag tttaacattg actttgacac tggggtcctg    6720
aaagttgtta gccctttgga ttatgaagtt acatctgctt acaagctgac aataagagcc    6780
agcgacgccc ttactggtgc tagggctgaa gtcactgttg acttgctagt taatgatgta    6840
aatgacaacc cccctatttt cgatcagcct acatacaata caacactatc agaagcatct    6900
cttattggga cacctgtttt acaagttgtc tctattgatg cagactcaga aaacaataaa    6960
```

```
atggtacatt atcagattgt ccaggatacc tacaatagca cagattatttt tcacatagat      7020 agctcaagtg gcttaatcct gacagcacga atgctggacc atgagttagt acaacactgc      7080
actttgaaag tcagatcaat agatagtggc ttcccatcac tgagcagtga ggttctcgtt      7140
catatctaca tctctgatgt aaatgacaac cctccagttt ttaatcagct catttatgag      7200
tcatatgtga gtgaattagc cccccggggc cattttgtaa cctgtgtaca agcctctgat      7260
gcagacagct ctgattttga ccggttggaa tatagcattt tatctgggaa tgaccggacg      7320
agctttctga tggacagcaa gagtggagtt atcacattgt ccaaccatcg gaagcagcgg      7380
atggagcctc tgtacagtct caatgtgtct gtctctgatg ggttgttcac cagcactgca      7440
caggtgcata ttagggtact tggggctaac ttgtacagcc ctgccttttc acaaagcaca      7500
tacgtagctg aggtgagaga gaacgtggct gcaggaacaa aggtaattca tgttcgagcc      7560
acagatggtg atccagggac ttatgggcag atcagctatg ccatcatcaa tgactttgcc      7620
aaggatcgat tcctcataga cagcaatggg caggtcatca ccacagaaag gctagaccgg      7680
gaaaaccctc tagaagggga tgttagtatt tttgtgaggg cccttgatgg tggagggaga      7740
acaactttct gcactgtgag agtgattgtt gtggatgaaa atgacaatgc tccccagttc      7800
atgacagtgg aatatagagc cagtgtcagg gcagatgttg aaggggcca cttggtcact      7860 caagttcaag ccatagatcc cgatgatgga gcaaattcaa ggattactta ttccctctat      7920
agcgaggcct ctgtttcagt ggccgacctc ctggaaatcg atcctgacaa tggctggatg      7980
gtcacaaagg gtaattttaa ccagctgaaa aatacagtgc tttcgttctt tgtcaaagca      8040
gtagatgggg gcatcccagt aaagcactcc ctcattcctg tctatatcca cgtcttgccc      8100
cctgaaacgt tcttgccatc attcacccag tctcagtatt cctttaccat tgcagaagat      8160
acagccattg ggagtacagt ggacaccctg aggattttgc ccagtcagaa tgtctggttc      8220
agcacagtta atgggaacg gccagaaaat aacaaagggg gcgtattcgt catagaacag      8280
gaaacaggca ctattaagct tgacaaacgc cttgaccgtg aaaccagccc agctttccac      8340
tttaaagtag cagccactat accccctggac aaagtagaca ttgtgtttac tgtggatgta      8400
gatatcaagg tattggattt gaatgacaac aagccagtct ttgaaacttc aagctatgac      8460
accattataa tggaagggat gcctgttggc accaaactca cacaagtgag agctattgat      8520
atggactggg gagccaatgg acaagtcact tactccctcc actcggattc ccagcccgaa      8580
aaggtaatgg aagcattcaa tattgacagc aacacgggct ggatcagtac cttgaaggac      8640
ctagatcacg agacagaccc cacattcacc ttctctgtgg tggcctctga ccttggagag      8700
gcattctctc tttcctccac ggccttggtc tctgtcagag tgacagatat aaatgacaat      8760
gcaccagtct tcgcgcagga agtgtaccga gggaatgtga aggagagcga cccaccgggc      8820
gaggtggtag ccgtcctcag cacctgggac agagacacat ccgacgttaa tcgccaagtg      8880
agctaccata ttacaggagg aaaccctcga ggaaggtttg ctctgggcct ggtgcaaagt      8940
gagtggaagg tctatgtgaa gaggcctcta gacagagaag aacaggacat ttactttctc      9000
aatatcactg ccactgatgg gcttttgtc acacaggcca tggtggaagt gagcgtcagt      9060
gatgtgaatg acaatagccc agtgtgtgat caggttgcat atacagcatt acttcctgaa      9120
gacattccat caaataaaat catcctgaaa gtcagtgcaa aggatgctga tattggatcc      9180
aatggatata tacgatactc actctatgga tctggaaaca gtgaattttt tctagatcca      9240
gaaagtggcg agtaaaaaac cttggctctg ttggaccggg agaggatccc cgtgtacagc      9300
ctgatggcca aggccactga cggggtggc aggttctgcc agtccaacat ccacctaatc      9360
```

-continued

```
ctggaggatg tgaatgataa ccccctgtg ttttcttctg accactacaa cacctgtgtc    9420
tatgagaaca cagccaccaa ggctctgttg accagagttc aagccgtgga ccccgacatt    9480
ggcatcaata ggaaggtcgt gtactccctg cagactcag ctggtggggt cttctccatt     9540
gacagctcat ctggcatcat catcctggag cagccactgg accgtgagca gcagtcttcg    9600
tacaacatca gcgtgcgggc cactgaccag agtcctggac agtccctgtc ctctctcact    9660
actgtcacca tcaccgttct ggacattaat gacaacccc ctgtgtttga gaggagggac     9720
tacctggtga cggtgcctga ggacacctcc cctggcaccc aagtccttgc tgttttgcc    9780
accagcaaag atattggcac aaatgctgag atcacttatc tcatccggtc tgggaacgaa    9840
caagggaaat ttaagatcaa ccccaagaca ggggtatt ctgtctctga agtcctggac      9900
tatgaattat gcaaaaggtt ttacctggta gtggaagcca agatggggg caccccagct     9960
ctcagcgctg tggccactgt caacatcaac ctcacagatg ttaatgacaa ccctcccaag    10020
ttcagccaag acgtctacag tgcggttatc agtgaagacg ccttggtggg agactctgtc    10080
attttgctaa tagcagaaga tgtagacagc cagcccaacg gacagattca tttttccatt    10140
gtgaatggag atcgggacaa tgaatttact gtagatcctg tcttgggact tgtgaaagtt    10200
aagaagaaat tggaccggga acgggtgtct ggatactctc tgcttgtcca ggccgtagac    10260
agtggcattc ctgcaatgtc atcaactgca actgtcaaca ttgatatttc tgatgtgaat    10320
gacaacagcc cggtgtttac acctgccaac tatactgctg tgattcagga aaataagcca    10380
gtgggcacca gcatcttgca gctggtggtg acagacagag actcctttca caatgggcct    10440
cccttttcat tctctatttt gtcgggaaat gaagaggagg agtttgtgtt ggaccctcat    10500
gggatcttgc ggtcggctgt ggtcttccag cacacagagt ctctggaata cgtgttgtgt    10560
gtccaggcaa aggattcagg caaaccccag caagtttctc acacttacat ccgcgtgcga    10620
gtcattgagg aaagcaccca caagcccaca gccattcccc tggaaatttt cattgtcacc    10680
atggaggatg actttcctgg tgggtcatt gggaagattc atgccacaga tcaagacatg    10740
tatgatgtgc tcacatttgc cctgaaatcg gagcagaaaa gcttatttaa agtgaacagt    10800
cacgatggga aaatcatcgc cctgggaggc ctggacagcg gcaagtatgt cctgaatgtg    10860
tctgtgagtg atggtcgctt ccaggtaccc attgatgtgg tcgtgcatgt ggagcagttg    10920
gtgcatgaga tgctgcagaa cactgtcacc atccgctttg aaaatgtgtc ccctgaggac    10980
ttcgtggggc tgcacatgca tgggttccgg cgcacccctg gaatgcagt cctcacccag    11040
aagcaggaca gcctgcgcat catcagcatc cagcccgtgg caggcaccaa ccaactggac    11100
atgctgtttg cggtggagat gcacagcagc gagttctaca gccagccta cctgatccag    11160
aagctgtcca tgctagaag acacctggag aatatcatgc gcatctcagc catcttggag    11220
aagaactgct cagggctgga ctgtcaggaa cagcattgtg agcaaggctt gtcactcgat    11280
tcccacgcgc tcatgaccta cagcacggct cgcatcagct ttgtgtgtcc gcgtttctac    11340
aggaacgtgc gttgcacctg caatggagga ctgtgtccgg ggtccaacga tccttgtgtg    11400
gagaagccgt gtccagggga catgcagtgt gtcggttatg aagccagcag agaccgttc     11460
ctctgccagt gtccaccagg gaagctcgga gagtgctcag gcacacttc tctcagctt      11520
gctggaaaca gttacatcaa atatcggctt tctgaatag                           11559
```

<210> SEQ ID NO 4
<211> LENGTH: 3852
<212> TYPE: PRT

-continued

<213> ORGANISM: homo sapiens

<400> SEQUENCE: 4

Met Asp Ile Ile Met Gly His Cys Val Gly Thr Arg Pro Pro Ala Cys
1               5                   10                  15

Cys Leu Ile Leu Leu Phe Lys Leu Leu Ala Thr Val Ser Gln Gly
            20                  25                  30

Leu Pro Gly Thr Gly Pro Leu Gly Phe His Phe Thr His Ser Ile Tyr
            35                  40                  45

Asn Ala Thr Val Tyr Glu Asn Ser Ala Ala Arg Thr Tyr Val Asn Ser
    50                  55                  60

Gln Ser Arg Met Gly Ile Thr Leu Ile Asp Leu Ser Trp Asp Ile Lys
65                  70                  75                  80

Tyr Arg Ile Val Ser Gly Asp Glu Glu Gly Phe Phe Lys Ala Glu Glu
                85                  90                  95

Val Ile Ile Ala Asp Phe Cys Phe Leu Arg Ile Arg Thr Lys Gly Gly
            100                 105                 110

Asn Ser Ala Ile Leu Asn Arg Glu Ile Gln Asp Asn Tyr Leu Leu Ile
        115                 120                 125

Val Lys Gly Ser Val Arg Gly Glu Asp Leu Glu Ala Trp Thr Lys Val
    130                 135                 140

Asn Ile Gln Val Leu Asp Met Asn Asp Leu Arg Pro Leu Phe Ser Pro
145                 150                 155                 160

Thr Thr Tyr Ser Val Thr Ile Ala Glu Ser Thr Pro Leu Arg Thr Ser
                165                 170                 175

Val Ala Gln Val Thr Ala Thr Asp Ala Asp Ile Gly Ser Asn Gly Glu
            180                 185                 190

Phe Tyr Tyr Tyr Phe Lys Asn Lys Val Asp Leu Phe Ser Val His Pro
        195                 200                 205

Thr Ser Gly Val Ile Ser Leu Ser Gly Arg Leu Asn Tyr Asp Glu Lys
    210                 215                 220

Asn Arg Tyr Asp Leu Glu Ile Leu Ala Val Asp Arg Gly Met Lys Leu
225                 230                 235                 240

Tyr Gly Asn Asn Gly Val Ser Ser Thr Ala Lys Leu Tyr Val His Ile
                245                 250                 255

Glu Arg Ile Asn Glu His Ala Pro Thr Ile His Val Val Thr His Val
            260                 265                 270

Pro Phe Ser Leu Glu Lys Glu Pro Thr Tyr Ala Val Val Thr Val Asp
        275                 280                 285

Asp Leu Asp Asp Gly Ala Asn Gly Glu Ile Glu Ser Val Ser Ile Val
    290                 295                 300

Ala Gly Asp Pro Leu Asp Gln Phe Phe Leu Ala Lys Glu Gly Lys Trp
305                 310                 315                 320

Leu Asn Glu Tyr Lys Ile Lys Glu Arg Lys Gln Ile Asp Trp Glu Ser
                325                 330                 335

Phe Pro Tyr Gly Tyr Asn Leu Thr Leu Gln Ala Lys Asp Lys Gly Ser
            340                 345                 350

Pro Gln Lys Cys Ser Ala Leu Lys Ala Val Tyr Ile Gly Asn Pro Thr
        355                 360                 365

Arg Asp Thr Val Pro Ile Arg Phe Glu Lys Glu Val Tyr Asp Val Ser
    370                 375                 380

Ile Ser Glu Phe Ser Pro Pro Gly Val Val Ala Ile Val Lys Leu
385                 390                 395                 400

-continued

```
Ser Pro Glu Pro Ile Asp Val Glu Tyr Lys Leu Ser Pro Gly Glu Asp
            405                 410                 415

Ala Val Tyr Phe Lys Ile Asn Pro Arg Ser Gly Leu Ile Val Thr Ala
        420                 425                 430

Arg Pro Leu Asn Thr Val Lys Lys Glu Val Tyr Lys Leu Glu Val Thr
            435                 440                 445

Asn Lys Glu Gly Asp Leu Lys Ala Gln Val Thr Ile Ser Ile Glu Asp
450                 455                 460

Ala Asn Asp His Thr Pro Glu Phe Gln Gln Pro Leu Tyr Asp Ala Tyr
465                 470                 475                 480

Val Asn Glu Ser Val Pro Val Gly Thr Ser Val Leu Thr Val Ser Ala
                485                 490                 495

Ser Asp Lys Asp Lys Gly Glu Asn Gly Tyr Ile Thr Tyr Ser Ile Ala
            500                 505                 510

Ser Leu Asn Leu Leu Pro Phe Val Ile Asn Gln Phe Thr Gly Val Ile
        515                 520                 525

Ser Thr Thr Glu Glu Leu Asp Phe Glu Ser Ser Pro Glu Ile Tyr Arg
    530                 535                 540

Phe Ile Val Arg Ala Ser Asp Trp Gly Ser Pro Tyr Arg His Glu Ser
545                 550                 555                 560

Glu Val Asn Val Thr Ile Arg Ile Gly Asn Val Asn Asp Asn Ser Pro
                565                 570                 575

Leu Phe Glu Lys Val Ala Cys Gln Gly Val Ile Ser Tyr Asp Phe Pro
            580                 585                 590

Val Gly Gly His Ile Thr Ala Val Ser Ala Ile Asp Ile Asp Glu Leu
        595                 600                 605

Glu Leu Val Lys Tyr Lys Ile Ile Ser Gly Asn Glu Leu Gly Phe Phe
    610                 615                 620

Tyr Leu Asn Pro Asp Ser Gly Val Leu Gln Leu Lys Lys Ser Leu Thr
625                 630                 635                 640

Asn Ser Gly Ile Lys Asn Gly Asn Phe Ala Leu Arg Ile Thr Ala Thr
                645                 650                 655

Asp Gly Glu Asn Leu Ala Asp Pro Met Ser Ile Asn Ile Ser Val Leu
            660                 665                 670

His Gly Lys Val Ser Ser Lys Ser Phe Ser Cys Arg Glu Thr Arg Val
        675                 680                 685

Ala Gln Lys Leu Ala Glu Lys Leu Leu Ile Lys Ala Lys Ala Asn Gly
    690                 695                 700

Lys Leu Asn Leu Glu Asp Gly Phe Leu Asp Phe Tyr Ser Ile Asn Arg
705                 710                 715                 720

Gln Gly Pro Tyr Phe Asp Lys Ser Phe Pro Ser Asp Val Ala Val Lys
                725                 730                 735

Glu Asp Leu Pro Val Gly Ala Asn Ile Leu Ile Lys Ala Tyr Asp
            740                 745                 750

Ala Asp Ser Gly Phe Asn Gly Lys Val Leu Phe Thr Ile Ser Asp Gly
        755                 760                 765

Asn Thr Asp Ser Cys Phe Asn Ile Asp Met Glu Thr Gly Gln Leu Lys
    770                 775                 780

Val Leu Met Pro Met Asp Arg Glu His Thr Asp Leu Tyr Leu Leu Asn
785                 790                 795                 800

Ile Thr Ile Tyr Asp Leu Gly Asn Pro Gln Lys Ser Ser Trp Arg Leu
                805                 810                 815

Leu Thr Ile Asn Val Glu Asp Ala Asn Asp Asn Ser Pro Val Phe Ile
```

-continued

```
            820                 825                 830
Gln Asp Ser Tyr Ser Val Asn Ile Leu Glu Ser Ser Gly Ile Gly Thr
        835                 840                 845
Glu Ile Ile Gln Val Glu Ala Arg Asp Lys Asp Leu Gly Ser Asn Gly
850                 855                 860
Glu Val Thr Tyr Ser Val Leu Thr Asp Thr Gln Gln Phe Ala Ile Asn
865                 870                 875                 880
Ser Ser Thr Gly Ile Val Tyr Val Ala Asp Gln Leu Asp Arg Glu Ser
                885                 890                 895
Lys Ala Asn Tyr Ser Leu Lys Ile Glu Ala Arg Asp Lys Ala Glu Ser
            900                 905                 910
Gly Gln Gln Leu Phe Ser Val Val Thr Leu Lys Val Phe Leu Asp Asp
        915                 920                 925
Val Asn Asp Cys Ser Pro Ala Phe Ile Pro Ser Ser Tyr Ser Val Lys
930                 935                 940
Val Leu Glu Asp Leu Pro Val Gly Thr Val Ile Ala Trp Leu Glu Thr
945                 950                 955                 960
His Asp Pro Asp Leu Gly Leu Gly Gly Gln Val Arg Tyr Ser Leu Val
                965                 970                 975
Asn Asp Tyr Asn Gly Arg Phe Glu Ile Asp Lys Ala Ser Gly Ala Ile
            980                 985                 990
Arg Leu Ser Lys Glu Leu Asp Tyr Glu Lys Gln Gln Phe Tyr Asn Leu
        995                 1000                1005
Thr Val Arg Ala Lys Asp Lys Gly Arg Pro Val Ser Leu Ser Ser Val
        1010                1015                1020
Ser Phe Val Glu Val Glu Val Val Asp Val Asn Glu Asn Leu His Thr
1025                1030                1035                1040
Pro Tyr Phe Pro Asp Phe Ala Val Val Gly Ser Val Lys Glu Asn Ser
                1045                1050                1055
Arg Ile Gly Thr Ser Val Leu Gln Val Thr Ala Arg Asp Glu Asp Ser
            1060                1065                1070
Gly Arg Asp Gly Glu Ile Gln Tyr Ser Ile Arg Asp Gly Ser Gly Leu
        1075                1080                1085
Gly Arg Phe Ser Ile Asp Asp Glu Ser Gly Val Ile Thr Ala Ala Asp
        1090                1095                1100
Ile Leu Asp Arg Glu Thr Met Gly Ser Tyr Trp Leu Thr Val Tyr Ala
1105                1110                1115                1120
Thr Asp Arg Gly Val Val Pro Leu Tyr Ser Thr Ile Glu Val Tyr Ile
                1125                1130                1135
Glu Val Glu Asp Val Asn Asp Asn Ala Pro Leu Thr Ser Glu Pro Ile
            1140                1145                1150
Tyr Tyr Pro Val Val Met Glu Asn Ser Pro Lys Asp Val Ser Val Ile
        1155                1160                1165
Gln Ile Gln Ala Glu Asp Pro Asp Ser Ser Ser Asn Glu Lys Leu Thr
        1170                1175                1180
Tyr Arg Ile Thr Ser Gly Asn Pro Gln Asn Phe Phe Ala Ile Asn Ile
1185                1190                1195                1200
Lys Thr Gly Leu Ile Thr Thr Thr Ser Arg Lys Leu Asp Arg Glu Gln
                1205                1210                1215
Gln Ala Glu His Phe Leu Glu Val Thr Val Thr Asp Gly Gly Pro Ser
            1220                1225                1230
Pro Lys Gln Ser Thr Ile Trp Val Val Val Gln Val Leu Asp Glu Asn
        1235                1240                1245
```

-continued

```
Asp Asn Lys Pro Gln Phe Pro Glu Lys Val Tyr Gln Ile Lys Leu Pro
    1250                1255                1260
Glu Arg Asp Arg Lys Lys Arg Gly Glu Pro Ile Tyr Arg Ala Phe Ala
1265                1270                1275                1280
Phe Asp Arg Asp Glu Gly Pro Asn Ala Glu Ile Ser Tyr Ser Ile Val
                1285                1290                1295
Asp Gly Asn Asp Asp Gly Lys Phe Phe Ile Asp Pro Lys Thr Gly Met
            1300                1305                1310
Val Ser Ser Arg Lys Gln Phe Thr Ala Gly Ser Tyr Asp Ile Leu Thr
            1315                1320                1325
Ile Lys Ala Val Asp Asn Gly Arg Pro Gln Lys Ser Ser Thr Ala Arg
            1330                1335                1340
Leu His Ile Glu Trp Ile Lys Lys Pro Pro Ser Pro Ile Pro Leu
1345                1350                1355                1360
Thr Phe Asp Glu Pro Phe Tyr Asn Phe Thr Val Met Glu Ser Asp Arg
                1365                1370                1375
Val Thr Glu Ile Val Gly Val Val Ser Val Gln Pro Ala Asn Thr Pro
            1380                1385                1390
Leu Trp Phe Asp Ile Val Gly Gly Asn Phe Asp Ser Ala Phe Asp Ala
            1395                1400                1405
Glu Lys Gly Val Gly Thr Ile Val Ile Ala Lys Pro Leu Asp Ala Glu
            1410                1415                1420
Gln Arg Ser Ile Tyr Asn Met Ser Val Glu Val Thr Asp Gly Thr Asn
1425                1430                1435                1440
Val Ala Val Thr Gln Val Phe Ile Lys Val Leu Asp Asn Asn Asp Asn
                1445                1450                1455
Gly Pro Glu Phe Ser Gln Pro Asn Tyr Asp Val Thr Ile Ser Glu Asp
            1460                1465                1470
Val Leu Pro Asp Thr Glu Ile Leu Gln Ile Glu Ala Thr Asp Arg Asp
            1475                1480                1485
Glu Lys His Lys Leu Ser Tyr Thr Val His Ser Ser Ile Asp Ser Ile
            1490                1495                1500
Ser Met Arg Lys Phe Arg Ile Asp Pro Ser Thr Gly Val Leu Tyr Thr
1505                1510                1515                1520
Ala Glu Arg Leu Asp His Glu Ala Gln Asp Lys His Ile Leu Asn Ile
                1525                1530                1535
Met Val Arg Asp Gln Glu Phe Pro Tyr Arg Arg Asn Leu Ala Arg Val
            1540                1545                1550
Ile Val Asn Val Glu Asp Ala Asn Asp His Ser Pro Tyr Phe Thr Asn
            1555                1560                1565
Pro Leu Tyr Glu Ala Ser Val Phe Glu Ser Ala Ala Leu Gly Ser Ala
            1570                1575                1580
Val Leu Gln Val Thr Ala Leu Asp Lys Asp Lys Gly Glu Asn Ala Glu
1585                1590                1595                1600
Leu Ile Tyr Thr Ile Glu Ala Gly Asn Thr Gly Asn Met Phe Lys Ile
                1605                1610                1615
Glu Pro Val Leu Gly Ile Ile Thr Ile Cys Lys Glu Pro Asp Met Thr
            1620                1625                1630
Thr Met Gly Gln Phe Val Leu Ser Ile Lys Val Thr Asp Gln Gly Ser
            1635                1640                1645
Pro Pro Met Ser Ala Thr Ala Ile Val Arg Ile Ser Val Thr Met Ser
    1650                1655                1660
```

Asp Asn Ser His Pro Lys Phe Ile His Lys Asp Tyr Gln Ala Glu Val
1665                1670                1675                1680

Asn Glu Asn Val Asp Ile Gly Thr Ser Val Ile Leu Ile Ser Ala Ile
            1685                1690                1695

Ser Gln Ser Thr Leu Ile Tyr Glu Val Lys Asp Gly Asp Ile Asn Gly
            1700                1705                1710

Ile Phe Thr Ile Asn Pro Tyr Ser Gly Val Ile Thr Thr Gln Lys Ala
            1715                1720                1725

Leu Asp Tyr Glu Arg Thr Ser Ser Tyr Gln Leu Ile Ile Gln Ala Thr
            1730                1735                1740

Asn Met Ala Gly Met Ala Ser Asn Ala Thr Val Asn Ile Gln Ile Val
1745                1750                1755                1760

Asp Glu Asn Asp Asn Ala Pro Val Phe Leu Phe Ser Gln Tyr Ser Gly
            1765                1770                1775

Ser Leu Ser Glu Ala Ala Pro Ile Asn Ser Ile Val Arg Ser Leu Asp
            1780                1785                1790

Asn Ser Pro Leu Val Ile Arg Ala Thr Asp Ala Asp Ser Asn Arg Asn
            1795                1800                1805

Ala Leu Leu Val Tyr Gln Ile Val Glu Ser Thr Ala Lys Lys Phe Phe
            1810                1815                1820

Thr Val Asp Ser Ser Thr Gly Ala Ile Arg Thr Ile Ala Asn Leu Asp
1825                1830                1835                1840

His Glu Thr Ile Ala His Phe His Phe His Val His Val Arg Asp Ser
            1845                1850                1855

Gly Ser Pro Gln Leu Thr Ala Glu Ser Pro Val Glu Val Asn Ile Glu
            1860                1865                1870

Val Thr Asp Val Asn Asp Asn Pro Pro Val Phe Thr Gln Ala Val Phe
            1875                1880                1885

Glu Thr Ile Leu Leu Leu Pro Thr Tyr Val Gly Val Glu Val Leu Lys
            1890                1895                1900

Val Ser Ala Thr Asp Pro Asp Ser Glu Val Pro Pro Glu Leu Thr Tyr
1905                1910                1915                1920

Ser Leu Met Glu Gly Ser Leu Asp His Phe Leu Ile Asp Ser Asn Ser
            1925                1930                1935

Gly Val Leu Thr Ile Lys Asn Asn Asn Leu Ser Lys Asp His Tyr Met
            1940                1945                1950

Leu Ile Val Lys Val Ser Asp Gly Lys Phe Tyr Ser Thr Ser Met Val
            1955                1960                1965

Thr Ile Met Val Lys Glu Ala Met Asp Ser Gly Leu His Phe Thr Gln
1970                1975                1980

Ser Phe Tyr Ser Thr Ser Ile Ser Glu Asn Asn Thr Asn Ile Thr Lys
1985                1990                1995                2000

Val Ala Ile Val Asn Ala Val Gly Asn Arg Leu Asn Glu Pro Leu Lys
            2005                2010                2015

Tyr Ser Ile Leu Asn Pro Gly Asn Lys Phe Lys Ile Lys Ser Thr Ser
            2020                2025                2030

Gly Val Ile Gln Thr Thr Gly Val Pro Phe Asp Arg Glu Glu Gln Glu
            2035                2040                2045

Leu Tyr Glu Leu Val Val Glu Ala Ser Arg Glu Leu Asp His Leu Arg
            2050                2055                2060

Val Ala Arg Val Val Val Arg Val Asn Ile Glu Asp Ile Asn Asp Asn
2065                2070                2075                2080

Ser Pro Val Phe Val Gly Leu Pro Tyr Tyr Ala Ala Val Gln Val Asp

-continued

```
                2085                2090                2095
Ala Glu Pro Gly Thr Leu Ile Tyr Gln Val Thr Ala Ile Asp Lys Asp
            2100                2105                2110
Lys Gly Pro Asn Gly Glu Val Thr Tyr Val Leu Gln Asp Asp Tyr Gly
            2115                2120                2125
His Phe Glu Ile Asn Pro Asn Ser Gly Asn Val Ile Leu Lys Glu Ala
            2130                2135                2140
Phe Asn Ser Asp Leu Ser Asn Ile Glu Tyr Gly Val Thr Ile Leu Ala
2145                2150                2155                2160
Lys Asp Gly Gly Lys Pro Ser Leu Ser Thr Ser Val Glu Leu Pro Ile
            2165                2170                2175
Thr Ile Val Asn Lys Ala Met Pro Val Phe Asp Lys Pro Phe Tyr Thr
            2180                2185                2190
Ala Ser Val Asn Glu Asp Ile Arg Met Asn Thr Pro Ile Leu Ser Ile
            2195                2200                2205
Asn Ala Thr Ser Pro Glu Gly Gln Gly Ile Ile Tyr Ile Ile Ile Asp
            2210                2215                2220
Gly Asp Pro Phe Lys Gln Phe Asn Ile Asp Phe Asp Thr Gly Val Leu
2225                2230                2235                2240
Lys Val Val Ser Pro Leu Asp Tyr Glu Val Thr Ser Ala Tyr Lys Leu
            2245                2250                2255
Thr Ile Arg Ala Ser Asp Ala Leu Thr Gly Ala Arg Ala Glu Val Thr
            2260                2265                2270
Val Asp Leu Leu Val Asn Asp Val Asn Asp Asn Pro Pro Ile Phe Asp
            2275                2280                2285
Gln Pro Thr Tyr Asn Thr Thr Leu Ser Glu Ala Ser Leu Ile Gly Thr
            2290                2295                2300
Pro Val Leu Gln Val Val Ser Ile Asp Ala Asp Ser Glu Asn Asn Lys
2305                2310                2315                2320
Met Val His Tyr Gln Ile Val Gln Asp Thr Tyr Asn Ser Thr Asp Tyr
            2325                2330                2335
Phe His Ile Asp Ser Ser Ser Gly Leu Ile Leu Thr Ala Arg Met Leu
            2340                2345                2350
Asp His Glu Leu Val Gln His Cys Thr Leu Lys Val Arg Ser Ile Asp
            2355                2360                2365
Ser Gly Phe Pro Ser Leu Ser Ser Glu Val Leu Val His Ile Tyr Ile
            2370                2375                2380
Ser Asp Val Asn Asp Asn Pro Pro Val Phe Asn Gln Leu Ile Tyr Glu
2385                2390                2395                2400
Ser Tyr Val Ser Glu Leu Ala Pro Arg Gly His Phe Val Thr Cys Val
            2405                2410                2415
Gln Ala Ser Asp Ala Asp Ser Ser Asp Phe Ala Arg Leu Glu Tyr Ser
            2420                2425                2430
Ile Leu Ser Gly Asn Asp Arg Thr Ser Phe Leu Met Asp Ser Lys Ser
            2435                2440                2445
Gly Val Ile Thr Leu Ser Asn His Arg Lys Gln Arg Met Glu Pro Leu
            2450                2455                2460
Tyr Ser Leu Asn Val Ser Val Ser Asp Gly Leu Phe Thr Ser Thr Ala
2465                2470                2475                2480
Gln Val His Ile Arg Val Leu Gly Ala Asn Leu Tyr Ser Pro Ala Phe
            2485                2490                2495
Ser Gln Ser Thr Tyr Val Ala Glu Val Arg Glu Asn Val Ala Ala Gly
            2500                2505                2510
```

```
Thr Lys Val Ile His Val Arg Ala Thr Asp Gly Asp Pro Gly Thr Tyr
        2515                2520                2525
Gly Gln Ile Ser Tyr Ala Ile Ile Asn Asp Phe Ala Lys Asp Arg Phe
    2530                2535                2540
Leu Ile Asp Ser Asn Gly Gln Val Ile Thr Thr Glu Arg Leu Asp Arg
2545                2550                2555                2560
Glu Asn Pro Leu Glu Gly Asp Val Ser Ile Phe Val Arg Ala Leu Asp
                2565                2570                2575
Gly Gly Gly Arg Thr Thr Phe Cys Thr Val Arg Val Ile Val Val Asp
            2580                2585                2590
Glu Asn Asp Asn Ala Pro Gln Phe Met Thr Val Glu Tyr Arg Ala Ser
        2595                2600                2605
Val Arg Ala Asp Val Gly Arg Gly His Leu Val Thr Gln Val Gln Ala
    2610                2615                2620
Ile Asp Pro Asp Gly Ala Asn Ser Arg Ile Thr Tyr Ser Leu Tyr
2625                2630                2635                2640
Ser Glu Ala Ser Val Ser Val Ala Asp Leu Leu Glu Ile Asp Pro Asp
                2645                2650                2655
Asn Gly Trp Met Val Thr Lys Gly Asn Phe Asn Gln Leu Lys Asn Thr
            2660                2665                2670
Val Leu Ser Phe Phe Val Lys Ala Val Asp Gly Gly Ile Pro Val Lys
        2675                2680                2685
His Ser Leu Ile Pro Val Tyr Ile His Val Leu Pro Pro Glu Thr Phe
    2690                2695                2700
Leu Pro Ser Phe Thr Gln Ser Gln Tyr Ser Phe Thr Ile Ala Glu Asp
2705                2710                2715                2720
Thr Ala Ile Gly Ser Thr Val Asp Thr Leu Arg Ile Leu Pro Ser Gln
                2725                2730                2735
Asn Val Trp Phe Ser Thr Val Asn Gly Glu Arg Pro Glu Asn Asn Lys
            2740                2745                2750
Gly Gly Val Phe Val Ile Glu Gln Glu Thr Gly Thr Ile Lys Leu Asp
        2755                2760                2765
Lys Arg Leu Asp Arg Glu Thr Ser Pro Ala Phe His Phe Lys Val Ala
    2770                2775                2780
Ala Thr Ile Pro Leu Asp Lys Val Asp Ile Val Phe Thr Val Asp Val
2785                2790                2795                2800
Asp Ile Lys Val Leu Asp Leu Asn Asp Asn Lys Pro Val Phe Glu Thr
                2805                2810                2815
Ser Ser Tyr Asp Thr Ile Ile Met Glu Gly Met Pro Val Gly Thr Lys
            2820                2825                2830
Leu Thr Gln Val Arg Ala Ile Asp Met Asp Trp Gly Ala Asn Gly Gln
        2835                2840                2845
Val Thr Tyr Ser Leu His Ser Asp Ser Gln Pro Glu Lys Val Met Glu
    2850                2855                2860
Ala Phe Asn Ile Asp Ser Asn Thr Gly Trp Ile Ser Thr Leu Lys Asp
2865                2870                2875                2880
Leu Asp His Glu Thr Asp Pro Thr Phe Thr Phe Ser Val Val Ala Ser
                2885                2890                2895
Asp Leu Gly Glu Ala Phe Ser Leu Ser Ser Thr Ala Leu Val Ser Val
            2900                2905                2910
Arg Val Thr Asp Ile Asn Asp Asn Ala Pro Val Phe Ala Gln Glu Val
        2915                2920                2925
```

```
Tyr Arg Gly Asn Val Lys Glu Ser Asp Pro Gly Glu Val Val Ala
        2930                2935                2940

Val Leu Ser Thr Trp Asp Arg Asp Thr Ser Asp Val Asn Arg Gln Val
2945                2950                2955                2960

Ser Tyr His Ile Thr Gly Gly Asn Pro Arg Gly Arg Phe Ala Leu Gly
            2965                2970                2975

Leu Val Gln Ser Glu Trp Lys Val Tyr Val Lys Arg Pro Leu Asp Arg
            2980                2985                2990

Glu Glu Gln Asp Ile Tyr Phe Leu Asn Ile Thr Ala Thr Asp Gly Leu
            2995                3000                3005

Phe Val Thr Gln Ala Met Val Glu Val Ser Val Ser Asp Val Asn Asp
        3010                3015                3020

Asn Ser Pro Val Cys Asp Gln Val Ala Tyr Thr Ala Leu Leu Pro Glu
3025                3030                3035                3040

Asp Ile Pro Ser Asn Lys Ile Ile Leu Lys Val Ser Ala Lys Asp Ala
            3045                3050                3055

Asp Ile Gly Ser Asn Gly Tyr Ile Arg Tyr Ser Leu Tyr Gly Ser Gly
            3060                3065                3070

Asn Ser Glu Phe Phe Leu Asp Pro Glu Ser Gly Glu Leu Lys Thr Leu
            3075                3080                3085

Ala Leu Leu Asp Arg Glu Arg Ile Pro Val Tyr Ser Leu Met Ala Lys
        3090                3095                3100

Ala Thr Asp Gly Gly Gly Arg Phe Cys Gln Ser Asn Ile His Leu Ile
3105                3110                3115                3120

Leu Glu Asp Val Asn Asp Asn Pro Pro Val Phe Ser Ser Asp His Tyr
            3125                3130                3135

Asn Thr Cys Val Tyr Glu Asn Thr Ala Thr Lys Ala Leu Leu Thr Arg
            3140                3145                3150

Val Gln Ala Val Asp Pro Asp Ile Gly Ile Asn Arg Lys Val Val Tyr
            3155                3160                3165

Ser Leu Ala Asp Ser Ala Gly Gly Val Phe Ser Ile Asp Ser Ser Ser
        3170                3175                3180

Gly Ile Ile Ile Leu Glu Gln Pro Leu Asp Arg Glu Gln Gln Ser Ser
3185                3190                3195                3200

Tyr Asn Ile Ser Val Arg Ala Thr Asp Gln Ser Pro Gly Gln Ser Leu
            3205                3210                3215

Ser Ser Leu Thr Thr Val Thr Ile Thr Val Leu Asp Ile Asn Asp Asn
            3220                3225                3230

Pro Pro Val Phe Glu Arg Arg Asp Tyr Leu Val Thr Val Pro Glu Asp
            3235                3240                3245

Thr Ser Pro Gly Thr Gln Val Leu Ala Val Phe Ala Thr Ser Lys Asp
            3250                3255                3260

Ile Gly Thr Asn Ala Glu Ile Thr Tyr Leu Ile Arg Ser Gly Asn Glu
3265                3270                3275                3280

Gln Gly Lys Phe Lys Ile Asn Pro Lys Thr Gly Gly Ile Ser Val Ser
            3285                3290                3295

Glu Val Leu Asp Tyr Glu Leu Cys Lys Arg Phe Tyr Leu Val Val Glu
            3300                3305                3310

Ala Lys Asp Gly Gly Thr Pro Ala Leu Ser Ala Val Ala Thr Val Asn
            3315                3320                3325

Ile Asn Leu Thr Asp Val Asn Asp Asn Pro Pro Lys Phe Ser Gln Asp
            3330                3335                3340

Val Tyr Ser Ala Val Ile Ser Glu Asp Ala Leu Val Gly Asp Ser Val
```

-continued

```
          3345           3350           3355           3360
Ile Leu Leu Ile Ala Glu Asp Val Asp Ser Gln Pro Asn Gly Gln Ile
              3365           3370           3375
His Phe Ser Ile Val Asn Gly Asp Arg Asp Asn Glu Phe Thr Val Asp
              3380           3385           3390
Pro Val Leu Gly Leu Val Lys Val Lys Lys Leu Asp Arg Glu Arg
              3395           3400           3405
Val Ser Gly Tyr Ser Leu Leu Val Gln Ala Val Asp Ser Gly Ile Pro
              3410           3415           3420
Ala Met Ser Ser Thr Ala Thr Val Asn Ile Asp Ile Ser Asp Val Asn
  3425           3430           3435           3440
Asp Asn Ser Pro Val Phe Thr Pro Ala Asn Tyr Thr Ala Val Ile Gln
              3445           3450           3455
Glu Asn Lys Pro Val Gly Thr Ser Ile Leu Gln Leu Val Thr Asp
              3460           3465           3470
Arg Asp Ser Phe His Asn Gly Pro Pro Phe Ser Phe Ser Ile Leu Ser
              3475           3480           3485
Gly Asn Glu Glu Glu Phe Val Leu Asp Pro His Gly Ile Leu Arg
              3490           3495           3500
Ser Ala Val Val Phe Gln His Thr Glu Ser Leu Glu Tyr Val Leu Cys
  3505           3510           3515           3520
Val Gln Ala Lys Asp Ser Gly Lys Pro Gln Gln Val Ser His Thr Tyr
              3525           3530           3535
Ile Arg Val Arg Val Ile Glu Glu Ser Thr His Lys Pro Thr Ala Ile
              3540           3545           3550
Pro Leu Glu Ile Phe Ile Val Thr Met Glu Asp Asp Phe Pro Gly Gly
              3555           3560           3565
Val Ile Gly Lys Ile His Ala Thr Asp Gln Asp Met Tyr Asp Val Leu
  3570           3575           3580
Thr Phe Ala Leu Lys Ser Glu Gln Lys Ser Leu Phe Lys Val Asn Ser
  3585           3590           3595           3600
His Asp Gly Lys Ile Ile Ala Leu Gly Gly Leu Asp Ser Gly Lys Tyr
              3605           3610           3615
Val Leu Asn Val Ser Val Ser Asp Gly Arg Phe Gln Val Pro Ile Asp
              3620           3625           3630
Val Val His Val Glu Gln Leu Val His Glu Met Leu Gln Asn Thr
              3635           3640           3645
Val Thr Ile Arg Phe Glu Asn Val Ser Pro Glu Asp Phe Val Gly Leu
              3650           3655           3660
His Met His Gly Phe Arg Arg Thr Leu Arg Asn Ala Val Leu Thr Gln
  3665           3670           3675           3680
Lys Gln Asp Ser Leu Arg Ile Ile Ser Ile Gln Pro Val Ala Gly Thr
              3685           3690           3695
Asn Gln Leu Asp Met Leu Phe Ala Val Glu Met His Ser Ser Glu Phe
              3700           3705           3710
Tyr Lys Pro Ala Tyr Leu Ile Gln Lys Leu Ser Asn Ala Arg Arg His
              3715           3720           3725
Leu Glu Asn Ile Met Arg Ile Ser Ala Ile Leu Glu Lys Asn Cys Ser
              3730           3735           3740
Gly Leu Asp Cys Gln Glu Gln His Cys Glu Gln Gly Leu Ser Leu Asp
  3745           3750           3755           3760
Ser His Ala Leu Met Thr Tyr Ser Thr Ala Arg Ile Ser Phe Val Cys
              3765           3770           3775
```

```
Pro Arg Phe Tyr Arg Asn Val Arg Cys Thr Cys Asn Gly Gly Leu Cys
            3780                3785                3790
Pro Gly Ser Asn Asp Pro Cys Val Glu Lys Pro Cys Pro Gly Asp Met
        3795                3800                3805
Gln Cys Val Gly Tyr Glu Ala Ser Arg Arg Pro Phe Leu Cys Gln Cys
        3810                3815                3820
Pro Pro Gly Lys Leu Gly Glu Cys Ser Gly His Thr Ser Leu Ser Phe
3825                3830                3835                3840
Ala Gly Asn Ser Tyr Ile Lys Tyr Arg Leu Ser Glu
            3845                3850
```

<210> SEQ ID NO 5
<211> LENGTH: 13758
<212> TYPE: DNA
<213> ORGANISM: homo sapiens

<400> SEQUENCE: 5

```
atgggacact gtgtgggcac acggcctcct gcttgttgcc tcatcctcct gcttttcaag      60
cttttggcca ctgtctccca ggggctgcca gggactggac ccctgggctt ccacttcaca     120
cattccattt ataatgctac cgtgtatgag aactcagcag caaggaccta cgtcaacagc     180
cagagtagaa tgggcatcac cttaatagat ctatcctggg atatcaaata cagaatagtg     240
tccggagacg aggaaggctt tttcaaagca gaggaagtca tcattgcaga tttctgtttt     300
ctcagaataa gaactaaagg tggcaattct gccatattaa atagggaaat ccaggataat     360
tatttattga tagtaaaagg ttctgtcaga ggagaggatt tggaagcatg gaccaaagtg     420
aatatacagg ttttagatat gaatgatctg agacctttgt tttcacccac aacatactct     480
gttaccatag cagaaagcac acctctaagg actagtgttg cccaggtgac tgcaacagac     540
gcagatattg gttccaatgg agaattctac tactacttta aaaataaagt tgatctcttt     600
tcagttcacc ccacgagtgg tgtcatctcc ttaagtggtc gattaaatta tgatgaaaag     660
aataggtatg atctggaaat tttggctgtg gaccggggaa tgaaactgta tgggaacaat     720
ggagtgagca gtactgcaaa gctttatgtt cacattgagc gcataaatga acatgcccca     780
acaatccatg tagtcactca tgttcctttc tcgttggaaa aagagccaac atatgcagtg     840
gtgacagttg atgacttaga tgatggagcg aatggagaga tcgaatctgt ttccattgtg     900
gctgggatc tttagatca gttcttcctg gctaaggaag aaagtggttt gaatgagtac     960
aagattaagg agaggaagca gattgactgg gagagctttc cctatggcta caatctcact    1020
cttcaagcaa aagacaaggg atctcctcaa aaatgttcag cattaaaggc agtctacatt    1080
ggcaaccca caagagacac tgtccccatt agatttgaaa agaagtgta cgatgtgagc    1140
ataagtgaat tttcccctcc tggtgtcgtg gttgctatag taaaattaag tcctgaaccg    1200
atagatgtga aatacaaatt atctcctggt gaggatgcag tgtactttaa attaatcct    1260
cggtcgggtc tgattgttac agcacggcca ctgaatactg ttaagaagga ggtttataaa    1320
ctggaggtga caaacaagga aggagattta aaagcacagg tcaccatcag catagaagat    1380
gcaaatgacc acacccccaga atttcagcaa ccactgtatg atgcttatgt gaatgaaagt    1440
gtcccagtgg aaccagcgt tctaacagtt tcagcttctg ataaggataa aggagaaaat    1500
gggtacatca cctatagtat cgctagcctg aatttgttac catttgtcat taatcagttt    1560
acaggtgtta ttagcacaac tgaagaactg gattttgaat cctccccaga aatttacaga    1620
ttcattgtta gagcctctga ctgggggttca ccataccgcc atgaaagtga ggtcaatgtg    1680
```

-continued

```
actattcgaa taggaaatgt caacgacaac agccctctct ttgaaaaagt ggcttgccag    1740
ggagttattt catatgactt tccagttggt ggtcacatca cagcagtctc agcgatcgat    1800
atcgatgaac ttgaacttgt aaagtacaaa atcatttctg gaaatgaact tggcttcttt    1860
tatttaaacc cagattctgg tgttttacag cttaaaaaat cactgacaaa ttctggcatt    1920
aaaaatggca ttttgccct cagaattaca gcaactgatg gagagaatct gcagacccc     1980
atgtctatta acatttcagt cctacatggg aaagtgtctt caaagagctt cagttgcaga    2040
gaaactcgtg tggctcaaaa gctggcagag aaactactca ttaaggcaaa gcaaatggg     2100
aaactgaatc tggaagatgg atttcttgac ttttattcaa ttaatagaca gggaccatat    2160
tttgacaagt cttttccttc tgatgtggct gtaaaggagg atctgccagt tggtgctaac    2220
attctgaaga ttaaagccta tgatgccgac tctggcttca atggaaaagt gctatttaca    2280
atatcagatg gaaatacgga tagttgcttt aatattgata tggagactgg gcagcttaaa    2340
gtccttatgc ccatggatcg agaacacaca gacctctatc tccttaatat caccatctat    2400
gacttaggta atccacagaa atcgtcatgg agactgctga ccatcaatgt ggaggatgct    2460
aatgacaata gcccagtttt tattcaagac agttactcag ttaacattct gaaagttca    2520
ggcattggta ctgaaatcat tcaagtggaa gccagagaca agacttagg ttctaatggt    2580
gaagtgactt actcagtctt gacagataca cagcagtttg ccatcaatag ctcaactgga    2640
atcgtttatg tagccgacca gttggaccgg gaatccaaag ccaattattc tttgaaaata    2700
gaagccaggg acaaggcaga gagtggtcag cagctgtttt cagttgtcac tcttaaagtt    2760
tttttagatg atgtcaatga ctgctcccca gctttcattc ccagtagcta tagtgtgaag    2820
gttcttgaag atctccctgt tggcactgtc attgcttggc ttgagaccca tgatccagat    2880
cttggactgg ggggtcaagt gcgctattct ttggtcaatg actataatgg gagatttgaa    2940
atagataaag caagtggtgc catccgcttg agcaaagagc ttgattatga gaaacagcag    3000
ttctataacc ttactgtgcg ggccaaagac aaagggcggc ctgtctctct gtcatctgtt    3060
tcctttgttg aggtggaagt ggtggatgtc aatgaaaacc tccacactcc ctatttccca    3120
gactttgctg ttgttggatc tgtaaaggaa aactcacgca ttggaacaag cgtgctgcag    3180
gtgactgctc gagatgaaga ctccggaagg gatggagaga tccagtactc catcagggat    3240
ggcagtggtc ttggaaggtt cagtatagac gacgagagtg gggtcatcac tgccgcagac    3300
attcttgatc gggagacaat ggggtcatac tggctaacag tgtatgccac agacaggggc    3360
gttgttccac tctactccac cattgaggtc tacattgaag ttgaagatgt gaatgacaat    3420
gccccgctga cctcagaacc tatatattat cctgttgtca tggaaaactc tccaaaggac    3480
gtatctgtca ttcagatcca ggctgaagat cctgactcca gttccaatga aaaactgaca    3540
tacaggatta caagtggaaa tcctcagaat ttttttgcca tcaatatcaa aacaggtctg    3600
attacaacaa cttcaaggaa attggatcga gaacagcagg cagaacattt tctggaggtg    3660
actgtgacag atggtggtcc ctctccaaaa cagtcaacca tttgggtggt ggttcaggtt    3720
ctagatgaaa atgacaacaa gccccagttc ccagagaagg tctaccagat caagctgcca    3780
gaacgtgacc gaaagaagag aggagaaccg atttacaggg cttttgcatt tgatagagat    3840
gagggcccca acgcagaaat ctcctacagt attgtggatg gaatgatga cggaaagttc    3900
tttattgacc ctaaaactgg gatggttctt tctagaaagc agtttacagc aggcagttat    3960
gacatcctaa cgataaaggc agtggacaat gggcgcccac agaaatcctc cacggcccgc    4020
```

-continued

| | |
|---|---|
| ctccacattg aatggattaa gaaaccaccc ccttcaccta taccattgac cttcgatgag | 4080 |
| ccgttttata acttcacagt catggaaagt gatagagtga ctgaaattgt agggtggtg | 4140 |
| tctgtgcagc cagctaacac ccctctgtgg tttgacatag ttgggggaa ttttgacagc | 4200 |
| gcttttgatg cagagaaggg tgttgggaca attgtcatcg caaaacctt ggatgcagag | 4260 |
| cagaggtcca tctataatat gagtgtggaa gtcaccgatg gacaaatgt tgctgttact | 4320 |
| caggtattta tcaaagtgct ggataataat gataatggcc cagaattctc tcagccgaat | 4380 |
| tacgatgtga caatttccga ggatgtgctt ccagacacgg agatcctgca gattgaagcc | 4440 |
| acagatagag atgagaagca caagctgagc tacactgttc atagcagcat cgactccatc | 4500 |
| agcatgagaa aattccggat tgaccctagc actggcgtgc tctatactgc cgagaggctg | 4560 |
| gaccatgagg cccaggacaa gcacattctc aacataatgg tcagagatca ggagtttcct | 4620 |
| tatcgaagaa acttggcccg agtcattgtg aatgtggagg atgctaatga tcacagtcct | 4680 |
| tattttacca acccactgta tgaagcgtct gtgtttgaat ctgctgctct gggatcagct | 4740 |
| gttctgcaag tgacggctct ggacaaagac aaaggagaaa atgcagaact catatatacc | 4800 |
| atagaagcag gaacactgg gaacatgttt aagatcgaac cggtcctagg catcatcacc | 4860 |
| atttgcaaag aaccagacat gacgacgatg ggtcagtttg tcctatccat caaagtcaca | 4920 |
| gatcagggat cccgccaat gtctgctact gcaattgtgc gcatttccgt caccatgtct | 4980 |
| gacaattctc accccaagtt cattcacaaa gactaccaag cagaagtaaa tgaaaatgtt | 5040 |
| gacattggaa catcagtcat tctaatctct gccatcagtc aatctaccct catttatgaa | 5100 |
| gtcaaagatg gagacattaa tgggatcttt accataaatc catattctgg agtcatcacc | 5160 |
| actcagaagg ccctggatta tgagcgcaca tcctcttatc aactcatcat tcaggccacc | 5220 |
| aatatggcag gaatggcttc caatgctaca gtcaatattc agattgttga tgaaaatgat | 5280 |
| aatgccccag ttttctctt ttctcaatac tcaggcagcc taagtgaggc tgccccaatt | 5340 |
| aatagcattg tcaggagctt ggataacagc ccactggtga ttcgagccac agatgctgac | 5400 |
| agcaaccgga atgctctgct tgtgtatcag attgtggagt caacagcaaa aaagtttttc | 5460 |
| acggtggact ccagtacagg tgcaatcaga acaattgcca acctggacca tgaaaccatt | 5520 |
| gcccatttcc attttcatgt gcatgtgaga gacagtggta gccccaact gactgcagag | 5580 |
| agtcccgttg aagtcaacat tgaggtgaca gatgtgaatg ataacccacc tgttttact | 5640 |
| caggctgtgt ttgagactat cttacttcta cctacctatg ttggagtgga ggttctgaaa | 5700 |
| gttagtgcca cagatcctga ctctgaggta ccccctgaac tgacatacag cctaatggaa | 5760 |
| ggcagtttgg atcatttttt aattgactca acagtggag tacttaccat aaaaaacaac | 5820 |
| aacctctcca aggatcacta catgctgata gttaaggtgt ctgatggaaa gttctacagt | 5880 |
| acctccatgg tcaccatcat ggttaaagaa gccatggaca gcggcctcca ctttacacaa | 5940 |
| agcttctatt ccacctcaat ctcagagaac aacactaaca taaccaaagt tgctattgtc | 6000 |
| aatgcagttg gaaatcgcct taatgagccc ttaaaataca gcatcttaaa cccaggaaat | 6060 |
| aagttcaaga taaatctac ctcaggggtc attcagacga ctggagtccc ctttgaccgt | 6120 |
| gaagaacaag agttatatga gctggtggta gaagccagcc gtgagctgga ccatctgcgt | 6180 |
| gtggccagag tggtggtcag ggttaacatt gaagacataa atgacaattc tccagtctt | 6240 |
| gtgggcctcc atactatgc tgctgttcaa gtggatgcgg aacccgggac tctgatttat | 6300 |
| caggtgacag ccattgacaa agataaaggt ccaaatggag aagtgaccta tgtcctgcag | 6360 |
| gatgactatg ccactttga aattaaccct aattcaggga atgttatttt aaaggaagca | 6420 |

-continued

```
ttcaactctg acttgtccaa cattgagtat ggagtcacca tcctagccaa ggatggcgga    6480
aaaccttctt tgtctacatc tgtggagctt cccatcacta ttgtcaacaa agcaatgcct    6540
gtgtttgata agcccttta tacagcatct gtcaatgaag acatcagaat gaacacaccc    6600
atcctaagca tcaatgccac cagtccagaa ggccaaggca tcatatatat cattatcgat    6660 gtggacccctt ttaaacagtt taacattgac tttgacactg gggtcctgaa agttgttagc    6720
cctttggatt atgaagttac atctgcttac aagctgacaa taagagccag cgacgccctt    6780
actggtgcta gggctgaagt cactgttgac ttgctagtta atgatgtaaa tgacaaccc    6840 cctatttcg atcagcctac atacaataca acactatcag aagcatctct tattgggaca    6900
cctgttttac aagttgtctc tattgatgca gactcagaaa acaataaaat ggtacattat    6960
cagattgtcc aggatacctat caatagcaca gattattttc acatagatag ctcaagtggc    7020
ttaatcctga cagcacgaat gctgaccat gagttagtac aacactgcac tttgaaagtc    7080
agatcaatag atagtggctt cccatcactg agcagtgagg ttctcgttca tatctacatc    7140
tctgatgtaa atgacaaccc tccagttttt aatcagctca tttatgagtc atatgtgagt    7200
gaattagccc cccggggcca ttttgtaacc tgtgtacaag cctctgatgc agacagctct    7260
gattttgacc ggttggaata tagcattta tctgggaatg accggacgag ctttctgatg    7320
gacagcaaga gtggagttat cacattgtcc aaccatcgga agcagcggat ggagcctctg    7380
tacagtctca atgtgtctgt ctctgatggg ttgttcacca gcactgcaca ggtgcatatt    7440
agggtacttg gggctaactt gtacagccct gccttttcac aaagcacata cgtagctgag    7500
gtgagagaga acgtggctgc aggaacaaag gtaattcatg ttcgagccac agatggtgat    7560
ccagggactt atgggcagat cagctatgcc atcatcaatg actttgccaa ggatcgattc    7620
ctcatagaca gcaatgggca ggtcatcacc acagaaaggc tagaccggga aaaccctcta    7680 gaagggatg ttagtatttt tgtgagggcc ttgatggtg gagggagaac aactttctgc    7740
actgtgagag tgattgttgt ggatgaaaat gacaatgctc cccagttcat gacagtggaa    7800
tatagagcca gtgtcagggc agatgttgga agggccact tggtcactca agttcaagcc    7860
atagatcccg atgatggagc aaattcaagg attacttatt ccctctatag cgaggcctct    7920
gtttcagtgg ccgacctcct ggaaatcgat cctgacaatg gctggatggt cacaaagggt    7980
aattttaacc agctgaaaaa tacagtgctt tcgttctttg tcaaagcagt gatgggggc    8040 atcccagtaa agcactccct cattcctgtc tatatccacg tcttgccccc tgaaacgttc    8100
ttgccatcat tcacccagtc tcagtattcc tttaccattg cagaagatac agccattggg    8160
agtacagtgg acaccctgag gatttttgccc agtcagaatg tctggttcag cacagttaat    8220
ggggaacggc cagaaaataa caaggggc gtattcgtca tagaacagga acaggcact    8280 attaagcttg acaaacgcct tgaccgtgaa accagcccag ctttccactt taaagtagca    8340
gccactatac ccctggacaa agtagacatt gtgtttactg tggatgtaga tatcaaggta    8400
ttggatttga atgacaacaa gccagtcttt gaaacttcaa gctatgacac cattataatg    8460
gaagggatgc ctgttggcac caaactcaca caagtgagag ctattgatat ggactgggga    8520
gccaatggac aagtcactta ctccctccac tcggattccc agccccgaaaa ggtaatggaa    8580 gcattcaata ttgacagcaa cacgggctgg atcagtacct tgaaggacct agatcacgag    8640 acagaccca cattcacctt ctctgtggtg gcctctgacc ttggagaggc attctctctt    8700
tcctccacgg ccttggtctc tgtcagagtg acagatataa atgacaatgc accagtcttc    8760
```

```
gcgcaggaag tgtaccgagg gaatgtgaag gagagcgacc caccgggcga ggtggtagcc    8820
gtcctcagca cctgggacag agacacatcc gacgttaatc gccaagtgag ctaccatatt    8880
acaggaggaa accctcgagg aaggtttgct ctgggcctgg tgcaaagtga gtggaaggtc    8940
tatgtgaaga ggcctctaga cagagaagaa caggacattt actttctcaa tatcactgcc    9000
actgatgggc tttttgtcac acaggccatg gtggaagtga gcgtcagtga tgtgaatgac    9060
aatagcccag tgtgtgatca ggttgcatat acagcattac ttcctgaaga cattccatca    9120
aataaaatca tcctgaaagt cagtgcaaag gatgctgata ttggatccaa tggatatata    9180
cgatactcac tctatggatc tggaaacagt gaattttttc tagatccaga aagtggcgag    9240
ttaaaaacct tggctctgtt ggaccgggag aggatccccg tgtacagcct gatggccaag    9300
gccactgacg ggggtggcag gttctgccag tccaacatcc acctaatcct ggaggatgtg    9360
aatgataacc cccctgtgtt ttcttctgac cactacaaca cctgtgtcta tgagaacaca    9420
gccaccaagg ctctgttgac cagagttcaa gccgtggacc ccgacattgg catcaatagg    9480
aaggtcgtgt actccctggc agactcagct ggtggggtct tctccattga cagctcatct    9540
ggcatcatca tcctggagca gccactggac cgtgagcagc agtcttcgta caacatcagc    9600
gtgcgggcca ctgaccagag tcctggacag tccctgtcct ctctcactac tgtcaccatc    9660
accgttctgg acattaatga caacccccct gtgtttgaga ggagggacta cctggtgacg    9720
gtgcctgagg acacctcccc tggcacccaa gtccttgctg tttttgccac cagcaaagat    9780
attggcacaa atgctgagat cacttatctc atccggtctg ggaacgaaca agggaaattt    9840
aagatcaacc ccaagacagg gggtatttct gtctctgaag tcctggacta tgaattatgc    9900
aaaaggtttt acctggtagt ggaagccaaa gatgggggca ccccagctct cagcgctgtg    9960
gccactgtca acatcaacct cacagatgtt aatgacaacc ctcccaagtt cagccaagac    10020
gtctacagtg cggttatcag tgaagacgcc ttggtgggag actctgtcat tttgctaata    10080
gcagaagatg tagacagcca gcccaacgga cagattcatt tttccattgt gaatggagat    10140
cgggacaatg aatttactgt agatcctgtc ttgggacttg tgaaagttaa gaagaaattg    10200
gaccgggaac gggtgtctgg atactctctg cttgtccagg ccgtagacag tggcattcct    10260
gcaatgtcat caactgcaac tgtcaacatt gatatttctg atgtgaatga caacagcccg    10320
gtgtttacac ctgccaacta tactgctgtg attcaggaaa ataagccagt gggcaccagc    10380
atcttgcagc tggtggtgac agacagagac tcctttcaca atgggcctcc cttttcattc    10440 tctatttttgt cgggaaatga agaggaggag tttgtgttgg accctcatgg gatcttgcgg    10500
tcggctgtgg tcttccagca cacagagtct ctggaatacg tgttgtgtgt ccaggcaaag    10560
gattcaggca acccccagca gtttctcac acttacatcc gcgtgcgagt cattgaggaa    10620
agcacccaca gcccacagc cattcccctg gaaattttca ttgtcaccat ggaggatgac    10680
tttcctggtg gggtcattgg gaagattcat gccacagatc aagacatgta tgatgtgctc    10740
acatttgccc tgaaatcgga gcagaaaagc ttatttaaag tgaacagtca cgatgggaaa    10800
atcatcgccc tggaggcct ggacagcggc aagtatgtcc tgaatgtgtc tgtgagtgat    10860
ggtcgcttcc aggtacccat tgatgtggtc gtgcatgtgg agcagttggt gcatgagatg    10920
ctgcagaaca ctgtcaccat ccgctttgaa aatgtgtccc ctgaggactt cgtggggctg    10980
cacatgcatg ggttccggcg cacccctgcgg aatgcagtcc tcacccagaa gcaggacagc    11040
ctgcgcatca tcagcatcca gcccgtggca ggcaccaacc aactggacat gctgtttgcg    11100
gtggagatgc acagcagcga gttctacaag ccagcctacc tgatccagaa gctgtccaat    11160
```

```
gctagaagac acctggagaa tatcatgcgc atctcagcca tcttggagaa gaactgctca   11220
gggctggact gtcaggaaca gcattgtgag caaggcttgt cactcgattc ccacgcgctc   11280
atgacctaca gcacggctcg catcagcttt gtgtgtccgc gtttctacag gaacgtgcgt   11340
tgcacctgca atggaggact gtgtccgggg tccaacgatc cttgtgtgga gagccgtgt    11400 ccagggggaca tgcagtgtgt cggttatgaa gccagcagga gaccgttcct ctgccagtgt   11460
ccaccaggga agctcggaga gtgctcaggg cacacttctc tcagctttgc tggaaacagt   11520
tacatcaaat atcggctttc tgaaaatagc aagaagagg atttcaaact agctctgcgt    11580
cttcgaacac tgcaaagcaa tgggattata atgtacacca gagcaaatcc ctgcataatt   11640
ctgaagattg tggatggcaa gctgtggttc cagctggact gcggcagcgg ccctggaatc   11700
ttgggcatct cgggccgtgc tgtcaacgac gggagctggc actcggtctt cctggagctc   11760
aaccgcaatt tcacgagcct gtccctggat acagctacg tggagcggcg ccgggcgccc    11820
ctctacttcc agacgctgag cactgagagt agcatctact tcggcgccct ggtgcaagcg   11880
gataacatcc gcagcctgac tgacacgcgg gtcacgcagg tgctcagcgg cttccagggc   11940
tgcctggact cggtgatact gaataacaat gagctgccgc tgcagaacaa gcgcagcagc   12000
ttcgcggagg tggtgggcct gacggagctg aagctgggct gcgtgctcta tcccgacgcc   12060
tgcaagcgca gcccgtgcca gcacgggggc agctgcactg gcctgccatc gggggggctat   12120 cagtgtacct gtctctcaca gtttacgggg agaaactgtg aatctgagat tacagcctgc   12180
ttcccaaacc cctgccggaa tggaggatcc tgcgatccaa taggaaacac tttcatctgc   12240
aattgtaaag ctgggctcac tggagtcacg tgtgaggagg acatcaatga gtgcgaacga   12300
gaggagtgtg agaacggagg ctcctgcgtg aacgtgttcg gctccttcct ctgcaactgc   12360
acgccgggct acgtgggcca gtactgcggg ctgcgccccg tggtggtacc caatatccag   12420
gctggccact cctacgtggg gaaggaggag ctcatcggca tcgccgtggt cctcttcgtc   12480
atcttcatcc tggtggttct cttcatagtc ttccgcaaga aggtcttccg caagaactac   12540
tcccgcaaca catcacgct agtgcaggac ccggccaccg ccgccctgct aacaagagc    12600 aatggcatcc cgttccggaa cctgcgcggc agtggggacg gccgcaacgt ctaccaggag   12660
gtggggcccc cgcaggtccc cgtgcgcccc atggcctaca cccctgctt ccagagtgac    12720 tccaggagca acctggataa gatcgtggac gggctgggag gcgagcacca ggaaatgacc   12780
acgtttcacc ctgagtcgcc ccgcatcctg acagcccggc ggggcgtggt cgtgtgcagt   12840 gtggcccca acctccccgc cgtgtcaccc tgccgctccg actgcgactc catccggaag   12900
aatggctggg acgcgggaac tgagaacaaa ggggttgatg acccgggaga gtgacctgc    12960 tttgcaggta gtaataaagg cagcaactct gaagttcagt ccctcagctc cttccagtca   13020
gattctggtg acgacaatgc ctccatagtg actgtcattc agcttgtcaa caatgtagtt   13080
gacactatag agaatgaagt gtctgtcatg gaccaaggac agaactacaa ccgagcctat   13140
cactgggaca cctctgattg gatgccaggg gcccgcctgt cggacataga ggaagtgccc   13200
aactatgaga accaggatgg agggtctgca caccaggggga gcacacggga gctggagagc   13260
gattactacc tgggtggtta tgacattgac agtgaatacc cacccctca tgaagaggag    13320 ttcttgagtc aggaccagct gcctcctcct ctcccggagg acttcccaga ccaatatgag   13380
gccctgccac cctcccagcc tgtctcccctg gccagcacac tgagcccaga ctgcaggaga   13440
aggccccagt ttcatcctag ccagtatctc cctcctcacc cattcccaa cgaaacggat   13500
```

-continued

```
ttggtgggcc cgcctgccag ctgtgaattt agtactttg ctgtgagcat gaaccagggc      13560
acagagccca caggcccagc agacagcgtg tctctgtcct tgcacaattc cagaggcacc      13620
tcatcctcgg atgtgtctgc caactgcggc tttgacgatt ccgaagtagc catgagtgac      13680
tacgagagcg tgggagagct cagcctcgcc agccttcaca ttccctttgt ggagactcag      13740
catcagactc aagtgtag                                                    13758
```

```
<210> SEQ ID NO 6
<211> LENGTH: 4585
<212> TYPE: PRT
<213> ORGANISM: homo sapiens

<400> SEQUENCE: 6
```

| | | | | | | | | | | | | | | |
|---|---|---|---|---|---|---|---|---|---|---|---|---|---|---|
| Met | Gly | His | Cys | Val | Gly | Thr | Arg | Pro | Pro | Ala | Cys | Cys | Leu | Ile | Leu |
| 1 | | | | 5 | | | | | 10 | | | | | 15 | |

| Leu | Leu | Phe | Lys | Leu | Leu | Ala | Thr | Val | Ser | Gln | Gly | Leu | Pro | Gly | Thr |
|---|---|---|---|---|---|---|---|---|---|---|---|---|---|---|---|
| | | | 20 | | | | | 25 | | | | | 30 | | |

| Gly | Pro | Leu | Gly | Phe | His | Phe | Thr | His | Ser | Ile | Tyr | Asn | Ala | Thr | Val |
|---|---|---|---|---|---|---|---|---|---|---|---|---|---|---|---|
| | | | 35 | | | | | 40 | | | | | 45 | | |

| Tyr | Glu | Asn | Ser | Ala | Ala | Arg | Thr | Tyr | Val | Asn | Ser | Gln | Ser | Arg | Met |
|---|---|---|---|---|---|---|---|---|---|---|---|---|---|---|---|
| | 50 | | | | | 55 | | | | | 60 | | | | |

| Gly | Ile | Thr | Leu | Ile | Asp | Leu | Ser | Trp | Asp | Ile | Lys | Tyr | Arg | Ile | Val |
|---|---|---|---|---|---|---|---|---|---|---|---|---|---|---|---|
| 65 | | | | | 70 | | | | | 75 | | | | | 80 |

| Ser | Gly | Asp | Glu | Glu | Gly | Phe | Phe | Lys | Ala | Glu | Val | Ile | Ile | Ala |
|---|---|---|---|---|---|---|---|---|---|---|---|---|---|---|
| | | | | 85 | | | | | 90 | | | | | 95 |

| Asp | Phe | Cys | Phe | Leu | Arg | Ile | Arg | Thr | Lys | Gly | Gly | Asn | Ser | Ala | Ile |
|---|---|---|---|---|---|---|---|---|---|---|---|---|---|---|---|
| | | | 100 | | | | | 105 | | | | | 110 | | |

| Leu | Asn | Arg | Glu | Ile | Gln | Asp | Asn | Tyr | Leu | Leu | Ile | Val | Lys | Gly | Ser |
|---|---|---|---|---|---|---|---|---|---|---|---|---|---|---|---|
| | | | 115 | | | | | 120 | | | | | 125 | | |

| Val | Arg | Gly | Glu | Asp | Leu | Glu | Ala | Trp | Thr | Lys | Val | Asn | Ile | Gln | Val |
|---|---|---|---|---|---|---|---|---|---|---|---|---|---|---|---|
| | | 130 | | | | | 135 | | | | | 140 | | | |

| Leu | Asp | Met | Asn | Asp | Leu | Arg | Pro | Leu | Phe | Ser | Pro | Thr | Thr | Tyr | Ser |
|---|---|---|---|---|---|---|---|---|---|---|---|---|---|---|---|
| 145 | | | | | 150 | | | | | 155 | | | | | 160 |

| Val | Thr | Ile | Ala | Glu | Ser | Thr | Pro | Leu | Arg | Thr | Ser | Val | Ala | Gln | Val |
|---|---|---|---|---|---|---|---|---|---|---|---|---|---|---|---|
| | | | | 165 | | | | | 170 | | | | | 175 | |

| Thr | Ala | Thr | Asp | Ala | Asp | Ile | Gly | Ser | Asn | Gly | Glu | Phe | Tyr | Tyr | Tyr |
|---|---|---|---|---|---|---|---|---|---|---|---|---|---|---|---|
| | | | 180 | | | | | 185 | | | | | 190 | | |

| Phe | Lys | Asn | Lys | Val | Asp | Leu | Phe | Ser | Val | His | Pro | Thr | Ser | Gly | Val |
|---|---|---|---|---|---|---|---|---|---|---|---|---|---|---|---|
| | | 195 | | | | | 200 | | | | | 205 | | | |

| Ile | Ser | Leu | Ser | Gly | Arg | Leu | Asn | Tyr | Asp | Glu | Lys | Asn | Arg | Tyr | Asp |
|---|---|---|---|---|---|---|---|---|---|---|---|---|---|---|---|
| | 210 | | | | | 215 | | | | | 220 | | | | |

| Leu | Glu | Ile | Leu | Ala | Val | Asp | Arg | Gly | Met | Lys | Leu | Tyr | Gly | Asn | Asn |
|---|---|---|---|---|---|---|---|---|---|---|---|---|---|---|---|
| 225 | | | | | 230 | | | | | 235 | | | | | 240 |

| Gly | Val | Ser | Ser | Thr | Ala | Lys | Leu | Tyr | Val | His | Ile | Glu | Arg | Ile | Asn |
|---|---|---|---|---|---|---|---|---|---|---|---|---|---|---|---|
| | | | | 245 | | | | | 250 | | | | | 255 | |

| Glu | His | Ala | Pro | Thr | Ile | His | Val | Thr | His | Val | Pro | Phe | Ser | Leu |
|---|---|---|---|---|---|---|---|---|---|---|---|---|---|---|
| | | | 260 | | | | | 265 | | | | | 270 | |

| Glu | Lys | Glu | Pro | Thr | Tyr | Ala | Val | Val | Thr | Val | Asp | Asp | Leu | Asp | Asp |
|---|---|---|---|---|---|---|---|---|---|---|---|---|---|---|---|
| | | | 275 | | | | | 280 | | | | | 285 | | |

| Gly | Ala | Asn | Gly | Glu | Ile | Glu | Ser | Val | Ser | Ile | Val | Ala | Gly | Asp | Pro |
|---|---|---|---|---|---|---|---|---|---|---|---|---|---|---|---|
| | | | 290 | | | | | 295 | | | | | 300 | | |

| Leu | Asp | Gln | Phe | Phe | Leu | Ala | Lys | Glu | Gly | Lys | Trp | Leu | Asn | Glu | Tyr |
|---|---|---|---|---|---|---|---|---|---|---|---|---|---|---|---|
| 305 | | | | | 310 | | | | | 315 | | | | | 320 |

| Lys | Ile | Lys | Glu | Arg | Lys | Gln | Ile | Asp | Trp | Glu | Ser | Phe | Pro | Tyr | Gly |
|---|---|---|---|---|---|---|---|---|---|---|---|---|---|---|---|

-continued

```
                325                 330                 335
Tyr Asn Leu Thr Leu Gln Ala Lys Asp Lys Gly Ser Pro Gln Lys Cys
            340                 345                 350
Ser Ala Leu Lys Ala Val Tyr Ile Gly Asn Pro Thr Arg Asp Thr Val
            355                 360                 365
Pro Ile Arg Phe Glu Lys Glu Val Tyr Asp Val Ser Ile Ser Glu Phe
        370                 375                 380
Ser Pro Pro Gly Val Val Ala Ile Val Lys Leu Ser Pro Glu Pro
385                 390                 395                 400
Ile Asp Val Glu Tyr Lys Leu Ser Pro Gly Glu Asp Ala Val Tyr Phe
            405                 410                 415
Lys Ile Asn Pro Arg Ser Gly Leu Ile Val Thr Ala Arg Pro Leu Asn
        420                 425                 430
Thr Val Lys Lys Glu Val Tyr Lys Leu Glu Val Thr Asn Lys Glu Gly
            435                 440                 445
Asp Leu Lys Ala Gln Val Thr Ile Ser Ile Glu Asp Ala Asn Asp His
    450                 455                 460
Thr Pro Glu Phe Gln Gln Pro Leu Tyr Asp Ala Tyr Val Asn Glu Ser
465                 470                 475                 480
Val Pro Val Gly Thr Ser Val Leu Thr Val Ser Ala Ser Asp Lys Asp
            485                 490                 495
Lys Gly Glu Asn Gly Tyr Ile Thr Tyr Ser Ile Ala Ser Leu Asn Leu
            500                 505                 510
Leu Pro Phe Val Ile Asn Gln Phe Thr Gly Val Ile Ser Thr Thr Glu
        515                 520                 525
Glu Leu Asp Phe Glu Ser Ser Pro Glu Ile Tyr Arg Phe Ile Val Arg
    530                 535                 540
Ala Ser Asp Trp Gly Ser Pro Tyr Arg His Glu Ser Glu Val Asn Val
545                 550                 555                 560
Thr Ile Arg Ile Gly Asn Val Asn Asp Asn Ser Pro Leu Phe Glu Lys
            565                 570                 575
Val Ala Cys Gln Gly Val Ile Ser Tyr Asp Phe Pro Val Gly Gly His
            580                 585                 590
Ile Thr Ala Val Ser Ala Ile Asp Ile Asp Glu Leu Glu Leu Val Lys
        595                 600                 605
Tyr Lys Ile Ile Ser Gly Asn Glu Leu Gly Phe Phe Tyr Leu Asn Pro
    610                 615                 620
Asp Ser Gly Val Leu Gln Leu Lys Lys Ser Leu Thr Asn Ser Gly Ile
625                 630                 635                 640
Lys Asn Gly Asn Phe Ala Leu Arg Ile Thr Ala Thr Asp Gly Glu Asn
            645                 650                 655
Leu Ala Asp Pro Met Ser Ile Asn Ile Ser Val Leu His Gly Lys Val
            660                 665                 670
Ser Ser Lys Ser Phe Ser Cys Arg Glu Thr Arg Val Ala Gln Lys Leu
        675                 680                 685
Ala Glu Lys Leu Leu Ile Lys Ala Lys Ala Asn Gly Lys Leu Asn Leu
    690                 695                 700
Glu Asp Gly Phe Leu Asp Phe Tyr Ser Ile Asn Arg Gln Gly Pro Tyr
705                 710                 715                 720
Phe Asp Lys Ser Phe Pro Ser Asp Val Ala Val Lys Glu Asp Leu Pro
            725                 730                 735
Val Gly Ala Asn Ile Leu Lys Ile Lys Ala Tyr Asp Ala Asp Ser Gly
            740                 745                 750
```

```
Phe Asn Gly Lys Val Leu Phe Thr Ile Ser Asp Gly Asn Thr Asp Ser
            755                 760                 765

Cys Phe Asn Ile Asp Met Glu Thr Gly Gln Leu Lys Val Leu Met Pro
            770                 775                 780

Met Asp Arg Glu His Thr Asp Leu Tyr Leu Leu Asn Ile Thr Ile Tyr
785             790                 795                     800

Asp Leu Gly Asn Pro Gln Lys Ser Ser Trp Arg Leu Leu Thr Ile Asn
            805                 810                 815

Val Glu Asp Ala Asn Asp Asn Ser Pro Val Phe Ile Gln Asp Ser Tyr
            820                 825                 830

Ser Val Asn Ile Leu Glu Ser Ser Gly Ile Gly Thr Glu Ile Ile Gln
            835                 840                 845

Val Glu Ala Arg Asp Lys Asp Leu Gly Ser Asn Gly Glu Val Thr Tyr
            850                 855                 860

Ser Val Leu Thr Asp Thr Gln Gln Phe Ala Ile Asn Ser Ser Thr Gly
865             870                 875                     880

Ile Val Tyr Val Ala Asp Gln Leu Asp Arg Glu Ser Lys Ala Asn Tyr
                885                 890                 895

Ser Leu Lys Ile Glu Ala Arg Asp Lys Ala Glu Ser Gly Gln Gln Leu
            900                 905                 910

Phe Ser Val Val Thr Leu Lys Val Phe Leu Asp Asp Val Asn Asp Cys
            915                 920                 925

Ser Pro Ala Phe Ile Pro Ser Ser Tyr Ser Val Lys Val Leu Glu Asp
            930                 935                 940

Leu Pro Val Gly Thr Val Ile Ala Trp Leu Glu Thr His Asp Pro Asp
945             950                 955                     960

Leu Gly Leu Gly Gly Gln Val Arg Tyr Ser Leu Val Asn Asp Tyr Asn
                965                 970                 975

Gly Arg Phe Glu Ile Asp Lys Ala Ser Gly Ala Ile Arg Leu Ser Lys
            980                 985                 990

Glu Leu Asp Tyr Glu Lys Gln Gln Phe Tyr Asn Leu Thr Val Arg Ala
            995                 1000                1005

Lys Asp Lys Gly Arg Pro Val Ser Leu Ser Ser Val Ser Phe Val Glu
    1010                1015                1020

Val Glu Val Val Asp Val Asn Glu Asn Leu His Thr Pro Tyr Phe Pro
1025                1030                1035                1040

Asp Phe Ala Val Val Gly Ser Val Lys Glu Asn Ser Arg Ile Gly Thr
                1045                1050                1055

Ser Val Leu Gln Val Thr Ala Arg Asp Glu Asp Ser Gly Arg Asp Gly
            1060                1065                1070

Glu Ile Gln Tyr Ser Ile Arg Asp Gly Ser Gly Leu Gly Arg Phe Ser
            1075                1080                1085

Ile Asp Asp Glu Ser Gly Val Ile Thr Ala Ala Asp Ile Leu Asp Arg
            1090                1095                1100

Glu Thr Met Gly Ser Tyr Trp Leu Thr Val Tyr Ala Thr Asp Arg Gly
1105                1110                1115                1120

Val Val Pro Leu Tyr Ser Thr Ile Glu Val Tyr Ile Glu Val Glu Asp
                1125                1130                1135

Val Asn Asp Asn Ala Pro Leu Thr Ser Glu Pro Ile Tyr Tyr Pro Val
            1140                1145                1150

Val Met Glu Asn Ser Pro Lys Asp Val Ser Val Ile Gln Ile Gln Ala
            1155                1160                1165
```

```
Glu Asp Pro Asp Ser Ser Asn Glu Lys Leu Thr Tyr Arg Ile Thr
    1170                1175                1180

Ser Gly Asn Pro Gln Asn Phe Phe Ala Ile Asn Ile Lys Thr Gly Leu
1185                1190                1195                1200

Ile Thr Thr Thr Ser Arg Lys Leu Asp Arg Glu Gln Gln Ala Glu His
                1205                1210                1215

Phe Leu Glu Val Thr Val Thr Asp Gly Gly Pro Ser Pro Lys Gln Ser
            1220                1225                1230

Thr Ile Trp Val Val Gln Val Leu Asp Glu Asn Asp Asn Lys Pro
        1235                1240                1245

Gln Phe Pro Glu Lys Val Tyr Gln Ile Lys Leu Pro Glu Arg Asp Arg
    1250                1255                1260

Lys Lys Arg Gly Glu Pro Ile Tyr Arg Ala Phe Ala Phe Asp Arg Asp
1265                1270                1275                1280

Glu Gly Pro Asn Ala Glu Ile Ser Tyr Ser Ile Val Asp Gly Asn Asp
                1285                1290                1295

Asp Gly Lys Phe Phe Ile Asp Pro Lys Thr Gly Met Val Ser Ser Arg
            1300                1305                1310

Lys Gln Phe Thr Ala Gly Ser Tyr Asp Ile Leu Thr Ile Lys Ala Val
        1315                1320                1325

Asp Asn Gly Arg Pro Gln Lys Ser Ser Thr Ala Arg Leu His Ile Glu
    1330                1335                1340

Trp Ile Lys Lys Pro Pro Pro Ser Pro Ile Pro Leu Thr Phe Asp Glu
1345                1350                1355                1360

Pro Phe Tyr Asn Phe Thr Val Met Glu Ser Asp Arg Val Thr Glu Ile
                1365                1370                1375

Val Gly Val Val Ser Val Gln Pro Ala Asn Thr Pro Leu Trp Phe Asp
            1380                1385                1390

Ile Val Gly Gly Asn Phe Asp Ser Ala Phe Asp Ala Glu Lys Gly Val
        1395                1400                1405

Gly Thr Ile Val Ile Ala Lys Pro Leu Asp Ala Glu Gln Arg Ser Ile
    1410                1415                1420

Tyr Asn Met Ser Val Glu Val Thr Asp Gly Thr Asn Val Ala Val Thr
1425                1430                1435                1440

Gln Val Phe Ile Lys Val Leu Asp Asn Asn Asp Asn Gly Pro Glu Phe
                1445                1450                1455

Ser Gln Pro Asn Tyr Asp Val Thr Ile Ser Glu Asp Val Leu Pro Asp
            1460                1465                1470

Thr Glu Ile Leu Gln Ile Glu Ala Thr Asp Arg Asp Glu Lys His Lys
        1475                1480                1485

Leu Ser Tyr Thr Val His Ser Ser Ile Asp Ser Ile Ser Met Arg Lys
    1490                1495                1500

Phe Arg Ile Asp Pro Ser Thr Gly Val Leu Tyr Thr Ala Glu Arg Leu
1505                1510                1515                1520

Asp His Glu Ala Gln Asp Lys His Ile Leu Asn Ile Met Val Arg Asp
                1525                1530                1535

Gln Glu Phe Pro Tyr Arg Arg Asn Leu Ala Arg Val Ile Val Asn Val
            1540                1545                1550

Glu Asp Ala Asn Asp His Ser Pro Tyr Phe Thr Asn Pro Leu Tyr Glu
        1555                1560                1565

Ala Ser Val Phe Glu Ser Ala Ala Leu Gly Ser Ala Val Leu Gln Val
    1570                1575                1580

Thr Ala Leu Asp Lys Asp Lys Gly Glu Asn Ala Glu Leu Ile Tyr Thr
```

```
                1585                1590                1595                1600
Ile Glu Ala Gly Asn Thr Gly Asn Met Phe Lys Ile Glu Pro Val Leu
                1605                1610                1615

Gly Ile Ile Thr Ile Cys Lys Glu Pro Asp Met Thr Thr Met Gly Gln
                1620                1625                1630

Phe Val Leu Ser Ile Lys Val Thr Asp Gln Gly Ser Pro Pro Met Ser
                1635                1640                1645

Ala Thr Ala Ile Val Arg Ile Ser Val Thr Met Ser Asp Asn Ser His
                1650                1655                1660

Pro Lys Phe Ile His Lys Asp Tyr Gln Ala Glu Val Asn Glu Asn Val
1665                1670                1675                1680

Asp Ile Gly Thr Ser Val Ile Leu Ile Ser Ala Ile Ser Gln Ser Thr
                1685                1690                1695

Leu Ile Tyr Glu Val Lys Asp Gly Asp Ile Asn Gly Ile Phe Thr Ile
                1700                1705                1710

Asn Pro Tyr Ser Gly Val Ile Thr Thr Gln Lys Ala Leu Asp Tyr Glu
                1715                1720                1725

Arg Thr Ser Ser Tyr Gln Leu Ile Ile Gln Ala Thr Asn Met Ala Gly
                1730                1735                1740

Met Ala Ser Asn Ala Thr Val Asn Ile Gln Ile Val Asp Glu Asn Asp
1745                1750                1755                1760

Asn Ala Pro Val Phe Leu Phe Ser Gln Tyr Ser Gly Ser Leu Ser Glu
                1765                1770                1775

Ala Ala Pro Ile Asn Ser Ile Val Arg Ser Leu Asp Asn Ser Pro Leu
                1780                1785                1790

Val Ile Arg Ala Thr Asp Ala Asp Ser Asn Arg Asn Ala Leu Leu Val
                1795                1800                1805

Tyr Gln Ile Val Glu Ser Thr Ala Lys Lys Phe Phe Thr Val Asp Ser
                1810                1815                1820

Ser Thr Gly Ala Ile Arg Thr Ile Ala Asn Leu Asp His Glu Thr Ile
1825                1830                1835                1840

Ala His Phe His Phe His Val His Val Arg Asp Ser Gly Ser Pro Gln
                1845                1850                1855

Leu Thr Ala Glu Ser Pro Val Glu Val Asn Ile Glu Val Thr Asp Val
                1860                1865                1870

Asn Asp Asn Pro Pro Val Phe Thr Gln Ala Val Phe Glu Thr Ile Leu
                1875                1880                1885

Leu Leu Pro Thr Tyr Val Gly Val Glu Val Leu Lys Val Ser Ala Thr
                1890                1895                1900

Asp Pro Asp Ser Glu Val Pro Pro Glu Leu Thr Tyr Ser Leu Met Glu
1905                1910                1915                1920

Gly Ser Leu Asp His Phe Leu Ile Asp Ser Asn Ser Gly Val Leu Thr
                1925                1930                1935

Ile Lys Asn Asn Asn Leu Ser Lys Asp His Tyr Met Leu Ile Val Lys
                1940                1945                1950

Val Ser Asp Gly Lys Phe Tyr Ser Thr Ser Met Val Thr Ile Met Val
                1955                1960                1965

Lys Glu Ala Met Asp Ser Gly Leu His Phe Thr Gln Ser Phe Tyr Ser
                1970                1975                1980

Thr Ser Ile Ser Glu Asn Asn Thr Asn Ile Thr Lys Val Ala Ile Val
1985                1990                1995                2000

Asn Ala Val Gly Asn Arg Leu Asn Glu Pro Leu Lys Tyr Ser Ile Leu
                2005                2010                2015
```

-continued

```
Asn Pro Gly Asn Lys Phe Lys Ile Lys Ser Thr Ser Gly Val Ile Gln
            2020                2025                2030

Thr Thr Gly Val Pro Phe Asp Arg Glu Glu Gln Glu Leu Tyr Glu Leu
            2035                2040                2045

Val Val Glu Ala Ser Arg Glu Leu Asp His Leu Arg Val Ala Arg Val
            2050                2055                2060

Val Val Arg Val Asn Ile Glu Asp Ile Asn Asp Asn Ser Pro Val Phe
2065                2070                2075                2080

Val Gly Leu Pro Tyr Tyr Ala Ala Val Gln Val Asp Ala Glu Pro Gly
            2085                2090                2095

Thr Leu Ile Tyr Gln Val Thr Ala Ile Asp Lys Asp Lys Gly Pro Asn
            2100                2105                2110

Gly Glu Val Thr Tyr Val Leu Gln Asp Asp Tyr Gly His Phe Glu Ile
            2115                2120                2125

Asn Pro Asn Ser Gly Asn Val Ile Leu Lys Glu Ala Phe Asn Ser Asp
            2130                2135                2140

Leu Ser Asn Ile Glu Tyr Gly Val Thr Ile Leu Ala Lys Asp Gly Gly
2145                2150                2155                2160

Lys Pro Ser Leu Ser Thr Ser Val Glu Leu Pro Ile Thr Ile Val Asn
            2165                2170                2175

Lys Ala Met Pro Val Phe Asp Lys Pro Phe Tyr Thr Ala Ser Val Asn
            2180                2185                2190

Glu Asp Ile Arg Met Asn Thr Pro Ile Leu Ser Ile Asn Ala Thr Ser
            2195                2200                2205

Pro Glu Gly Gln Gly Ile Ile Tyr Ile Ile Asp Gly Asp Pro Phe
            2210                2215                2220

Lys Gln Phe Asn Ile Asp Phe Asp Thr Gly Val Leu Lys Val Val Ser
2225                2230                2235                2240

Pro Leu Asp Tyr Glu Val Thr Ser Ala Tyr Lys Leu Thr Ile Arg Ala
            2245                2250                2255

Ser Asp Ala Leu Thr Gly Ala Arg Ala Glu Val Thr Val Asp Leu Leu
            2260                2265                2270

Val Asn Asp Val Asn Asp Asn Pro Pro Ile Phe Asp Gln Pro Thr Tyr
            2275                2280                2285

Asn Thr Thr Leu Ser Glu Ala Ser Leu Ile Gly Thr Pro Val Leu Gln
            2290                2295                2300

Val Val Ser Ile Asp Ala Asp Ser Glu Asn Asn Lys Met Val His Tyr
2305                2310                2315                2320

Gln Ile Val Gln Asp Thr Tyr Asn Ser Thr Asp Tyr Phe His Ile Asp
            2325                2330                2335

Ser Ser Ser Gly Leu Ile Leu Thr Ala Arg Met Leu Asp His Glu Leu
            2340                2345                2350

Val Gln His Cys Thr Leu Lys Val Arg Ser Ile Asp Ser Gly Phe Pro
            2355                2360                2365

Ser Leu Ser Ser Glu Val Leu Val His Ile Tyr Ile Ser Asp Val Asn
            2370                2375                2380

Asp Asn Pro Pro Val Phe Asn Gln Leu Ile Tyr Glu Ser Tyr Val Ser
2385                2390                2395                2400

Glu Leu Ala Pro Arg Gly His Phe Val Thr Cys Val Gln Ala Ser Asp
            2405                2410                2415

Ala Asp Ser Ser Asp Phe Asp Arg Leu Glu Tyr Ser Ile Leu Ser Gly
            2420                2425                2430
```

```
Asn Asp Arg Thr Ser Phe Leu Met Asp Ser Lys Ser Gly Val Ile Thr
        2435                2440                2445

Leu Ser Asn His Arg Lys Gln Arg Met Glu Pro Leu Tyr Ser Leu Asn
        2450                2455                2460

Val Ser Val Ser Asp Gly Leu Phe Thr Ser Thr Ala Gln Val His Ile
2465                2470                2475                2480

Arg Val Leu Gly Ala Asn Leu Tyr Ser Pro Ala Phe Ser Gln Ser Thr
        2485                2490                2495

Tyr Val Ala Glu Val Arg Glu Asn Val Ala Ala Gly Thr Lys Val Ile
        2500                2505                2510

His Val Arg Ala Thr Asp Gly Asp Pro Gly Thr Tyr Gly Gln Ile Ser
        2515                2520                2525

Tyr Ala Ile Ile Asn Asp Phe Ala Lys Asp Arg Phe Leu Ile Asp Ser
        2530                2535                2540

Asn Gly Gln Val Ile Thr Thr Glu Arg Leu Asp Arg Glu Asn Pro Leu
2545                2550                2555                2560

Glu Gly Asp Val Ser Ile Phe Val Arg Ala Leu Asp Gly Gly Gly Arg
        2565                2570                2575

Thr Thr Phe Cys Thr Val Arg Val Ile Val Asp Glu Asn Asp Asn
        2580                2585                2590

Ala Pro Gln Phe Met Thr Val Glu Tyr Arg Ala Ser Val Arg Ala Asp
        2595                2600                2605

Val Gly Arg Gly His Leu Val Thr Gln Val Gln Ala Ile Asp Pro Asp
        2610                2615                2620

Asp Gly Ala Asn Ser Arg Ile Thr Tyr Ser Leu Tyr Ser Glu Ala Ser
2625                2630                2635                2640

Val Ser Val Ala Asp Leu Leu Glu Ile Asp Pro Asp Asn Gly Trp Met
        2645                2650                2655

Val Thr Lys Gly Asn Phe Asn Gln Leu Lys Asn Thr Val Leu Ser Phe
        2660                2665                2670

Phe Val Lys Ala Val Asp Gly Gly Ile Pro Val Lys His Ser Leu Ile
        2675                2680                2685

Pro Val Tyr Ile His Val Leu Pro Pro Glu Thr Phe Leu Pro Ser Phe
        2690                2695                2700

Thr Gln Ser Gln Tyr Ser Phe Thr Ile Ala Glu Asp Thr Ala Ile Gly
2705                2710                2715                2720

Ser Thr Val Asp Thr Leu Arg Ile Leu Pro Ser Gln Asn Val Trp Phe
        2725                2730                2735

Ser Thr Val Asn Gly Glu Arg Pro Glu Asn Asn Lys Gly Gly Val Phe
        2740                2745                2750

Val Ile Glu Gln Glu Thr Gly Thr Ile Lys Leu Asp Lys Arg Leu Asp
        2755                2760                2765

Arg Glu Thr Ser Pro Ala Phe His Phe Lys Val Ala Ala Thr Ile Pro
        2770                2775                2780

Leu Asp Lys Val Asp Ile Val Phe Thr Val Asp Val Asp Ile Lys Val
2785                2790                2795                2800

Leu Asp Leu Asn Asp Asn Lys Pro Val Phe Glu Thr Ser Ser Tyr Asp
        2805                2810                2815

Thr Ile Ile Met Glu Gly Met Pro Val Gly Thr Lys Leu Thr Gln Val
        2820                2825                2830

Arg Ala Ile Asp Met Asp Trp Gly Ala Asn Gly Gln Val Thr Tyr Ser
        2835                2840                2845

Leu His Ser Asp Ser Gln Pro Glu Lys Val Met Glu Ala Phe Asn Ile
```

-continued

```
               2850                2855                2860

Asp Ser Asn Thr Gly Trp Ile Ser Thr Leu Lys Asp Leu Asp His Glu
2865                2870                2875                2880

Thr Asp Pro Thr Phe Thr Phe Ser Val Val Ala Ser Asp Leu Gly Glu
                    2885                2890                2895

Ala Phe Ser Leu Ser Ser Thr Ala Leu Val Ser Val Arg Val Thr Asp
                    2900                2905                2910

Ile Asn Asp Asn Ala Pro Val Phe Ala Gln Glu Val Tyr Arg Gly Asn
                    2915                2920                2925

Val Lys Glu Ser Asp Pro Pro Gly Glu Val Val Ala Val Leu Ser Thr
                    2930                2935                2940

Trp Asp Arg Asp Thr Ser Asp Val Asn Arg Gln Val Ser Tyr His Ile
2945                2950                2955                2960

Thr Gly Gly Asn Pro Arg Gly Arg Phe Ala Leu Gly Leu Val Gln Ser
                    2965                2970                2975

Glu Trp Lys Val Tyr Val Lys Arg Pro Leu Asp Arg Glu Glu Gln Asp
                    2980                2985                2990

Ile Tyr Phe Leu Asn Ile Thr Ala Thr Asp Gly Leu Phe Val Thr Gln
                    2995                3000                3005

Ala Met Val Glu Val Ser Val Ser Asp Val Asn Asp Asn Ser Pro Val
                    3010                3015                3020

Cys Asp Gln Val Ala Tyr Thr Ala Leu Leu Pro Glu Asp Ile Pro Ser
3025                3030                3035                3040

Asn Lys Ile Ile Leu Lys Val Ser Ala Lys Asp Ala Asp Ile Gly Ser
                    3045                3050                3055

Asn Gly Tyr Ile Arg Tyr Ser Leu Tyr Gly Ser Gly Asn Ser Glu Phe
                    3060                3065                3070

Phe Leu Asp Pro Glu Ser Gly Glu Leu Lys Thr Leu Ala Leu Leu Asp
                    3075                3080                3085

Arg Glu Arg Ile Pro Val Tyr Ser Leu Met Ala Lys Ala Thr Asp Gly
                    3090                3095                3100

Gly Gly Arg Phe Cys Gln Ser Asn Ile His Leu Ile Leu Glu Asp Val
3105                3110                3115                3120

Asn Asp Asn Pro Pro Val Phe Ser Ser Asp His Tyr Asn Thr Cys Val
                    3125                3130                3135

Tyr Glu Asn Thr Ala Thr Lys Ala Leu Leu Thr Arg Val Gln Ala Val
                    3140                3145                3150

Asp Pro Asp Ile Gly Ile Asn Arg Lys Val Val Tyr Ser Leu Ala Asp
                    3155                3160                3165

Ser Ala Gly Gly Val Phe Ser Ile Asp Ser Ser Ser Gly Ile Ile Ile
                    3170                3175                3180

Leu Glu Gln Pro Leu Asp Arg Glu Gln Gln Ser Ser Tyr Asn Ile Ser
3185                3190                3195                3200

Val Arg Ala Thr Asp Gln Ser Pro Gly Gln Ser Leu Ser Ser Leu Thr
                    3205                3210                3215

Thr Val Thr Ile Thr Val Leu Asp Ile Asn Asp Asn Pro Pro Val Phe
                    3220                3225                3230

Glu Arg Arg Asp Tyr Leu Val Thr Val Pro Glu Asp Thr Ser Pro Gly
                    3235                3240                3245

Thr Gln Val Leu Ala Val Phe Ala Thr Ser Lys Asp Ile Gly Thr Asn
                    3250                3255                3260

Ala Glu Ile Thr Tyr Leu Ile Arg Ser Gly Asn Glu Gln Gly Lys Phe
3265                3270                3275                3280
```

```
Lys Ile Asn Pro Lys Thr Gly Gly Ile Ser Val Ser Glu Val Leu Asp
            3285                3290                3295

Tyr Glu Leu Cys Lys Arg Phe Tyr Leu Val Val Glu Ala Lys Asp Gly
        3300                3305                3310

Gly Thr Pro Ala Leu Ser Ala Val Ala Thr Val Asn Ile Asn Leu Thr
            3315                3320                3325

Asp Val Asn Asp Asn Pro Pro Lys Phe Ser Gln Asp Val Tyr Ser Ala
        3330                3335                3340

Val Ile Ser Glu Asp Ala Leu Val Gly Asp Ser Val Ile Leu Leu Ile
3345                3350                3355                3360

Ala Glu Asp Val Asp Ser Gln Pro Asn Gly Gln Ile His Phe Ser Ile
            3365                3370                3375

Val Asn Gly Asp Arg Asp Asn Glu Phe Thr Val Asp Pro Val Leu Gly
        3380                3385                3390

Leu Val Lys Val Lys Lys Lys Leu Asp Arg Glu Arg Val Ser Gly Tyr
            3395                3400                3405

Ser Leu Leu Val Gln Ala Val Asp Ser Gly Ile Pro Ala Met Ser Ser
        3410                3415                3420

Thr Ala Thr Val Asn Ile Asp Ile Ser Asp Val Asn Asp Asn Ser Pro
3425                3430                3435                3440

Val Phe Thr Pro Ala Asn Tyr Thr Ala Val Ile Gln Glu Asn Lys Pro
            3445                3450                3455

Val Gly Thr Ser Ile Leu Gln Leu Val Val Thr Asp Arg Asp Ser Phe
        3460                3465                3470

His Asn Gly Pro Pro Phe Ser Phe Ser Ile Leu Ser Gly Asn Glu Glu
            3475                3480                3485

Glu Glu Phe Val Leu Asp Pro His Gly Ile Leu Arg Ser Ala Val Val
        3490                3495                3500

Phe Gln His Thr Glu Ser Leu Glu Tyr Val Leu Cys Val Gln Ala Lys
3505                3510                3515                3520

Asp Ser Gly Lys Pro Gln Gln Val Ser His Thr Tyr Ile Arg Val Arg
            3525                3530                3535

Val Ile Glu Glu Ser Thr His Lys Pro Thr Ala Ile Pro Leu Glu Ile
            3540                3545                3550

Phe Ile Val Thr Met Glu Asp Asp Phe Pro Gly Gly Val Ile Gly Lys
            3555                3560                3565

Ile His Ala Thr Asp Gln Asp Met Tyr Asp Val Leu Thr Phe Ala Leu
            3570                3575                3580

Lys Ser Glu Gln Lys Ser Leu Phe Lys Val Asn Ser His Asp Gly Lys
3585                3590                3595                3600

Ile Ile Ala Leu Gly Gly Leu Asp Ser Gly Lys Tyr Val Leu Asn Val
            3605                3610                3615

Ser Val Ser Asp Gly Arg Phe Gln Val Pro Ile Asp Val Val His
        3620                3625                3630

Val Glu Gln Leu Val His Glu Met Leu Gln Asn Thr Val Thr Ile Arg
            3635                3640                3645

Phe Glu Asn Val Ser Pro Glu Asp Phe Val Gly Leu His Met His Gly
        3650                3655                3660

Phe Arg Arg Thr Leu Arg Asn Ala Val Leu Thr Gln Lys Gln Asp Ser
3665                3670                3675                3680

Leu Arg Ile Ile Ser Ile Gln Pro Val Ala Gly Thr Asn Gln Leu Asp
            3685                3690                3695
```

-continued

```
Met Leu Phe Ala Val Glu Met His Ser Ser Glu Phe Tyr Lys Pro Ala
            3700                3705                3710
Tyr Leu Ile Gln Lys Leu Ser Asn Ala Arg Arg His Leu Glu Asn Ile
            3715                3720                3725
Met Arg Ile Ser Ala Ile Leu Glu Lys Asn Cys Ser Gly Leu Asp Cys
            3730                3735                3740
Gln Glu Gln His Cys Glu Gln Gly Leu Ser Leu Asp Ser His Ala Leu
3745                3750                3755                3760
Met Thr Tyr Ser Thr Ala Arg Ile Ser Phe Val Cys Pro Arg Phe Tyr
            3765                3770                3775
Arg Asn Val Arg Cys Thr Cys Asn Gly Leu Cys Pro Gly Ser Asn
            3780                3785                3790
Asp Pro Cys Val Glu Lys Pro Cys Pro Gly Asp Met Gln Cys Val Gly
            3795                3800                3805
Tyr Glu Ala Ser Arg Arg Pro Phe Leu Cys Gln Cys Pro Pro Gly Lys
            3810                3815                3820
Leu Gly Glu Cys Ser Gly His Thr Ser Leu Ser Phe Ala Gly Asn Ser
3825                3830                3835                3840
Tyr Ile Lys Tyr Arg Leu Ser Glu Asn Ser Lys Glu Glu Asp Phe Lys
            3845                3850                3855
Leu Ala Leu Arg Leu Arg Thr Leu Gln Ser Asn Gly Ile Ile Met Tyr
            3860                3865                3870
Thr Arg Ala Asn Pro Cys Ile Ile Leu Lys Ile Val Asp Gly Lys Leu
            3875                3880                3885
Trp Phe Gln Leu Asp Cys Gly Ser Gly Pro Gly Ile Leu Gly Ile Ser
            3890                3895                3900
Gly Arg Ala Val Asn Asp Gly Ser Trp His Ser Val Phe Leu Glu Leu
3905                3910                3915                3920
Asn Arg Asn Phe Thr Ser Leu Ser Leu Asp Asp Ser Tyr Val Glu Arg
            3925                3930                3935
Arg Arg Ala Pro Leu Tyr Phe Gln Thr Leu Ser Thr Glu Ser Ser Ile
            3940                3945                3950
Tyr Phe Gly Ala Leu Val Gln Ala Asp Asn Ile Arg Ser Leu Thr Asp
            3955                3960                3965
Thr Arg Val Thr Gln Val Leu Ser Gly Phe Gln Gly Cys Leu Asp Ser
            3970                3975                3980
Val Ile Leu Asn Asn Asn Glu Leu Pro Leu Gln Asn Lys Arg Ser Ser
3985                3990                3995                4000
Phe Ala Glu Val Val Gly Leu Thr Glu Leu Lys Leu Gly Cys Val Leu
            4005                4010                4015
Tyr Pro Asp Ala Cys Lys Arg Ser Pro Cys Gln His Gly Gly Ser Cys
            4020                4025                4030
Thr Gly Leu Pro Ser Gly Gly Tyr Gln Cys Thr Cys Leu Ser Gln Phe
            4035                4040                4045
Thr Gly Arg Asn Cys Glu Ser Glu Ile Thr Ala Cys Phe Pro Asn Pro
            4050                4055                4060
Cys Arg Asn Gly Gly Ser Cys Asp Pro Ile Gly Asn Thr Phe Ile Cys
4065                4070                4075                4080
Asn Cys Lys Ala Gly Leu Thr Gly Val Thr Cys Glu Glu Asp Ile Asn
            4085                4090                4095
Glu Cys Glu Arg Glu Glu Cys Glu Asn Gly Gly Ser Cys Val Asn Val
            4100                4105                4110
Phe Gly Ser Phe Leu Cys Asn Cys Thr Pro Gly Tyr Val Gly Gln Tyr
```

-continued

```
                  4115                4120                4125
Cys Gly Leu Arg Pro Val Val Pro Asn Ile Gln Ala Gly His Ser
    4130                4135                4140
Tyr Val Gly Lys Glu Glu Leu Ile Gly Ile Ala Val Val Leu Phe Val
4145                4150                4155                4160
Ile Phe Ile Leu Val Val Leu Phe Ile Val Phe Arg Lys Lys Val Phe
                4165                4170                4175
Arg Lys Asn Tyr Ser Arg Asn Asn Ile Thr Leu Val Gln Asp Pro Ala
            4180                4185                4190
Thr Ala Ala Leu Leu Asn Lys Ser Asn Gly Ile Pro Phe Arg Asn Leu
        4195                4200                4205
Arg Gly Ser Gly Asp Gly Arg Asn Val Tyr Gln Glu Val Gly Pro Pro
    4210                4215                4220
Gln Val Pro Val Arg Pro Met Ala Tyr Thr Pro Cys Phe Gln Ser Asp
4225                4230                4235                4240
Ser Arg Ser Asn Leu Asp Lys Ile Val Asp Gly Leu Gly Gly Glu His
                4245                4250                4255
Gln Glu Met Thr Thr Phe His Pro Glu Ser Pro Arg Ile Leu Thr Ala
            4260                4265                4270
Arg Arg Gly Val Val Val Cys Ser Val Ala Pro Asn Leu Pro Ala Val
        4275                4280                4285
Ser Pro Cys Arg Ser Asp Cys Asp Ser Ile Arg Lys Asn Gly Trp Asp
    4290                4295                4300
Ala Gly Thr Glu Asn Lys Gly Val Asp Pro Gly Glu Val Thr Cys
4305                4310                4315                4320
Phe Ala Gly Ser Asn Lys Gly Ser Asn Ser Glu Val Gln Ser Leu Ser
                4325                4330                4335
Ser Phe Gln Ser Asp Ser Gly Asp Asp Asn Ala Ser Ile Val Thr Val
            4340                4345                4350
Ile Gln Leu Val Asn Asn Val Val Asp Thr Ile Glu Asn Glu Val Ser
        4355                4360                4365
Val Met Asp Gln Gly Gln Asn Tyr Asn Arg Ala Tyr His Trp Asp Thr
    4370                4375                4380
Ser Asp Trp Met Pro Gly Ala Arg Leu Ser Asp Ile Glu Glu Val Pro
4385                4390                4395                4400
Asn Tyr Glu Asn Gln Asp Gly Gly Ser Ala His Gln Gly Ser Thr Arg
                4405                4410                4415
Glu Leu Glu Ser Asp Tyr Tyr Leu Gly Gly Tyr Asp Ile Asp Ser Glu
            4420                4425                4430
Tyr Pro Pro Pro His Glu Glu Phe Leu Ser Gln Asp Gln Leu Pro
        4435                4440                4445
Pro Pro Leu Pro Glu Asp Phe Pro Asp Gln Tyr Glu Ala Leu Pro Pro
    4450                4455                4460
Ser Gln Pro Val Ser Leu Ala Ser Thr Leu Ser Pro Asp Cys Arg Arg
4465                4470                4475                4480
Arg Pro Gln Phe His Pro Ser Gln Tyr Leu Pro Pro His Pro Phe Pro
                4485                4490                4495
Asn Glu Thr Asp Leu Val Gly Pro Ala Ser Cys Glu Phe Ser Thr
            4500                4505                4510
Phe Ala Val Ser Met Asn Gln Gly Thr Glu Pro Thr Gly Pro Ala Asp
        4515                4520                4525
Ser Val Ser Leu Ser Leu His Asn Ser Arg Gly Thr Ser Ser Ser Asp
    4530                4535                4540
```

```
Val Ser Ala Asn Cys Gly Phe Asp Asp Ser Glu Val Ala Met Ser Asp
4545                4550                4555                4560

Tyr Glu Ser Val Gly Glu Leu Ser Leu Ala Ser Leu His Ile Pro Phe
                4565                4570                4575

Val Glu Thr Gln His Gln Thr Gln Val
                4580                4585

<210> SEQ ID NO 7
<211> LENGTH: 13767
<212> TYPE: DNA
<213> ORGANISM: homo sapiens

<400> SEQUENCE: 7
```

| | | | | |
|---|---|---|---|---|
| atggatataa | ttatgggaca | ctgtgtgggc | acacggcctc | ctgcttgttg cctcatcctc | 60 |
| ctgcttttca | agcttttggc | cactgtctcc | caggggctgc | agggactgg accctgggc | 120 |
| ttccacttca | cacattccat | ttataatgct | accgtgtatg | agaactcagc agcaaggacc | 180 |
| tacgtcaaca | gccagagtag | aatgggcatc | accttaatag | atctatcctg ggatatcaaa | 240 |
| tacagaatag | tgtccggaga | cgaggaaggc | ttttttcaaag | cagaggaagt catcattgca | 300 |
| gatttctgtt | ttctcagaat | aagaactaaa | ggtggcaatt | ctgccatatt aaatagggaa | 360 |
| atccaggata | attatttatt | gatagtaaaa | ggttctgtca | gaggagagga tttggaagca | 420 |
| tggaccaaag | tgaatataca | ggttttagat | atgaatgatc | tgagaccttt gttttcaccc | 480 |
| acaacatact | ctgttaccat | agcagaaagc | acacctctaa | ggactagtgt tgcccaggtg | 540 |
| actgcaacag | acgcagatat | tggttccaat | ggagaattct | actactactt taaaaataaa | 600 |
| gttgatctct | tttcagttca | ccccacgagt | ggtgtcatct | ccttaagtgg tcgattaaat | 660 |
| tatgatgaaa | agaataggta | tgatctggaa | attttggctg | tggaccgggg aatgaaactg | 720 |
| tatgggaaca | atggagtgag | cagtactgca | aagctttatg | ttcacattga gcgcataaat | 780 |
| gaacatgccc | caacaatcca | tgtagtcact | catgttcctt | tctcgttgga aaaagagcca | 840 |
| acatatgcag | tggtgacagt | tgatgactta | gatgatggag | cgaatggaga gatcgaatct | 900 |
| gtttccattg | tggctgggga | tcctttagat | cagttcttcc | tggctaagga aggaaagtgg | 960 |
| ttgaatgagt | acaagattaa | ggagaggaag | cagattgact | gggagagctt tcccatggc | 1020 |
| tacaatctca | ctcttcaagc | aaaagacaag | ggatctcctc | aaaaatgttc agcattaaag | 1080 |
| gcagtctaca | ttggcaaccc | cacaagagac | actgtcccca | ttagatttga aaagaagtg | 1140 |
| tacgatgtga | gcataagtga | atttcccct | cctggtgtcg | tggttgctat agtaaaatta | 1200 |
| agtcctgaac | cgatagatgt | ggaatacaaa | ttatctcctg | gtgaggatgc agtgtacttt | 1260 |
| aaaattaatc | ctcggtcggg | tctgattgtt | acagcacggc | cactgaatac tgttaagaag | 1320 |
| gaggtttata | aactggaggt | gacaaacaag | gaaggagatt | taaaagcaca ggtcaccatc | 1380 |
| agcatagaag | atgcaaatga | ccacacccca | gaatttcagc | aaccactgta tgatgcttat | 1440 |
| gtgaatgaaa | gtgtcccagt | gggaaccagc | gttctaacag | tttcagcttc tgataaggat | 1500 |
| aaaggagaaa | atgggtacat | cacctatagt | atcgctagcc | tgaatttgtt accatttgtc | 1560 |
| attaatcagt | ttacaggtgt | tattagcaca | actgaagaac | tggattttga atcctcccca | 1620 |
| gaaatttaca | gattcattgt | tagagcctct | gactgggggtt | caccataccg ccatgaaagt | 1680 |
| gaggtcaatg | tgactattcg | aataggaaat | gtcaacgaca | acagccctct ctttgaaaaa | 1740 |
| gtggcttgcc | aggagttat | ttcatatgac | tttccagttg | gtgtcacat cacagcagtc | 1800 |
| tcagcgatcg | atatcgatga | acttgaactt | gtaaagtaca | aaatcatttc tggaaatgaa | 1860 |

-continued

```
cttggcttct tttatttaaa cccagattct ggtgttttac agcttaaaaa atcactgaca    1920
aattctggca ttaaaaatgg caattttgcc ctcagaatta cagcaactga tggagagaat    1980
cttgcagacc ccatgtctat taacatttca gtcctacatg ggaaagtgtc ttcaaagagc    2040
ttcagttgca gagaaactcg tgtggctcaa aagctggcag agaaactact cattaaggca    2100
aaagcaaatg ggaaactgaa tctggaagat ggatttcttg acttttattc aattaataga    2160
cagggaccat attttgacaa gtcttttcct tctgatgtgg ctgtaaagga ggatctgcca    2220
gttggtgcta acattctgaa gattaaagcc tatgatgccg actctggctt caatggaaaa    2280 gtgctatttta caatatcaga tggaaatacg gatagttgct ttaatattga tatggagact    2340
gggcagctta aagtccttat gcccatggat cgagaacaca cagacctcta tctccttaat    2400
atcaccatct atgacttagg taatccacag aaatcgtcat ggagactgct gaccatcaat    2460
gtggaggatg ctaatgacaa tagcccagtt tttattcaag acagttactc agttaacatt    2520
cttgaaagtt caggcattgg tactgaaatc attcaagtgg aagccagaga caaagactta    2580
ggttctaatg gtgaagtgac ttactcagtc ttgacagata cacagcagtt tgccatcaat    2640
agctcaactg gaatcgttta tgtagccgac cagttggacc gggaatccaa agccaattat    2700
tctttgaaaa tagaagccag ggacaaggca gagagtggtc agcagctgtt ttcagttgtc    2760
actcttaaag ttttttttaga tgatgtcaat gactgctccc cagctttcat tcccagtagc    2820
tatagtgtga aggttcttga agatctccct gttggcactg tcattgcttg gcttgagacc    2880
catgatccag atcttggact gggggtcaa gtgcgctatt ctttggtcaa tgactataat    2940
gggagatttg aaatagataa agcaagtggt gccatccgct tgagcaaaga gcttgattat    3000
gagaaacagc agttctataa ccttactgtg cgggccaaag acaaagggcg gcctgtctct    3060
ctgtcatctg tttcctttgt tgaggtggaa gtggtggatg tcaatgaaaa cctccacact    3120
ccctatttcc cagactttgc tgttgttgga tctgtaaagg aaaactcacg cattggaaca    3180
agcgtgctgc aggtgactgc tcgagatgaa gactccggaa gggatggaga gatccagtac    3240
tccatcaggg atggcagtgg tcttggaagg ttcagtatag cgacgagag tggggtcatc    3300 actgccgcag acattcttga tcgggagaca atgggggtcat actggctaac agtgtatgcc    3360
acagacaggg gcgttgttcc actctactcc accattgagg tctacattga agttgaagat    3420
gtgaatgaca atgccccgct gacctcagaa cctatatatt atcctgttgt catggaaaac    3480
tctccaaagg acgtatctgt cattcagatc caggctgaag atcctgactc cagttccaat    3540
gaaaaactga catacaggat tacaagtgga atcctcaga atttttttgc catcaatatc    3600
aaaacaggtc tgattacaac aacttcaagg aaattggatc gagaacagca ggcagaacat    3660
tttctggagg tgactgtgac agatggtggt ccctctccaa aacagtcaac catttgggtg    3720
gtggttcagg ttctagatga aaatgacaac aagcccagt tcccagagaa ggtctaccag    3780
atcaagctgc cagaacgtga ccgaaagaag agaggagaac cgatttacag ggcttttgca    3840
tttgatagag atgagggccc caacgcagaa atctcctaca gtattgtgga tgggaatgat    3900
gacggaaagt tctttattga ccctaaaact gggatggttt cttctagaaa gcagtttaca    3960
gcaggcagtt atgacatcct aacgataaag gcagtggaca atgggcgccc acagaaatcc    4020
tccacggccc gcctccacat tgaatggatt aagaaaccac cccttcacc tataccattg    4080 accttcgatg agccgtttta aacttcaca gtcatggaaa gtgatagagt gactgaaatt    4140
gtaggggtgg tgtctgtgca gccagctaac accccctctgt ggtttgacat agttgggggg    4200
```

-continued

| | |
|---|---|
| aattttgaca gcgcttttga tgcagagaag ggtgttggga caattgtcat cgcaaaacct | 4260 |
| ttggatgcag agcagaggtc catctataat atgagtgtgg aagtcaccga tgggacaaat | 4320 |
| gttgctgtta ctcaggtatt tatcaaagtg ctggataata atgataatgg cccagaattc | 4380 |
| tctcagccga attacgatgt gacaatttcc gaggatgtgc ttccagacac ggagatcctg | 4440 |
| cagattgaag ccacagatag agatgagaag cacaagctga gctacactgt tcatagcagc | 4500 |
| atcgactcca tcagcatgag aaaattccgg attgaccctca gcactggcgt gctctatact | 4560 |
| gccgagaggc tggaccatga ggcccaggac aagcacattc tcaacataat ggtcagagat | 4620 |
| caggagtttc cttatcgaag aaacttggcc cgagtcattg tgaatgtgga ggatgctaat | 4680 |
| gatcacagtc cttatttac caacccactg tatgaagcgt ctgtgtttga atctgctgct | 4740 |
| ctgggatcag ctgttctgca agtgacggct ctggacaaag acaaggaga aaatgcagaa | 4800 |
| ctcatatata ccatagaagc agggaacact gggaacatgt ttaagatcga accggtccta | 4860 |
| ggcatcatca ccatttgcaa agaaccagac atgacgacga tgggtcagtt tgtcctatcc | 4920 |
| atcaaagtca cagatcaggg atccccgcca atgtctgcta ctgcaattgt gcgcatttcc | 4980 |
| gtcaccatgt ctgacaattc tcaccccaag ttcattcaca aagactacca agcagaagta | 5040 |
| aatgaaaatg ttgacattgg aacatcagtc attctaatct ctgccatcag tcaatctacc | 5100 |
| ctcatttatg aagtcaaaga tggagacatt aatgggatct ttaccataaa tccatattct | 5160 |
| ggagtcatca ccactcagaa ggccctggat tatgagcgca catcctctta tcaactcatc | 5220 |
| attcaggcca ccaatatggc aggaatggct tccaatgcta cagtcaatat tcagattgtt | 5280 |
| gatgaaaatg ataatgcccc agttttctc ttttctcaat actcaggcag cctaagtgag | 5340 |
| gctgccccaa ttaatagcat tgtcaggagc ttggataaca gcccactggt gattcgagcc | 5400 |
| acagatgctg acagcaaccg gaatgctctg cttgtgtatc agattgtgga gtcaacagca | 5460 |
| aaaaagtttt tcacggtgga ctccagtaca ggtgcaatca aacaattgc caacctggac | 5520 |
| catgaaacca ttgcccattt ccattttcat gtgcatgtga gagacagtgg tagcccccaa | 5580 |
| ctgactgcag agagtcccgt tgaagtcaac attgaggtga cagatgtgaa tgataaccca | 5640 |
| cctgttttta ctcaggctgt gtttgagact atcttacttc tacctaccta tgttggagtg | 5700 |
| gaggttctga agttagtgc cacagatcct gactctgagg taccccctga actgacatac | 5760 |
| agcctaatgg aaggcagttt ggatcatttt ttaattgact caaacagtgg agtacttacc | 5820 |
| ataaaaaaca caaccctctc caaggatcac tacatgctga tagttaaggt gtctgatgga | 5880 |
| aagttctaca gtacctccat ggtcaccatc atggttaaag aagccatgga cagcggcctc | 5940 |
| cactttacac aaagcttcta ttccaccctca atctcagaga acaacactaa cataaccaaa | 6000 |
| gttgctattg tcaatgcagt tggaaatcgc cttaatgagc ccttaaaata cagcatctta | 6060 |
| aacccaggaa ataagttcaa gataaaatct acctcagggg tcattcagac gactggagtc | 6120 |
| cccttttgacc gtgaagaaca agagttatat gagctggtgg tagaagccag ccgtgagctg | 6180 |
| gaccatctgc gtgtggccag agtggtggtc agggttaaca ttgaagacat aaatgacaat | 6240 |
| tctccagtct ttgtgggcct cccatactat gctgctgttc aagtggatgc ggaacccggg | 6300 |
| actctgattt atcaggtgac agccattgac aaagataaag gtccaaatgg agaagtgacc | 6360 |
| tatgtcctgc aggatgacta tggccacttt gaaattaacc ctaattcagg gaatgttatt | 6420 |
| ttaaaggaag cattcaactc tgacttgtcc aacattgagt atggagtcac catcctagcc | 6480 |
| aaggatggcg gaaaaccttc tttgtctaca tctgtggagc ttcccatcac tatttgtcaac | 6540 |
| aaagcaatgc ctgtgtttga taagcccttt tatacagcat ctgtcaatga agacatcaga | 6600 |

```
atgaacacac ccatcctaag catcaatgcc accagtccag aaggccaagg catcatatat   6660
atcattatcg atggggaccc tttaaacag tttaacattg actttgacac tggggtcctg    6720
aaagttgtta gcccttttgga ttatgaagtt acatctgctt acaagctgac aataagagcc  6780
agcgacgccc ttactggtgc tagggctgaa gtcactgttg acttgctagt taatgatgta  6840
aatgacaacc cccctatttt cgatcagcct acatacaata caacactatc agaagcatct  6900
cttattggga cacctgtttt acaagttgtc tctattgatg cagactcaga aaacaataaa  6960
atggtacatt atcagattgt ccaggatacc tacaatagca cagattattt tcacatagat  7020
agctcaagtg gcttaatcct gacagcacga atgctggacc atgagttagt acaacactgc  7080
actttgaaag tcagatcaat agatagtggc ttcccatcac tgagcagtga ggttctcgtt  7140
catatctaca tctctgatgt aaatgacaac cctccagttt ttaatcagct catttatgag  7200
tcatatgtga gtgaattagc cccccggggc cattttgtaa cctgtgtaca agcctctgat  7260
gcagacagct ctgattttga ccggttggaa tatagcattt tatctgggaa tgaccggacg  7320
agctttctga tggacagcaa gagtggagtt atcacattgt ccaaccatcg gaagcagcgg  7380
atggagcctc tgtacagtct caatgtgtct gtctctgatg ggttgttcac cagcactgca  7440
caggtgcata ttagggtact tgggctaac ttgtacagcc ctgccttttc acaaagcaca  7500
tacgtagctg aggtgagaga gaacgtggct gcaggaacaa aggtaattca tgttcgagcc  7560
acagatggtg atccagggac ttatgggcag atcagctatg ccatcatcaa tgactttgcc  7620
aaggatcgat tcctcataga cagcaatggg caggtcatca ccacagaaag gctagaccgg  7680
gaaaaccctc tagaagggga tgttagtatt tttgtgaggg cccttgatgg tggagggaga  7740
acaactttct gcactgtgag agtgattgtt gtggatgaaa atgacaatgc tcccagttc   7800 atgacagtgg aatatagagc cagtgtcagg gcagatgttg aaggggcca cttggtcact   7860 caagttcaag ccatagatcc cgatgatgga gcaaattcaa ggattactta ttccctctat  7920
agcgaggcct ctgtttcagt ggccgacctc ctggaaatcg atcctgacaa tggctggatg  7980
gtcacaaagg gtaattttaa ccagctgaaa aatacagtgc tttcgttctt tgtcaaagca  8040
gtagatgggg gcatcccagt aaagcactcc ctcattcctg tctatatcca cgtcttgccc  8100
cctgaaacgt tcttgccatc attcacccag tctcagtatt cctttaccat tgcagaagat  8160
acagccattg ggagtacagt ggacaccctg aggattttgc ccagtcagaa tgtctggttc  8220
agcacagtta atgggaacg gccagaaaat aacaaagggg gcgtattcgt catagaacag  8280
gaaacaggca ctattaagct tgacaaacgc cttgaccgtg aaaccagccc agctttccac  8340
tttaaagtag cagccactat acccctggac aaagtagaca ttgtgtttac tgtggatgta  8400
gatatcaagg tattggattt gaatgacaac aagccagtct ttgaaacttc aagctatgac  8460
accattataa tggaagggat gcctgttggc accaaactca cacaagtgag agctattgat  8520
atggactggg gagccaatgg acaagtcact tactccctcc actcggattc ccagcccgaa  8580
aaggtaatgg aagcattcaa tattgacagc aacacgggct ggatcagtac cttgaaggac  8640
ctagatcacg agacagaccc cacattcacc ttctctgtgg tggcctctga ccttggagag  8700
gcattctctc tttcctccac ggccttggtc tctgtcagag tgacagatat aaatgacaat  8760
gcaccagtct tcgcgcagga agtgtaccga gggaatgtga aggagagcga cccaccgggc  8820
gaggtggtag ccgtcctcag cacctgggac agagacacat ccgacgttaa tcgccaagtg  8880
agctaccata ttacaggagg aaaccctcga ggaaggtttg ctctgggcct ggtgcaaagt  8940
```

```
gagtggaagg tctatgtgaa gaggcctcta gacagagaag aacaggacat ttactttctc   9000
aatatcactg ccactgatgg gcttttgtc acacaggcca tggtggaagt gagcgtcagt   9060
gatgtgaatg acaatagccc agtgtgtgat caggttgcat atacagcatt acttcctgaa   9120
gacattccat caaataaaat catcctgaaa gtcagtgcaa aggatgctga tattggatcc   9180
aatggatata tacgatactc actctatgga tctggaaaca gtgaattttt tctagatcca   9240
gaaagtggcg agttaaaaac cttggctctg ttggaccggg agaggatccc cgtgtacagc   9300
ctgatggcca aggccactga cggggtggc aggttctgcc agtccaacat ccacctaatc   9360
ctggaggatg tgaatgataa ccccctgtg ttttcttctg accactacaa cacctgtgtc   9420
tatgagaaca cagccaccaa ggctctgttg accagagttc aagccgtgga ccccgacatt   9480
ggcatcaata ggaaggtcgt gtactccctg gcagactcag ctggtgggt cttctccatt   9540 gacagctcat ctggcatcat catcctggag cagccactgg accgtgagca gcagtcttcg   9600
tacaacatca gcgtgcgggc cactgaccag agtcctggac agtccctgtc ctctctcact   9660
actgtcacca tcaccgttct ggacattaat gacaaccccc ctgtgtttga gaggagggac   9720
tacctggtga cggtgcctga ggacacctcc cctggcaccc aagtccttgc tgtttttgcc   9780
accagcaaag atattggcac aaatgctgag atcacttatc tcatccggtc tgggaacgaa   9840
caagggaaat ttaagatcaa ccccaagaca ggggtattt ctgtctctga agtcctggac   9900
tatgaattat gcaaaaggtt ttacctggta gtggaagcca agatgggggg caccccagct  9960
ctcagcgctg tggccactgt caacatcaac ctcacagatg ttaatgacaa ccctcccaag  10020
ttcagccaag acgtctacag tgcggttatc agtgaagacg ccttggtggg agactctgtc  10080
attttgctaa tagcagaaga tgtagacagc cagcccaacg gacagattca tttttccatt  10140
gtgaatggag atcgggacaa tgaatttact gtagatcctg tcttgggact tgtgaaagtt  10200
aagaagaaat tggaccggga acgggtgtct ggatactctc tgcttgtcca ggccgtagac  10260
agtggcattc ctgcaatgtc atcaactgca actgtcaaca ttgatatttc tgatgtgaat  10320
gacaacagcc cggtgtttac acctgccaac tatactgctg tgattcagga aaataagcca  10380
gtgggcacca gcatcttgca gctggtggtg acagacagag actccttca caatgggcct  10440 ccctttcat tctctattt gtcgggaaat aagaggagg agtttgtgtt ggaccctcat  10500
gggatcttgc ggtcggctgt ggtcttccag cacacagagt ctctggaata cgtgttgtgt  10560
gtccaggcaa aggattcagg caaaccccag caagtttctc acacttacat ccgcgtgcga  10620
gtcattgagg aaagcaccca caagcccaca gccattcccc tggaaatttt cattgtcacc  10680
atggaggatg actttcctgg tggggtcatt gggaagattc atgccacaga tcaagacatg  10740
tatgatgtgc tcacatttgc cctgaaatcg gagcagaaaa gcttatttaa agtgaacagt  10800
cacgatggga aaatcatcgc cctgggaggc ctggacagcg gcaagtatgt cctgaatgtg  10860
tctgtgagtg atggtcgctt ccaggtaccc attgatgtgg tcgtgcatgt ggagcagttg  10920
gtgcatgaga tgctgcagaa cactgtcacc atccgctttg aaaatgtgtc ccctgaggac  10980 ttcgtgggc tgcacatgca tgggttccgg cgcacccctgc ggaatgcagt cctcacccag  11040
aagcaggaca gcctgcgcat catcagcatc cagcccgtgg caggcaccaa ccaactggac  11100
atgctgtttg cggtggagat gcacagcagc gagttctaca agccagccta cctgatccag  11160
aagctgtcca atgctagaag acacctggag aatatcatgc gcatctcagc catcttggag  11220
aagaactgct cagggctgga ctgtcaggaa cagcattgtg agcaaggctt gtcactcgat  11280
tcccacgcgc tcatgaccta cagcacggct cgcatcagct ttgtgtgtcc gcgtttctac  11340
```

```
aggaacgtgc gttgcacctg caatggagga ctgtgtccgg ggtccaacga tccttgtgtg   11400
gagaagccgt gtccagggga catgcagtgt gtcggttatg aagccagcag gagaccgttc   11460
ctctgccagt gtccaccagg gaagctcgga gagtgctcag ggcacacttc tctcagcttt   11520
gctggaaaca gttacatcaa atatcggctt tctgaaaata gcaaagaaga ggatttcaaa   11580
ctagctctgc gtcttcgaac actgcaaagc aatgggatta taatgtacac cagagcaaat   11640
ccctgcataa ttctgaagat tgtggatggc aagctgtggt tccagctgga ctgcggcagc   11700
ggccctggaa tcttgggcat ctcgggccgt gctgtcaacg acgggagctg gcactcggtc   11760
ttcctggagc tcaaccgcaa tttcacgagc ctgtccctgg atgacagcta cgtggagcgg   11820
cgccgggcgc ccctctactt ccagacgctg agcactgaga gtagcatcta cttcggcgcc   11880
ctggtgcaag cggataacat ccgcagcctg actgacacgc gggtcacgca ggtgctcagc   11940
ggcttccagg gctgcctgga ctcggtgata ctgaataaca atgagctgcc gctgcagaac   12000
aagcgcagca gcttcgcgga ggtggtgggc ctgacggagc tgaagctggg ctgcgtgctc   12060
tatcccgacg cctgcaagcg cagcccgtgc cagcacgggg gcagctgcac tggcctgcca   12120 tcgggggggct atcagtgtac ctgtctctca cagtttacgg ggagaaactg tgaatctgag   12180
attacagcct gcttcccaaa cccctgccgg aatggaggat cctgcgatcc aataggaaac   12240
actttcatct gcaattgtaa agctgggctc actgagtcac gtgtgagga ggacatcaat   12300 gagtgcgaac gagaggagtg tgagaacgga ggctcctgcg tgaacgtgtt cggctccttc   12360
ctctgcaact gcacgccggg ctacgtgggc cagtactgcg ggcgcccgt ggtggtaccc   12420 aatatccagg ctggccactc ctacgtgggg aaggaggagc tcatcggcat cgccgtggtc   12480
ctcttcgtca tcttcatcct ggtggttctc ttcatagtct tccgcaagaa ggtcttccgc   12540
aagaactact cccgcaacaa catcacgcta gtgcaggacc cggccaccgc cgccctgctt   12600
aacaagagca atggcatccc cgttccggaac ctgcgcggca gtggggacgg ccgcaacgtc   12660
taccaggagg tggggcccccc gcaggtcccc gtgcgcccca tggcctacac accctgcttc   12720
cagagtgact ccaggagcaa cctggataag atcgtggacg ggctgggagg cgagcaccag   12780
gaaatgacca cgtttcaccc tgagtcgccc cgcatcctga cagcccggcg gggcgtggtc   12840
gtgtgcagtg tggccccccaa cctccccgcc gtgtcaccct gccgctccga ctgcgactcc   12900
atccggaaga atggctggga cgcgggaact gagaacaaag gggttgatga cccgggagaa   12960
gtgacctgct ttgcaggtag taataaaggc agcaactctg aagttcagtc cctcagctcc   13020
ttccagtcag attctggtga cgacaatgcc tccatagtga ctgtcattca gcttgtcaac   13080
aatgtagttg acactataga gaatgaagtg tctgtcatgg accaaggaca gaactacaac   13140
cgagcctatc actgggacac ctctgattgg atgccagggg cccgcctgtc ggacatagag   13200
gaagtgccca actatgagaa ccaggatgga gggtctgcac accaggggag cacacgggag   13260
ctggagagcg attactacct gggtggttat gacattgaca gtgaataccc acccccctcat   13320 gaagaggagt tcttgagtca ggaccagctg cctcctcctc tccgggagga cttcccagac   13380
caatatgagg ccctgccacc ctcccagcct gtctccctgg ccagcacact gagcccagac   13440
tgcaggagaa ggccccagtt tcatcctagc cagtatctcc ctcctcaccc attccccaac   13500
gaaacggatt tggtgggccc gcctgccagc tgtgaattta gtacttttgc tgtgagcatg   13560
aaccagggca cagagcccac aggcccagca gacagcgtgt ctctgtcctt gcacaattcc   13620
agaggcacct catcctcgga tgtgtctgcc aactgcgggct tgacgattc cgaagtagcc   13680
```

-continued

```
atgagtgact acgagagcgt gggagagctc agcctcgcca gccttcacat tcccttgtg    13740 gagactcagc atcagactca agtgtag                                        13767
```

<210> SEQ ID NO 8
<211> LENGTH: 4588
<212> TYPE: PRT
<213> ORGANISM: homo sapiens

<400> SEQUENCE: 8

```
Met Asp Ile Ile Met Gly His Cys Val Gly Thr Arg Pro Ala Cys
 1               5                  10                  15

Cys Leu Ile Leu Leu Phe Lys Leu Leu Ala Thr Val Ser Gln Gly
                20                  25                  30

Leu Pro Gly Thr Gly Pro Leu Gly Phe His Phe Thr His Ser Ile Tyr
                35                  40                  45

Asn Ala Thr Val Tyr Glu Asn Ser Ala Ala Arg Thr Tyr Val Asn Ser
 50                      55                  60

Gln Ser Arg Met Gly Ile Thr Leu Ile Asp Leu Ser Trp Asp Ile Lys
65                      70                  75                  80

Tyr Arg Ile Val Ser Gly Asp Glu Glu Gly Phe Phe Lys Ala Glu Glu
                        85                  90                  95

Val Ile Ile Ala Asp Phe Cys Phe Leu Arg Ile Arg Thr Lys Gly Gly
                100                 105                 110

Asn Ser Ala Ile Leu Asn Arg Glu Ile Gln Asp Asn Tyr Leu Leu Ile
                115                 120                 125

Val Lys Gly Ser Val Arg Gly Glu Asp Leu Glu Ala Trp Thr Lys Val
                130                 135                 140

Asn Ile Gln Val Leu Asp Met Asn Asp Leu Arg Pro Leu Phe Ser Pro
145                 150                 155                 160

Thr Thr Tyr Ser Val Thr Ile Ala Glu Ser Thr Pro Leu Arg Thr Ser
                165                 170                 175

Val Ala Gln Val Thr Ala Thr Asp Ala Asp Ile Gly Ser Asn Gly Glu
                180                 185                 190

Phe Tyr Tyr Tyr Phe Lys Asn Lys Val Asp Leu Phe Ser Val His Pro
                195                 200                 205

Thr Ser Gly Val Ile Ser Leu Ser Gly Arg Leu Asn Tyr Asp Glu Lys
                210                 215                 220

Asn Arg Tyr Asp Leu Glu Ile Leu Ala Val Asp Arg Gly Met Lys Leu
225                 230                 235                 240

Tyr Gly Asn Asn Gly Val Ser Ser Thr Ala Lys Leu Tyr Val His Ile
                245                 250                 255

Glu Arg Ile Asn Glu His Ala Pro Thr Ile His Val Thr His Val
                260                 265                 270

Pro Phe Ser Leu Glu Lys Glu Pro Thr Tyr Ala Val Val Thr Val Asp
                275                 280                 285

Asp Leu Asp Asp Gly Ala Asn Gly Glu Ile Glu Ser Val Ser Ile Val
                290                 295                 300

Ala Gly Asp Pro Leu Asp Gln Phe Phe Leu Lys Glu Gly Lys Trp
305                 310                 315                 320

Leu Asn Glu Tyr Lys Ile Lys Glu Arg Lys Gln Ile Asp Trp Glu Ser
                325                 330                 335

Phe Pro Tyr Gly Tyr Asn Leu Thr Leu Gln Ala Lys Asp Lys Gly Ser
                340                 345                 350

Pro Gln Lys Cys Ser Ala Leu Lys Ala Val Tyr Ile Gly Asn Pro Thr
```

-continued

```
                355                 360                 365
Arg Asp Thr Val Pro Ile Arg Phe Glu Lys Glu Val Tyr Asp Val Ser
        370                 375                 380
Ile Ser Glu Phe Ser Pro Pro Gly Val Val Ala Ile Val Lys Leu
385                 390                 395                 400
Ser Pro Glu Pro Ile Asp Val Glu Tyr Lys Leu Ser Pro Gly Glu Asp
                405                 410                 415
Ala Val Tyr Phe Lys Ile Asn Pro Arg Ser Gly Leu Ile Val Thr Ala
                420                 425                 430
Arg Pro Leu Asn Thr Val Lys Lys Glu Val Tyr Lys Leu Glu Val Thr
        435                 440                 445
Asn Lys Glu Gly Asp Leu Lys Ala Gln Val Thr Ile Ser Ile Glu Asp
        450                 455                 460
Ala Asn Asp His Thr Pro Glu Phe Gln Gln Pro Leu Tyr Asp Ala Tyr
465                 470                 475                 480
Val Asn Glu Ser Val Pro Val Gly Thr Ser Val Leu Thr Val Ser Ala
                485                 490                 495
Ser Asp Lys Asp Lys Gly Glu Asn Gly Tyr Ile Thr Tyr Ser Ile Ala
                500                 505                 510
Ser Leu Asn Leu Leu Pro Phe Val Ile Asn Gln Phe Thr Gly Val Ile
                515                 520                 525
Ser Thr Thr Glu Glu Leu Asp Phe Glu Ser Ser Pro Glu Ile Tyr Arg
        530                 535                 540
Phe Ile Val Arg Ala Ser Asp Trp Gly Ser Pro Tyr Arg His Glu Ser
545                 550                 555                 560
Glu Val Asn Val Thr Ile Arg Ile Gly Asn Val Asn Asp Asn Ser Pro
                565                 570                 575
Leu Phe Glu Lys Val Ala Cys Gln Gly Val Ile Ser Tyr Asp Phe Pro
                580                 585                 590
Val Gly Gly His Ile Thr Ala Val Ser Ala Ile Asp Ile Asp Glu Leu
                595                 600                 605
Glu Leu Val Lys Tyr Lys Ile Ile Ser Gly Asn Glu Leu Gly Phe Phe
        610                 615                 620
Tyr Leu Asn Pro Asp Ser Gly Val Leu Gln Leu Lys Lys Ser Leu Thr
625                 630                 635                 640
Asn Ser Gly Ile Lys Asn Gly Asn Phe Ala Leu Arg Ile Thr Ala Thr
                645                 650                 655
Asp Gly Glu Asn Leu Ala Asp Pro Met Ser Ile Asn Ile Ser Val Leu
                660                 665                 670
His Gly Lys Val Ser Ser Lys Ser Phe Ser Cys Arg Glu Thr Arg Val
                675                 680                 685
Ala Gln Lys Leu Ala Glu Lys Leu Leu Ile Lys Ala Lys Ala Asn Gly
        690                 695                 700
Lys Leu Asn Leu Glu Asp Gly Phe Leu Asp Phe Tyr Ser Ile Asn Arg
705                 710                 715                 720
Gln Gly Pro Tyr Phe Asp Lys Ser Phe Pro Ser Asp Val Ala Val Lys
                725                 730                 735
Glu Asp Leu Pro Val Gly Ala Asn Ile Leu Ile Lys Ala Tyr Asp
                740                 745                 750
Ala Asp Ser Gly Phe Asn Gly Lys Val Leu Phe Thr Ile Ser Asp Gly
            755                 760                 765
Asn Thr Asp Ser Cys Phe Asn Ile Asp Met Glu Thr Gly Gln Leu Lys
        770                 775                 780
```

```
Val Leu Met Pro Met Asp Arg Glu His Thr Asp Leu Tyr Leu Leu Asn
785                 790                 795                 800

Ile Thr Ile Tyr Asp Leu Gly Asn Pro Gln Lys Ser Ser Trp Arg Leu
                805                 810                 815

Leu Thr Ile Asn Val Glu Asp Ala Asn Asp Asn Ser Pro Val Phe Ile
                820                 825                 830

Gln Asp Ser Tyr Ser Val Asn Ile Leu Glu Ser Ser Gly Ile Gly Thr
            835                 840                 845

Glu Ile Ile Gln Val Glu Ala Arg Asp Lys Asp Leu Gly Ser Asn Gly
850                 855                 860

Glu Val Thr Tyr Ser Val Leu Thr Asp Thr Gln Gln Phe Ala Ile Asn
865                 870                 875                 880

Ser Ser Thr Gly Ile Val Tyr Val Ala Asp Gln Leu Asp Arg Glu Ser
                885                 890                 895

Lys Ala Asn Tyr Ser Leu Lys Ile Glu Ala Arg Asp Lys Ala Glu Ser
                900                 905                 910

Gly Gln Gln Leu Phe Ser Val Val Thr Leu Lys Val Phe Leu Asp Asp
            915                 920                 925

Val Asn Asp Cys Ser Pro Ala Phe Ile Pro Ser Ser Tyr Ser Val Lys
930                 935                 940

Val Leu Glu Asp Leu Pro Val Gly Thr Val Ile Ala Trp Leu Glu Thr
945                 950                 955                 960

His Asp Pro Asp Leu Gly Leu Gly Gly Gln Val Arg Tyr Ser Leu Val
                965                 970                 975

Asn Asp Tyr Asn Gly Arg Phe Glu Ile Asp Lys Ala Ser Gly Ala Ile
                980                 985                 990

Arg Leu Ser Lys Glu Leu Asp Tyr Glu Lys Gln Gln Phe Tyr Asn Leu
            995                 1000                1005

Thr Val Arg Ala Lys Asp Lys Gly Arg Pro Val Ser Leu Ser Ser Val
    1010                1015                1020

Ser Phe Val Glu Val Glu Val Val Asp Val Asn Glu Asn Leu His Thr
1025                1030                1035                1040

Pro Tyr Phe Pro Asp Phe Ala Val Val Gly Ser Val Lys Glu Asn Ser
                1045                1050                1055

Arg Ile Gly Thr Ser Val Leu Gln Val Thr Ala Arg Asp Glu Asp Ser
            1060                1065                1070

Gly Arg Asp Gly Glu Ile Gln Tyr Ser Ile Arg Asp Gly Ser Gly Leu
    1075                1080                1085

Gly Arg Phe Ser Ile Asp Asp Glu Ser Gly Val Ile Thr Ala Ala Asp
    1090                1095                1100

Ile Leu Asp Arg Glu Thr Met Gly Ser Tyr Trp Leu Thr Val Tyr Ala
1105                1110                1115                1120

Thr Asp Arg Gly Val Val Pro Leu Tyr Ser Thr Ile Glu Val Tyr Ile
            1125                1130                1135

Glu Val Glu Asp Val Asn Asp Asn Ala Pro Leu Thr Ser Glu Pro Ile
        1140                1145                1150

Tyr Tyr Pro Val Val Met Glu Asn Ser Pro Lys Asp Val Ser Val Ile
        1155                1160                1165

Gln Ile Gln Ala Glu Asp Pro Asp Ser Ser Asn Glu Lys Leu Thr
        1170                1175                1180

Tyr Arg Ile Thr Ser Gly Asn Pro Gln Asn Phe Phe Ala Ile Asn Ile
1185                1190                1195                1200
```

-continued

```
Lys Thr Gly Leu Ile Thr Thr Thr Ser Arg Lys Leu Asp Arg Glu Gln
            1205                1210                1215
Gln Ala Glu His Phe Leu Glu Val Thr Val Thr Asp Gly Gly Pro Ser
        1220                1225                1230
Pro Lys Gln Ser Thr Ile Trp Val Val Gln Val Leu Asp Glu Asn
        1235                1240                1245
Asp Asn Lys Pro Gln Phe Pro Glu Lys Val Tyr Gln Ile Lys Leu Pro
        1250                1255                1260
Glu Arg Asp Arg Lys Lys Arg Gly Glu Pro Ile Tyr Arg Ala Phe Ala
1265            1270                1275                1280
Phe Asp Arg Asp Glu Gly Pro Asn Ala Glu Ile Ser Tyr Ser Ile Val
                1285                1290                1295
Asp Gly Asn Asp Asp Gly Lys Phe Phe Ile Asp Pro Lys Thr Gly Met
                1300                1305                1310
Val Ser Ser Arg Lys Gln Phe Thr Ala Gly Ser Tyr Asp Ile Leu Thr
                1315                1320                1325
Ile Lys Ala Val Asp Asn Gly Arg Pro Gln Lys Ser Ser Thr Ala Arg
                1330                1335                1340
Leu His Ile Glu Trp Ile Lys Lys Pro Pro Ser Pro Ile Pro Leu
1345                1350                1355                1360
Thr Phe Asp Glu Pro Phe Tyr Asn Phe Thr Val Met Glu Ser Asp Arg
                1365                1370                1375
Val Thr Glu Ile Val Gly Val Val Ser Val Gln Pro Ala Asn Thr Pro
                1380                1385                1390
Leu Trp Phe Asp Ile Val Gly Gly Asn Phe Asp Ser Ala Phe Asp Ala
                1395                1400                1405
Glu Lys Gly Val Gly Thr Ile Val Ile Ala Lys Pro Leu Asp Ala Glu
            1410                1415                1420
Gln Arg Ser Ile Tyr Asn Met Ser Val Glu Val Thr Asp Gly Thr Asn
1425                1430                1435                1440
Val Ala Val Thr Gln Val Phe Ile Lys Val Leu Asp Asn Asn Asp Asn
                1445                1450                1455
Gly Pro Glu Phe Ser Gln Pro Asn Tyr Asp Val Thr Ile Ser Glu Asp
            1460                1465                1470
Val Leu Pro Asp Thr Glu Ile Leu Gln Ile Glu Ala Thr Asp Arg Asp
        1475                1480                1485
Glu Lys His Lys Leu Ser Tyr Thr Val His Ser Ser Ile Asp Ser Ile
        1490                1495                1500
Ser Met Arg Lys Phe Arg Ile Asp Pro Ser Thr Gly Val Leu Tyr Thr
1505                1510                1515                1520
Ala Glu Arg Leu Asp His Glu Ala Gln Asp Lys His Ile Leu Asn Ile
            1525                1530                1535
Met Val Arg Asp Gln Glu Phe Pro Tyr Arg Arg Asn Leu Ala Arg Val
            1540                1545                1550
Ile Val Asn Val Glu Asp Ala Asn Asp His Ser Pro Tyr Phe Thr Asn
        1555                1560                1565
Pro Leu Tyr Glu Ala Ser Val Phe Glu Ser Ala Ala Leu Gly Ser Ala
        1570                1575                1580
Val Leu Gln Val Thr Ala Leu Asp Lys Asp Lys Gly Glu Asn Ala Glu
1585                1590                1595                1600
Leu Ile Tyr Thr Ile Glu Ala Gly Asn Thr Gly Asn Met Phe Lys Ile
            1605                1610                1615
Glu Pro Val Leu Gly Ile Ile Thr Ile Cys Lys Glu Pro Asp Met Thr
```

-continued

```
                   1620              1625              1630
Thr Met Gly Gln Phe Val Leu Ser Ile Lys Val Thr Asp Gln Gly Ser
            1635              1640              1645

Pro Pro Met Ser Ala Thr Ala Ile Val Arg Ile Ser Val Thr Met Ser
        1650              1655              1660

Asp Asn Ser His Pro Lys Phe Ile His Lys Asp Tyr Gln Ala Glu Val
1665              1670              1675              1680

Asn Glu Asn Val Asp Ile Gly Thr Ser Val Ile Leu Ile Ser Ala Ile
                    1685              1690              1695

Ser Gln Ser Thr Leu Ile Tyr Glu Val Lys Asp Gly Asp Ile Asn Gly
                1700              1705              1710

Ile Phe Thr Ile Asn Pro Tyr Ser Gly Val Ile Thr Thr Gln Lys Ala
            1715              1720              1725

Leu Asp Tyr Glu Arg Thr Ser Ser Tyr Gln Leu Ile Ile Gln Ala Thr
        1730              1735              1740

Asn Met Ala Gly Met Ala Ser Asn Ala Thr Val Asn Ile Gln Ile Val
1745              1750              1755              1760

Asp Glu Asn Asp Asn Ala Pro Val Phe Leu Phe Ser Gln Tyr Ser Gly
                    1765              1770              1775

Ser Leu Ser Glu Ala Ala Pro Ile Asn Ser Ile Val Arg Ser Leu Asp
                1780              1785              1790

Asn Ser Pro Leu Val Ile Arg Ala Thr Asp Ala Asp Ser Asn Arg Asn
            1795              1800              1805

Ala Leu Leu Val Tyr Gln Ile Val Glu Ser Thr Ala Lys Lys Phe Phe
        1810              1815              1820

Thr Val Asp Ser Ser Thr Gly Ala Ile Arg Thr Ile Ala Asn Leu Asp
1825              1830              1835              1840

His Glu Thr Ile Ala His Phe His Phe His Val His Val Arg Asp Ser
                    1845              1850              1855

Gly Ser Pro Gln Leu Thr Ala Glu Ser Pro Val Glu Val Asn Ile Glu
                1860              1865              1870

Val Thr Asp Val Asn Asp Asn Pro Pro Val Phe Thr Gln Ala Val Phe
            1875              1880              1885

Glu Thr Ile Leu Leu Leu Pro Thr Tyr Val Gly Val Glu Val Leu Lys
        1890              1895              1900

Val Ser Ala Thr Asp Pro Asp Ser Glu Val Pro Pro Glu Leu Thr Tyr
1905              1910              1915              1920

Ser Leu Met Glu Gly Ser Leu Asp His Phe Leu Ile Asp Ser Asn Ser
                    1925              1930              1935

Gly Val Leu Thr Ile Lys Asn Asn Asn Leu Ser Lys Asp His Tyr Met
                1940              1945              1950

Leu Ile Val Lys Val Ser Asp Gly Lys Phe Tyr Ser Thr Ser Met Val
            1955              1960              1965

Thr Ile Met Val Lys Glu Ala Met Asp Ser Gly Leu His Phe Thr Gln
        1970              1975              1980

Ser Phe Tyr Ser Thr Ser Ile Ser Glu Asn Asn Thr Asn Ile Thr Lys
1985              1990              1995              2000

Val Ala Ile Val Asn Ala Val Gly Asn Arg Leu Asn Glu Pro Leu Lys
                    2005              2010              2015

Tyr Ser Ile Leu Asn Pro Gly Asn Lys Phe Lys Ile Lys Ser Thr Ser
                2020              2025              2030

Gly Val Ile Gln Thr Thr Gly Val Pro Phe Asp Arg Glu Glu Gln Glu
            2035              2040              2045
```

-continued

```
Leu Tyr Glu Leu Val Val Glu Ala Ser Arg Glu Leu Asp His Leu Arg
    2050                2055                2060
Val Ala Arg Val Val Arg Val Asn Ile Glu Asp Ile Asn Asp Asn
2065            2070                2075                2080
Ser Pro Val Phe Val Gly Leu Pro Tyr Tyr Ala Ala Val Gln Val Asp
                2085                2090                2095
Ala Glu Pro Gly Thr Leu Ile Tyr Gln Val Thr Ala Ile Asp Lys Asp
            2100                2105                2110
Lys Gly Pro Asn Gly Glu Val Thr Tyr Val Leu Gln Asp Asp Tyr Gly
            2115                2120                2125
His Phe Glu Ile Asn Pro Asn Ser Gly Asn Val Ile Leu Lys Glu Ala
        2130                2135                2140
Phe Asn Ser Asp Leu Ser Asn Ile Glu Tyr Gly Val Thr Ile Leu Ala
2145                2150                2155                2160
Lys Asp Gly Gly Lys Pro Ser Leu Ser Thr Ser Val Glu Leu Pro Ile
            2165                2170                2175
Thr Ile Val Asn Lys Ala Met Pro Val Phe Asp Lys Pro Phe Tyr Thr
            2180                2185                2190
Ala Ser Val Asn Glu Asp Ile Arg Met Asn Thr Pro Ile Leu Ser Ile
        2195                2200                2205
Asn Ala Thr Ser Pro Glu Gly Gln Gly Ile Ile Tyr Ile Ile Ile Asp
        2210                2215                2220
Gly Asp Pro Phe Lys Gln Phe Asn Ile Asp Phe Asp Thr Gly Val Leu
2225            2230                2235                2240
Lys Val Val Ser Pro Leu Asp Tyr Glu Val Thr Ser Ala Tyr Lys Leu
            2245                2250                2255
Thr Ile Arg Ala Ser Asp Ala Leu Thr Gly Ala Arg Ala Glu Val Thr
            2260                2265                2270
Val Asp Leu Leu Val Asn Asp Val Asn Asp Asn Pro Pro Ile Phe Asp
            2275                2280                2285
Gln Pro Thr Tyr Asn Thr Thr Leu Ser Glu Ala Ser Leu Ile Gly Thr
    2290                2295                2300
Pro Val Leu Gln Val Val Ser Ile Asp Ala Asp Ser Glu Asn Asn Lys
2305                2310                2315                2320
Met Val His Tyr Gln Ile Val Gln Asp Thr Tyr Asn Ser Thr Asp Tyr
                2325                2330                2335
Phe His Ile Asp Ser Ser Ser Gly Leu Ile Leu Thr Ala Arg Met Leu
            2340                2345                2350
Asp His Glu Leu Val Gln His Cys Thr Leu Lys Val Arg Ser Ile Asp
        2355                2360                2365
Ser Gly Phe Pro Ser Leu Ser Ser Glu Val Leu Val His Ile Tyr Ile
    2370                2375                2380
Ser Asp Val Asn Asp Asn Pro Pro Val Phe Asn Gln Leu Ile Tyr Glu
2385                2390                2395                2400
Ser Tyr Val Ser Glu Leu Ala Pro Arg Gly His Phe Val Thr Cys Val
                2405                2410                2415
Gln Ala Ser Asp Ala Asp Ser Ser Asp Phe Asp Arg Leu Glu Tyr Ser
            2420                2425                2430
Ile Leu Ser Gly Asn Asp Arg Thr Ser Phe Leu Met Asp Ser Lys Ser
        2435                2440                2445
Gly Val Ile Thr Leu Ser Asn His Arg Lys Gln Arg Met Glu Pro Leu
    2450                2455                2460
```

-continued

```
Tyr Ser Leu Asn Val Ser Val Ser Asp Gly Leu Phe Thr Ser Thr Ala
2465                2470                2475                2480

Gln Val His Ile Arg Val Leu Gly Ala Asn Leu Tyr Ser Pro Ala Phe
                2485                2490                2495

Ser Gln Ser Thr Tyr Val Ala Glu Val Arg Glu Asn Val Ala Ala Gly
            2500                2505                2510

Thr Lys Val Ile His Val Arg Ala Thr Asp Gly Asp Pro Gly Thr Tyr
        2515                2520                2525

Gly Gln Ile Ser Tyr Ala Ile Ile Asn Asp Phe Ala Lys Asp Arg Phe
    2530                2535                2540

Leu Ile Asp Ser Asn Gly Gln Val Ile Thr Thr Glu Arg Leu Asp Arg
2545                2550                2555                2560

Glu Asn Pro Leu Glu Gly Asp Val Ser Ile Phe Val Arg Ala Leu Asp
                2565                2570                2575

Gly Gly Gly Arg Thr Thr Phe Cys Thr Val Arg Val Ile Val Val Asp
            2580                2585                2590

Glu Asn Asp Asn Ala Pro Gln Phe Met Thr Val Glu Tyr Arg Ala Ser
        2595                2600                2605

Val Arg Ala Asp Val Gly Arg Gly His Leu Val Thr Gln Val Gln Ala
    2610                2615                2620

Ile Asp Pro Asp Gly Ala Asn Ser Arg Ile Thr Tyr Ser Leu Tyr
2625                2630                2635                2640

Ser Glu Ala Ser Val Ser Val Ala Asp Leu Leu Glu Ile Asp Pro Asp
                2645                2650                2655

Asn Gly Trp Met Val Thr Lys Gly Asn Phe Asn Gln Leu Lys Asn Thr
            2660                2665                2670

Val Leu Ser Phe Phe Val Lys Ala Val Asp Gly Gly Ile Pro Val Lys
        2675                2680                2685

His Ser Leu Ile Pro Val Tyr Ile His Val Leu Pro Pro Glu Thr Phe
    2690                2695                2700

Leu Pro Ser Phe Thr Gln Ser Gln Tyr Ser Phe Thr Ile Ala Glu Asp
2705                2710                2715                2720

Thr Ala Ile Gly Ser Thr Val Asp Thr Leu Arg Ile Leu Pro Ser Gln
                2725                2730                2735

Asn Val Trp Phe Ser Thr Val Asn Gly Glu Arg Pro Glu Asn Asn Lys
            2740                2745                2750

Gly Gly Val Phe Val Ile Glu Gln Glu Thr Gly Thr Ile Lys Leu Asp
        2755                2760                2765

Lys Arg Leu Asp Arg Glu Thr Ser Pro Ala Phe His Phe Lys Val Ala
    2770                2775                2780

Ala Thr Ile Pro Leu Asp Lys Val Asp Ile Val Phe Thr Val Asp Val
2785                2790                2795                2800

Asp Ile Lys Val Leu Asp Leu Asn Asp Asn Lys Pro Val Phe Glu Thr
                2805                2810                2815

Ser Ser Tyr Asp Thr Ile Ile Met Glu Gly Met Pro Val Gly Thr Lys
            2820                2825                2830

Leu Thr Gln Val Arg Ala Ile Asp Met Asp Trp Gly Ala Asn Gly Gln
        2835                2840                2845

Val Thr Tyr Ser Leu His Ser Asp Ser Gln Pro Glu Lys Val Met Glu
    2850                2855                2860

Ala Phe Asn Ile Asp Ser Asn Thr Gly Trp Ile Ser Thr Leu Lys Asp
2865                2870                2875                2880

Leu Asp His Glu Thr Asp Pro Thr Phe Thr Phe Ser Val Val Ala Ser
```

-continued

```
                    2885                2890                2895
Asp Leu Gly Glu Ala Phe Ser Leu Ser Ser Thr Ala Leu Val Ser Val
                2900                2905                2910
Arg Val Thr Asp Ile Asn Asp Asn Ala Pro Val Phe Ala Gln Glu Val
                2915                2920                2925
Tyr Arg Gly Asn Val Lys Glu Ser Asp Pro Gly Glu Val Val Ala
                2930                2935                2940
Val Leu Ser Thr Trp Asp Arg Asp Thr Ser Asp Val Asn Arg Gln Val
2945                2950                2955                2960
Ser Tyr His Ile Thr Gly Gly Asn Pro Arg Gly Arg Phe Ala Leu Gly
                2965                2970                2975
Leu Val Gln Ser Glu Trp Lys Val Tyr Val Lys Arg Pro Leu Asp Arg
                2980                2985                2990
Glu Glu Gln Asp Ile Tyr Phe Leu Asn Ile Thr Ala Thr Asp Gly Leu
                2995                3000                3005
Phe Val Thr Gln Ala Met Val Glu Val Ser Val Ser Asp Val Asn Asp
                3010                3015                3020
Asn Ser Pro Val Cys Asp Gln Val Ala Tyr Thr Ala Leu Leu Pro Glu
3025                3030                3035                3040
Asp Ile Pro Ser Asn Lys Ile Ile Leu Lys Val Ser Ala Lys Asp Ala
                3045                3050                3055
Asp Ile Gly Ser Asn Gly Tyr Ile Arg Tyr Ser Leu Tyr Gly Ser Gly
                3060                3065                3070
Asn Ser Glu Phe Phe Leu Asp Pro Glu Ser Gly Glu Leu Lys Thr Leu
                3075                3080                3085
Ala Leu Leu Asp Arg Glu Arg Ile Pro Val Tyr Ser Leu Met Ala Lys
                3090                3095                3100
Ala Thr Asp Gly Gly Gly Arg Phe Cys Gln Ser Asn Ile His Leu Ile
3105                3110                3115                3120
Leu Glu Asp Val Asn Asp Asn Pro Pro Val Phe Ser Ser Asp His Tyr
                3125                3130                3135
Asn Thr Cys Val Tyr Glu Asn Thr Ala Thr Lys Ala Leu Leu Thr Arg
                3140                3145                3150
Val Gln Ala Val Asp Pro Asp Ile Gly Ile Asn Arg Lys Val Val Tyr
                3155                3160                3165
Ser Leu Ala Asp Ser Ala Gly Gly Val Phe Ser Ile Asp Ser Ser Ser
3170                3175                3180
Gly Ile Ile Ile Leu Glu Gln Pro Leu Asp Arg Glu Gln Gln Ser Ser
3185                3190                3195                3200
Tyr Asn Ile Ser Val Arg Ala Thr Asp Gln Ser Pro Gly Gln Ser Leu
                3205                3210                3215
Ser Ser Leu Thr Thr Val Thr Ile Thr Val Leu Asp Ile Asn Asp Asn
                3220                3225                3230
Pro Pro Val Phe Glu Arg Arg Asp Tyr Leu Val Thr Val Pro Glu Asp
                3235                3240                3245
Thr Ser Pro Gly Thr Gln Val Leu Ala Val Phe Ala Thr Ser Lys Asp
                3250                3255                3260
Ile Gly Thr Asn Ala Glu Ile Thr Tyr Leu Ile Arg Ser Gly Asn Glu
3265                3270                3275                3280
Gln Gly Lys Phe Lys Ile Asn Pro Lys Thr Gly Gly Ile Ser Val Ser
                3285                3290                3295
Glu Val Leu Asp Tyr Glu Leu Cys Lys Arg Phe Tyr Leu Val Val Glu
                3300                3305                3310
```

```
Ala Lys Asp Gly Gly Thr Pro Ala Leu Ser Ala Val Ala Thr Val Asn
        3315                3320                3325
Ile Asn Leu Thr Asp Val Asn Asp Pro Pro Lys Phe Ser Gln Asp
3330                3335                3340
Val Tyr Ser Ala Val Ile Ser Glu Asp Ala Leu Val Gly Asp Ser Val
3345                3350                3355                3360
Ile Leu Leu Ile Ala Glu Asp Val Asp Ser Gln Pro Asn Gly Gln Ile
                3365                3370                3375
His Phe Ser Ile Val Asn Gly Asp Arg Asp Asn Glu Phe Thr Val Asp
                3380                3385                3390
Pro Val Leu Gly Leu Val Lys Val Lys Lys Leu Asp Arg Glu Arg
            3395                3400                3405
Val Ser Gly Tyr Ser Leu Leu Val Gln Ala Val Asp Ser Gly Ile Pro
        3410                3415                3420
Ala Met Ser Ser Thr Ala Thr Val Asn Ile Asp Ile Ser Asp Val Asn
3425                3430                3435                3440
Asp Asn Ser Pro Val Phe Thr Pro Ala Asn Tyr Thr Ala Val Ile Gln
                3445                3450                3455
Glu Asn Lys Pro Val Gly Thr Ser Ile Leu Gln Leu Val Val Thr Asp
                3460                3465                3470
Arg Asp Ser Phe His Asn Gly Pro Pro Phe Ser Phe Ser Ile Leu Ser
            3475                3480                3485
Gly Asn Glu Glu Glu Glu Phe Val Leu Asp Pro His Gly Ile Leu Arg
        3490                3495                3500
Ser Ala Val Val Phe Gln His Thr Glu Ser Leu Glu Tyr Val Leu Cys
3505                3510                3515                3520
Val Gln Ala Lys Asp Ser Gly Lys Pro Gln Gln Val Ser His Thr Tyr
                3525                3530                3535
Ile Arg Val Arg Val Ile Glu Glu Ser Thr His Lys Pro Thr Ala Ile
            3540                3545                3550
Pro Leu Glu Ile Phe Ile Val Thr Met Glu Asp Asp Phe Pro Gly Gly
        3555                3560                3565
Val Ile Gly Lys Ile His Ala Thr Asp Gln Asp Met Tyr Asp Val Leu
    3570                3575                3580
Thr Phe Ala Leu Lys Ser Glu Gln Lys Ser Leu Phe Lys Val Asn Ser
3585                3590                3595                3600
His Asp Gly Lys Ile Ile Ala Leu Gly Gly Leu Asp Ser Gly Lys Tyr
            3605                3610                3615
Val Leu Asn Val Ser Val Ser Asp Gly Arg Phe Gln Val Pro Ile Asp
        3620                3625                3630
Val Val Val His Val Glu Gln Leu Val His Glu Met Leu Gln Asn Thr
    3635                3640                3645
Val Thr Ile Arg Phe Glu Asn Val Ser Pro Glu Asp Phe Val Gly Leu
        3650                3655                3660
His Met His Gly Phe Arg Arg Thr Leu Arg Asn Ala Val Leu Thr Gln
3665                3670                3675                3680
Lys Gln Asp Ser Leu Arg Ile Ile Ser Ile Gln Pro Val Ala Gly Thr
            3685                3690                3695
Asn Gln Leu Asp Met Leu Phe Ala Val Glu Met His Ser Ser Glu Phe
            3700                3705                3710
Tyr Lys Pro Ala Tyr Leu Ile Gln Lys Leu Ser Asn Ala Arg Arg His
        3715                3720                3725
```

-continued

```
Leu Glu Asn Ile Met Arg Ile Ser Ala Ile Leu Glu Lys Asn Cys Ser
    3730                3735                3740

Gly Leu Asp Cys Gln Glu Gln His Cys Glu Gln Gly Leu Ser Leu Asp
3745                3750                3755                3760

Ser His Ala Leu Met Thr Tyr Ser Thr Ala Arg Ile Ser Phe Val Cys
                3765                3770                3775

Pro Arg Phe Tyr Arg Asn Val Arg Cys Thr Cys Asn Gly Gly Leu Cys
            3780                3785                3790

Pro Gly Ser Asn Asp Pro Cys Val Glu Lys Pro Cys Pro Gly Asp Met
        3795                3800                3805

Gln Cys Val Gly Tyr Glu Ala Ser Arg Arg Pro Phe Leu Cys Gln Cys
3810                3815                3820

Pro Pro Gly Lys Leu Gly Glu Cys Ser Gly His Thr Ser Leu Ser Phe
3825                3830                3835                3840

Ala Gly Asn Ser Tyr Ile Lys Tyr Arg Leu Ser Glu Asn Ser Lys Glu
                3845                3850                3855

Glu Asp Phe Lys Leu Ala Leu Arg Leu Arg Thr Leu Gln Ser Asn Gly
            3860                3865                3870

Ile Ile Met Tyr Thr Arg Ala Asn Pro Cys Ile Ile Leu Lys Ile Val
        3875                3880                3885

Asp Gly Lys Leu Trp Phe Gln Leu Asp Cys Gly Ser Gly Pro Gly Ile
    3890                3895                3900

Leu Gly Ile Ser Gly Arg Ala Val Asn Asp Gly Ser Trp His Ser Val
3905                3910                3915                3920

Phe Leu Glu Leu Asn Arg Asn Phe Thr Ser Leu Ser Leu Asp Asp Ser
                3925                3930                3935

Tyr Val Glu Arg Arg Ala Pro Leu Tyr Phe Gln Thr Leu Ser Thr
            3940                3945                3950

Glu Ser Ser Ile Tyr Phe Gly Ala Leu Val Gln Ala Asp Asn Ile Arg
        3955                3960                3965

Ser Leu Thr Asp Thr Arg Val Thr Gln Val Leu Ser Gly Phe Gln Gly
    3970                3975                3980

Cys Leu Asp Ser Val Ile Leu Asn Asn Asn Glu Leu Pro Leu Gln Asn
3985                3990                3995                4000

Lys Arg Ser Ser Phe Ala Glu Val Val Gly Leu Thr Glu Leu Lys Leu
                4005                4010                4015

Gly Cys Val Leu Tyr Pro Asp Ala Cys Lys Arg Ser Pro Cys Gln His
            4020                4025                4030

Gly Gly Ser Cys Thr Gly Leu Pro Ser Gly Gly Tyr Gln Cys Thr Cys
        4035                4040                4045

Leu Ser Gln Phe Thr Gly Arg Asn Cys Glu Ser Glu Ile Thr Ala Cys
    4050                4055                4060

Phe Pro Asn Pro Cys Arg Asn Gly Gly Ser Cys Asp Pro Ile Gly Asn
4065                4070                4075                4080

Thr Phe Ile Cys Asn Cys Lys Ala Gly Leu Thr Gly Val Thr Cys Glu
                4085                4090                4095

Glu Asp Ile Asn Glu Cys Glu Arg Glu Cys Glu Asn Gly Gly Ser
            4100                4105                4110

Cys Val Asn Val Phe Gly Ser Phe Leu Cys Asn Cys Thr Pro Gly Tyr
        4115                4120                4125

Val Gly Gln Tyr Cys Gly Arg Pro Val Val Pro Asn Ile Gln Ala
    4130                4135                4140

Gly His Ser Tyr Val Gly Lys Glu Glu Leu Ile Gly Ile Ala Val Val
```

```
                4145                4150                4155                4160
Leu Phe Val Ile Phe Ile Leu Val Val Leu Phe Ile Val Phe Arg Lys
                    4165                4170                4175
Lys Val Phe Arg Lys Asn Tyr Ser Arg Asn Asn Ile Thr Leu Val Gln
                4180                4185                4190
Asp Pro Ala Thr Ala Ala Leu Leu Asn Lys Ser Asn Gly Ile Pro Phe
                    4195                4200                4205
Arg Asn Leu Arg Gly Ser Gly Asp Gly Arg Asn Val Tyr Gln Glu Val
            4210                4215                4220
Gly Pro Pro Gln Val Pro Val Arg Pro Met Ala Tyr Thr Pro Cys Phe
4225                4230                4235                4240
Gln Ser Asp Ser Arg Ser Asn Leu Asp Lys Ile Val Asp Gly Leu Gly
                4245                4250                4255
Gly Glu His Gln Glu Met Thr Thr Phe His Pro Glu Ser Pro Arg Ile
                    4260                4265                4270
Leu Thr Ala Arg Arg Gly Val Val Cys Ser Val Ala Pro Asn Leu
                4275                4280                4285
Pro Ala Val Ser Pro Cys Arg Ser Asp Cys Asp Ser Ile Arg Lys Asn
                4290                4295                4300
Gly Trp Asp Ala Gly Thr Glu Asn Lys Gly Val Asp Asp Pro Gly Glu
4305                4310                4315                4320
Val Thr Cys Phe Ala Gly Ser Asn Lys Gly Ser Asn Ser Glu Val Gln
                    4325                4330                4335
Ser Leu Ser Ser Phe Gln Ser Asp Ser Gly Asp Asp Asn Ala Ser Ile
                    4340                4345                4350
Val Thr Val Ile Gln Leu Val Asn Asn Val Val Asp Thr Ile Glu Asn
                4355                4360                4365
Glu Val Ser Val Met Asp Gln Gly Gln Asn Tyr Asn Arg Ala Tyr His
            4370                4375                4380
Trp Asp Thr Ser Asp Trp Met Pro Gly Ala Arg Leu Ser Asp Ile Glu
4385                4390                4395                4400
Glu Val Pro Asn Tyr Glu Asn Gln Asp Gly Gly Ser Ala His Gln Gly
                    4405                4410                4415
Ser Thr Arg Glu Leu Glu Ser Asp Tyr Tyr Leu Gly Gly Tyr Asp Ile
                    4420                4425                4430
Asp Ser Glu Tyr Pro Pro His Glu Glu Phe Leu Ser Gln Asp
                4435                4440                4445
Gln Leu Pro Pro Pro Leu Pro Glu Asp Phe Pro Asp Gln Tyr Glu Ala
                4450                4455                4460
Leu Pro Pro Ser Gln Pro Val Ser Leu Ala Ser Thr Leu Ser Pro Asp
4465                4470                4475                4480
Cys Arg Arg Arg Pro Gln Phe His Pro Ser Gln Tyr Leu Pro Pro His
                    4485                4490                4495
Pro Phe Pro Asn Glu Thr Asp Leu Val Gly Pro Pro Ala Ser Cys Glu
                4500                4505                4510
Phe Ser Thr Phe Ala Val Ser Met Asn Gln Gly Thr Glu Pro Thr Gly
                    4515                4520                4525
Pro Ala Asp Ser Val Ser Leu Ser Leu His Asn Ser Arg Gly Thr Ser
                4530                4535                4540
Ser Ser Asp Val Ser Ala Asn Cys Gly Phe Asp Asp Ser Glu Val Ala
4545                4550                4555                4560
```

```
Met Ser Asp Tyr Glu Ser Val Gly Glu Leu Ser Leu Ala Ser Leu His
            4565                4570                4575

Ile Pro Phe Val Glu Thr Gln His Gln Thr Gln Val
            4580            4585
```

HUMAN PROTOCADHERIN PROTEINS AND POLYNUCLEOTIDES ENCODING THE SAME

The present application claims the benefit of U.S. Provisional Application No. 60/257,257 which was filed on Dec. 20, 2000 and is herein incorporated by reference in its entirety.

1. INTRODUCTION

The present invention relates to the discovery, identification, and characterization of novel human polynucleotides encoding proteins that share sequence similarity with mammalian cadherins. The invention encompasses the described polynucleotides, host cell expression systems, the encoded proteins, fusion proteins, polypeptides and peptides, antibodies to the encoded proteins and peptides, and genetically engineered animals that either lack or overexpress the disclosed genes, antagonists and agonists of the proteins, and other compounds that modulate the expression or activity of the proteins encoded by the disclosed genes, which can be used for diagnosis, drug screening, clinical trial monitoring, the treatment of diseases and disorders, and cosmetic or nutriceutical applications.

2. BACKGROUND OF THE INVENTION

Cadherin proteins are membrane proteins that have been linked to a variety of biological processes varying from development, tumor suppression, neural function, and cell communication.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal protocadherins, and especially the protocadherin FAT.

The novel human nucleic acid sequences described herein, encode alternative proteins/open reading frames (ORFs) of 4589, 3852, 4585, and 4588 amino acids in length (see respectively SEQ ID NOS: 2, 4, 6, and 8).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–8 are "knocked-out" they provide a method of identifying phenotypic expression of the particular gene as well as a method of assigning function to previously unknown genes. In addition, animals in which the unique NHP sequences described in SEQ ID NOS:1–8 are "knocked-out" provide a unique source in which to elicit antibodies to homologous and orthologous proteins which would have been previously viewed by the immune system as "self" and therefore would have failed to elicit significant antibody responses.

Additionally, the unique NHP sequences described in SEQ ID NOS:1–8 are useful for the identification of protein coding sequence and mapping a unique gene to a particular chromosome (the gene encoding the described sequences is apparently encoded on human chromosome 11, see GEN-BANK accession number AC024231). These sequences identify actual, biologically verified, and therefore relevant, exon splice junctions as opposed to those that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the NHP ORFs encoding the described NHP amino acid sequences.

5. DETAILED DESCRIPTION OF THE INVENTION

The NHPs described for the first time herein are novel proteins that may be expressed in, inter alia, human cell lines, fetal brain, brain, pituitary, cerebellum, fetal kidney, fetal lung, and 6- and 9-week embryos.

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., NY, at p. 2.10.3) and encodes a functionally equivalent expression product.

Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. Nos. 5,837,458 and 5,723,323 both of which are herein incorporated by reference in their entirety). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–8 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–8, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–8 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–8.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–8 provides detailed information about transcriptional changes involved in a specific pathway, potentially leading to the identification of novel components or gene functions that manifest themselves as novel phenotypes.

Probes consisting of sequences first disclosed in SEQ ID NOS:1–8 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–8 can be utilized in microarrays or other assay formats, to screen collections of genetic material from patients who have a particular medical condition. These investigations can also be carried out using the sequences first disclosed in SEQ ID NOS:1–8 in silico and by comparing previously collected genetic databases and the disclosed sequences using computer software known to those in the art.

Thus the sequences first disclosed in SEQ ID NOS:1–8 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–8. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation and/or as antisense primers in amplification reactions of NHP gene nucleic acid sequences. With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, NY; and Ausubel et al., 1989, Current Protocols in Molecular Biology, Green Publishing Associates and Wiley Interscience, NY.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. For screening techniques, see, for example, Harlow, E. and Lane, eds., 1988, "Antibodies: A Laboratory Manual", Cold Spring Harbor Press, Cold Spring Harbor, N.Y.

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well-known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP nucleotides were obtained from clustered human ESTs, and cDNAs made from brain mRNA (Edge Biosystems, Gaithersburg, Md.).

Several polymorphisms were identified including an A/T polymorphism at the nucleotide position represented by, for example, position 4543 of SEQ ID NO:1 (which can result in a thr or ser at the region corresponding to amino acid (aa) position 1515 of, for example, SEQ ID NO:2), an A/G polymorphism at nucleotide position 4775 (which can result in an asp or gly at aa position 1592), an A/G polymorphism at the nucleotide position represented by, for example, position 6878 of SEQ ID NO:1 (which can result in an asn or ser at the region corresponding to amino acid (aa) position 2293 of, for example, SEQ ID NO:2), a G/C polymorphism at nucleotide position 7227 (which can result in an arg or pro at aa position 2409), a G/A polymorphism at the nucleotide position represented by, for example, position 8263 of SEQ ID NO:1 (which can result in a val or ile at the region corresponding to amino acid (aa) position 2755 of, for example, SEQ ID NO:2), a G/A polymorphism at nucleotide position 10552 (which can result in val or leu at aa position 3518 of, for example, SEQ ID NO:2), a G/A polymorphism at nucleotide position 11434 (which can result in a gly or ser at aa position 3812), a C/A polymorphism at the nucleotide position represented by, for example, position 12691 of SEQ ID NO:1 (which can result in a pro or thr at the region corresponding to amino acid (aa) position 4231 of, for example, SEQ ID NO:2), a G/A polymorphism at nucleotide position 12770 (which can result in a gly or glu at aa position 4257 of, for example, SEQ ID NO:2), and a C/G polymorphism at the nucleotide position represented by, for example, position 12820 of SEQ ID NO:1 (which can result in a leu or val at the region corresponding to amino acid (aa) position 4274 of, for example, SEQ ID NO:2).

The disclosed NHPs are apparently encoded on human chromosome 11 (or possibly human chromosome 8).

The described novel human polynucleotide sequences can be used, among other things, in the molecular mutagenesis/ evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus-mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell-type, thus inactivating the endogenous NHP gene in only that cell-type, by following, for example, the teaching of Gu et al., 1994, Science, 265:103–106. The regulatory sequences required for such a cell-type specific inactivation will depend upon the particular cell-type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

The present invention provides for "knockin" animals. Knockin animals are those in which a gene that the animal does not naturally have in its genome, is inserted. For example, when a human gene is used to replace its murine ortholog in the mouse. Such knockin animals are useful for the in vivo study, testing and validation of, intra alia, human drug targets as well as for compounds that are directed at the same.

5.2 NHPS and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of cancer.

The Sequence Listing discloses the amino acid sequences encoded by the described NHP genes. The NHPs typically display initiator methionines in DNA sequence contexts consistent with a translation initiation site, and a signal like sequences near their N-terminal ends as typical of many other membrane proteins.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing, is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of the NHP, but to assess biological activity, e.g., in certain drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammlian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in $tk^-$, $hgprt^-$ or $aprt^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes:A Practical Approach", New, R.R.C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. Nos. 60/111, 701 and 60/056,713, both of which are herein incorporated

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA, 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341;544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP-mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence that encodes the amino acid sequence shown in SEQ ID NO: 2.

2. The isolated nucleic acid molecule of claim 1, wherein said nucleic acid molecule comprises the nucleotide sequence of SEQ ID NO: 1.

3. An expression vector comprising a nucleic acid sequence that encodes the amino acid sequence of SEQ ID NO:2.

4. The expression vector of claim 3, wherein said nucleic acid sequence is that of SEQ ID NO: 1.

5. A host cell comprising the expression vector of claim 3.

6. A host cell comprising the expression vector of claim 4.

7. A method of producing a protein, comprising culturing a cell of claim 5 under conditions permitting expression of the polypeptide.

8. A method of producing a protein, comprising culturing a cell of claim 6 under conditions permitting expression of the polypeptide.

* * * * *